(12) United States Patent
Varanasi et al.

(10) Patent No.: US 10,442,182 B2
(45) Date of Patent: Oct. 15, 2019

(54) IN VIVO LIVE 3D PRINTING OF REGENERATIVE BONE HEALING SCAFFOLDS FOR RAPID FRACTURE HEALING

(71) Applicants: The Texas A&M University System, College Station, TX (US); The Board of Regents, The University of Texas System, Austin, TX (US)

(72) Inventors: Venu G. Varanasi, Dallas, TX (US); Azhar Ilyas, Arlington, TX (US); Philip Roger Kramer, Dallas, TX (US); Taha Azimaie, Dallas, TX (US); Pranesh B. Aswath, Grapevine, TX (US); Tugba Cebe, Grapevine, TX (US)

(73) Assignees: The Texas A&M University System, College Station, TX (US); The Board of Regents, The University of Texas System, Austin, TX (US)

( * ) Notice: Subject to any disclaimer, the term of this patent is extended or adjusted under 35 U.S.C. 154(b) by 109 days.

(21) Appl. No.: 15/360,788

(22) Filed: Nov. 23, 2016

(65) Prior Publication Data

US 2017/0143831 A1 May 25, 2017

Related U.S. Application Data

(60) Provisional application No. 62/259,556, filed on Nov. 24, 2015.

(51) Int. Cl.
*B33Y 70/00* (2015.01)
*A61K 38/39* (2006.01)
(Continued)

(52) U.S. Cl.
CPC ............ *B33Y 70/00* (2014.12); *A61K 31/722* (2013.01); *A61K 33/00* (2013.01); *A61K 38/39* (2013.01);
(Continued)

(58) Field of Classification Search
CPC .... A61K 41/00; A61K 41/0057; A61K 38/39; A61K 31/722; B33Y 67/00; B33Y 67/0085; B33Y 30/00
See application file for complete search history.

(56) References Cited

U.S. PATENT DOCUMENTS

| 6,027,326 A | 2/2000 | Cesarano et al. |
| 2007/0254005 A1* | 11/2007 | Pathak .................. A61K 35/12 424/423 |

(Continued)

OTHER PUBLICATIONS

Xavier, JR. "Bioactive Nanoengineered Hydrogels for Bone Tissue Engineering: A Growth-Factor-Free Approach." ACS Nano., vol. 9, No. 3, pp. 3109-3118, 2015.
(Continued)

*Primary Examiner* — Christopher J Beccia
(74) *Attorney, Agent, or Firm* — Denise L. Mayfield; Husch Blackwell LLP

(57) ABSTRACT

Bio-Inks and methods of using compositions comprising the bio-Inks are disclosed. 3-D tissue repair and regeneration through precise and specific formation of biodegradable tissue scaffolds in a tissue site using the bio-inks are also provided. Specific methylacrylated gelatin hydrogels (MAC) and methacrylated chitosan (MACh) preparations formulated with sucrose, a silicate-containing component (such as laponite), and/or a cross-linking agent (such as a photo-initiator or chemical initiator), as well as powdered preparations of these, are also disclosed. Kits containing these preparations are provided for point-of-care tissue repair in vivo. Superior, more complete (up to 99.85% tissue
(Continued)

regeneration within 4 weeks applied in situ), and rapid in situ tissue repair and bone formation are also demonstrated.

6 Claims, 33 Drawing Sheets

(51) Int. Cl.
    *A61K 31/722* (2006.01)
    *A61K 33/00* (2006.01)
    *A61N 5/06* (2006.01)
    *B33Y 10/00* (2015.01)
    *A61K 41/00* (2006.01)
    *B33Y 80/00* (2015.01)
    *B29C 64/106* (2017.01)
    *B29K 67/00* (2006.01)

(52) U.S. Cl.
    CPC .............. *A61K 41/00* (2013.01); *A61N 5/062* (2013.01); *B29C 64/106* (2017.08); *B33Y 10/00* (2014.12); *B33Y 80/00* (2014.12); *A61N 2005/0661* (2013.01); *B29K 2067/046* (2013.01); *B29K 2995/0056* (2013.01)

(56) References Cited

U.S. PATENT DOCUMENTS

2009/0111176 A1* 4/2009 Kikawada ........ C07K 14/43563
                                              435/354
2015/0054195 A1   2/2015 Greyf
2016/0144068 A1* 5/2016 Gaharwar ............ A61K 9/0019
                                                424/423

OTHER PUBLICATIONS

Kretlow et al., "Injectable Biomaterials for Regenerating Complex Craniofacial Tissues." Advanced Materials, vol. 21, Nos. 32-33, pp. 3368-3393, 2009.
Annabi et al., "Controlling the Porosity and Microarchitecture of Hydrogels for Tissue Engineering." Tissue Engineering Part B, Reviews, vol. 16, No. 4, pp. 371-383, 2010.
Benton et al., "Photocrosslinking of gelatin macromers to synthesize porous hydrogels that promote valvular interstitial cell function"., Tissue engineering Part A, vol. 15, No. 11, pp. 3221-3230, 2009.
Bose et al., "Bone tissue engineering using 3D printing." Materials Today vol. 16, No. 12, pp. 496-504, 2013.
Boomer et al., "Scaffolding for challenging environments: materials selection for tissue engineered intestine." Journal of Biomedical Materials Research Part A, vol. 102, pp. 3795-3802, 2014.
Bordes et al., "Nano-biocomposites: Biodegradable polyester/nanoclay systems." Progress in Polymer Science, vol. 34, pp. 125-155, 2009.
Tarafder et al., "Microwave Sintered 3D Printed Tricalcium Phosphate Scaffolds for Bone Tissue Engineering." Journal of Tissue Engineering and Regenerative Medicine, vol. 7, No. 8, pp. 631-641, 2013.
Brock et al., "Geometric Determinants of Directional Cell Motility Revealed Using Microcontact Printing." Langmuir, vol. 19, No. 5, pp. 1611-1617, 2003.
Bucholz, R.W., "Nonallograft Osteoconductive Bone Graff Substitutes." Clinical Orthopaedics and Related Research, vol. 395, pp. 44-52, 2002.
Kozlov et al., "The structure and properties of solid gelatin and the principles of their modification." Polymer vol. 24, pp. 651-666, 1983.
Meng et al., "Fabrication of mineralized electrospun PLGA and PLGA/gelatin nanofibers and their potential in bone tissue engineering." Materials Science & Engineering C, vol. 33, pp. 699-706, 2013.

Murphy et al., "Understanding the effect of mean pore size on cell activity in collagen-glycosaminoglycan scaffolds." Cell Adhesion & Migration, vol. 4, No. 3, pp. 377-381, 2010.
Lewis et al., "Direct Ink Writing of Three-Dimensional Ceramic Structures." Journal of the American Ceramic Society, vol. 89, No. 12, pp. 3599-3609, 2006.
Younger et al., "Morbidity at Bone Graft Donor Sites." Journal of Orthopaedic Trauma, vol. 3, pp. 192-195, 1989.
Bhumiratana et al., "Concise Review: Personalized Human Bone Grafts for Reconstructing Head and Face." Stem Cells Translational Medicine, vol. 1, pp. 64-69, 2012.
Elsalanty et al., "Bone Grafts in Craniofacial Surgery." Craniomaxillofacial Trauma & Reconstruction, vol. 2, No. 3/4, pp. 125-134, 2009.
Wu et al., "Development of Biomedical Polymer-Silicate Nanocomposites: A Materials Science Perspective." Materials, vol. 3, pp. 2986-3005, 2010.
Dolatshahi-Pirouz et al., "A combinatorial cell-laden gel microarray for inducing osteogenic differentiation of human mesenchymal stem cells." Scientific Reports, vol. 4, No. 3896, pp. 1-9, 2014.
Balazs et al., "Nanoparticle Polymer Composites: Where Two Small Worlds Meet." Science, vol. 314, No. 5802, pp. 1107-1110, 2006.
Gaharwar et al., "Bioactive Silicate Nanoplatelets for Osteogenic Differentiation of Human Mesenchymal Stem Cells." Advanced Materials, vol. 25, pp. 3329-3336, 2013.
Gaharwar et al., Nanoclay-Enriched poly(varepsilon-caprolactone) Electrospun Scaffolds for Osteogenic Differentiation of Human Mesenchymal Stem Cells, Tissue Engineering Part A, vol. 20, Nos. 15 and 16, pp. 2088-2101, 2014.
Mihaila et al., "The osteogenic differentiation of SSEA-4 subpopulation of human adipose derived stem cells using silicate nanoplatelets." Biomaterials, vol. 34, pp. 9087-9099, 2014.
Grundes et al., "The importance of the hematoma for fracture healing in rats." Acta Orthopaedica Scandinavica, vol. 64, No. 3, pp. 340-342, 1993.
Hutson et al., "Synthesis and Characterization of Tunable Poly(Ethylene Glycol): Gelatin Methacrylate Composite Hydrogels." Tissue Engineering Part A, vol. 17, Nos. 13-14, pp. 1713-1723, 2011.
Ito, Yoshihiro, "Covalently immobilized biosignal molecule materials for tissue engineering." Soft Matter, vol. 4, pp. 46-56, 2008.
Norowski et al., "Biomaterial and antibiotic strategies for peri-implantitis: a review." Journal of Biomedical Materials Research Part B: Applied Biomaterials, vol. 88, pp. 530-543, 2009.
Shimizu et al., "Osteoblastic Differentiation of Periosteium-Derived Cells Is Promoted by the Physical Contact With the Bone Matrix In Vivo." The Anatomical Record, vol. 264, pp. 72-81, 2001.
Shin et al., "The Mechanical Properties and Cytotoxicity of Cell-Laden Double-Network Hydrogels Based on Photocrosslinkable Gelatin and Gellan Gum Biomacromolecules." Biomaterials, Vo. 33, No. 11, pp. 3143-3152, 2012.
Gaharwar et al., "Assessment of using Laponite(R) cross-linked poly(ethylene oxide) for controlled cell adhesion and mineralization." Acta Biomaterialia, vol. 7, pp. 568-577, 2011.
Lebaron et al., "Flow Cytometric Analysis of the Cellular DNA Content of Salmonella typhimurium and Alteromonas haloplanktis during Starvation and Recovery in Seawater." Applied and Environmental Microbiology, vol. 60, No. 12, pp. 4345-4350, 1994.
Loessner et al., "Functionalization, preparation and use of cell-laden gelatin methacryloyl-based hydrogels as modular tissue culture platforms." Nature Protocols, vol. 11, No. 4, pp. 727-746, 2016.
Laughlin et al., "Resorbable Plates for the Fixation of Mandibular Fractures: A Prospective Study." Journal of Oral and Maxillofacial Surgery, vol. 65, pp. 89-96, 2007.
Murphy et al., "3D bioprinting of tissues and organs." Nature Biotechnology, vol. 32, No. 8, pp. 773-785, 2014.
Nishinari et al., "The Effect of Sucrose on the Thermo-Reversible Gel-Sol Transition in Agarose and Gelatin." Polymer Journal, vol. 24, No. 9, pp. 871-877, 1992.
Patel et al., "Microscale Bioadhesive Hydrogel Arrays for Cell Engineering Applications." Cellular and Molecular Bioengineering, vol. 7, pp. 394-408, 2014.

(56) References Cited

OTHER PUBLICATIONS

Raggatt et al., "Cellular and Molecular Mechanisms of Bone Remodeling." The Journal of Biological Chemistry, vol. 285, No. 33, pp. 25103-25108, 2010.
Thomas et al., "Nanoparticle-crosslinked hydrogels as a class of efficient materials for separation and ion exchange." Soft Matter, vol. 7, pp. 8192-8197, 2011.
Rahaman et al., "Bioactive glass in tissue engineering." Acta Biomaterialia, vol. 7, No. 6, pp. 2355-2373, 2011.
Tarnowski et al., "Mineralization of Developing Mouse Calvaria as Revealed by Raman Microspectroscopy." Journal of Bone and Mineral Research, vol. 17, No. 6, pp. 1118-1126, 2002.
Reffitt et al., "Orthosilicic acid stimulates collagen type 1 synthesis and osteoblastic differentiation in human osteoblast-like cells in vitro." Bone, vol. 32, pp. 127-135, 2003.
Sachar et al., "Osteoblasts responses to three-dimensional nanofibrous gelatin scaffolds." Journal of Biomedical Materials Research Part A, vol. 100, pp. 3029-3041, 2012.
Saxena et al., Development of a New Polypropylene-Based Suture: Plasma Grafting, Surface Treatment, Characterization, and Biocompatibility Studies, vol. 11, No. 3, pp. 373-382, 2011.
Langer et al., "Tissue Engineering." Science, New Series, vol. 260, No. 5110, pp. 920-926, 1993.
Sipe, Jean D., "Tissue Engineering and Reparative Medicine." Annals of the New York Academy of Sciences, vol. 961, pp. 1-9, 2002.
Chang et al., "Consise Review: The Periosteum: Tapping into a Reservoir of Clinically Useful Progenitor Cells." Stem Cells Translational Medicine, vol. 1, pp. 480-491, 2012.
Vacanti, C.A., "The history of tissue engineering." Journal of Cellular and Molecular Medicine, vol. 10, No. 3, pp. 569-576, 2006.
Varanasi et al., "Enhanced osteocalcin expression by osteoblast-like cells (MC3T3-E1) exposed to bioactive coating glass (SiO2—CaO—P2O5—MgO—K2O—Na2O system) ions." Acta Biomaterialia, vol. 5, pp. 3536-3547, 2009.
Wang et al., "Cell-laden photocrosslinked GelMADexMA copolymer hydrogels with tunable mechanical properties for tissue engineering." Journal of Materials Science: Materials in Medicine, vol. 25, pp. 2173-2183, 2014.
Ball et al., "Human Periosteum Is a Source of Cells for Orthopaedic Tissue Engineering: a pilot study." Clinical Orthopaedics and Related Research, vol. 469, pp. 3085-3093, 2011.
Annabi N, Nichol JW, Zhong X, Ji C, Koshy S, Khademhosseini A, et al., Controlling the Porosity and Microarchitecture of Hydrogels for Tissue Engineering. Tissue Engineering Part B, Reviews 2010;16:371-83.
Anseth KS., Photocrosslinking of gelatin macromers to synthesize porous hydrogels that promote valvular interstitial cell function., Tissue engineering Part A 2009;15:3221-30.
Bandyopadhyay A., Bone tissue engineering using 3D printing., Materials Today 2013;16:496-504.
Boomer L, Liu Y, Mahler N, Johnson J, Zak K, Nelson T, et al., Scaffolding for challenging environments: materials selection for tissue engineered intestine., Journal of biomedical materials research Part A 2014;102:3795-802.
Bordes P, Pollet E, Avrous.
Bose S., Microwave-sintered 3D printed tricalcium phosphate scaffolds for bone tissue engineering., Journal of tissue engineering and regenerative medicine 2013;7:631-41.
Brock A, Chang E, Ho CC, LeDuc P, Jiang X, Whitesides GM, et al., Geometric determinants of directional cell motility revealed using microcontact printing. Langmuir : the ACS journal of surfaces and colloids 2003;19:1611-7.
Bucholz RW., Nonallograft osteoconductive bone graft substitutes., Clin Orthop Relat Res 2002:44-52.
Burdygina GI., The structure and properties of solid gelatin and the principles of their modification., Polymer 1983;24:651-66.
C, Materials for biological applications, 2013;33:699-706.
Cell Adhesion &, Migration, 2010;4:377-81.

Cesarano J., Direct Ink Writing of Three-Dimensional Ceramic Structures., Journal of the American Ceramic Society 2006;89:3599-609.
Chapman MW., Morbidity at bone graft donor sites., Journal of orthopaedic trauma 1989;3:192-5.
Concise Review:, Personalized Human Bone Grafts for Reconstructing Head and Face., Stem Cells Transl Med 2012;1:64-9.
Craniofacial Surgery., Craniomaxillofacial Trauma &, Reconstruction 2009;2:125-34.
Development of Biomedical Polymer-Silicate Nanocomposites:, A Materials Science Perspective., Materials 2010;3:2986-3005.
Dolatshahi-Pirouz A, et al., A combinatorial cell-laden gel microarray for inducing osteogenic differentiation of human mesenchymal stem cells., Scientific reports 2014;4:3896.
Emrick T, Russell TP., Nanoparticle polymer composites: where two small worlds meet.
Gaharwar AK, Mihaila SM, Swami A, Patel A, Sant S, Reis RL, et al., Advanced materials 2013;25:3329-36., 2013.
Gaharwar AK, Mukundan S, Karaca E, Dolatshahi-Pirouz A, Patel A, Rangarajan K, et al., Nanoclay-enriched poly (varepsilon-caprolactone) electrospun scaffolds for osteogenic differentiation of human mesenchymal stem cells., Tissue engineering Part A 2014;20:2088-101.
Gomes ME., The osteogenic differentiation of SSEA-4 subpopulation of human adipose derived stem cells using silicate nanoplatelets., Biomaterials 2014;35:9087-99.
Grundnes O, Reikeras O., Acta orthopaedica Scandinavica 1993;64:340-2.
Hutson CB, Nichol JW, Aubin H, Bae H, Yamanlar S, Al-Haque S, et al., Synthesis and characterization of tunable poly (ethylene glycol): gelatin methacrylate composite hydrogels., Tissue engineering Part A 2011;17:1713-23.
Ito Y., Covalently immobilized biosignal molecule materials for tissue engineering., Soft Matter 2008;4:46-56.
Jr., Bumgardner JD., Biomaterial and antibiotic strategies for peri-implantitis: a review.
Kagayama M, Shimauchi H., The Anatomical record 2001;264:72-81.
Khademhosseini A., The mechanical properties and cytotoxicity of cell-laden double-network hydrogels based on photocrosslinkable gelatin and gellan gum biomacromolecules., Biomaterials 2012;33:3143-52.
Kline BP, Schmidt G., Assessment of using laponite cross-linked poly(ethylene oxide) for controlled cell adhesion and mineralization.
Lebaron P, Joux F., Applied and Environmental Microbiology 1994;60:4345-50.
Loessner D, Meinert C, Kaemmerer E, Martine LC, Yue K, Levett PA, et al., Functionalization, preparation and use of cell-laden gelatin methacryloyl-based hydrogels as modular tissue culture platforms., Nat Protocols 2016;11:727-46.
Malloy RB, Kent JN., Resorbable plates for the fixation of mandibular fractures: a prospective study.
Murphy SV, Atala A., 3.
Nishinari K, Watase M, Kohyama K, Nishinari N, Oakenfull D, Koide S, et al., The Effect of Sucrose on the Thermo-Reversible Gel-Sol Transition in Agarose and Gelatin., Polym J 1992;24:871-7.
Patel RG, Purwada A, Cerchietti L, Inghirami G, Melnick A, Gaharwar AK, et al., Microscale Bioadhesive Hydrogel Arrays for Cell Engineering Applications., Cellular and molecular bioengineering 2014;7:394-408.
Raggatt LJ, Partridge NC., The Journal of biological chemistry 2010;285:25103-8.
Raghavan SR., Nanoparticle-crosslinked hydrogels as a class of efficient materials for separation and ion exchange., Soft Matter 2011;7:8192-7.
Rahaman MN, Day DE, Bal BS, Fu Q, Jung SB, Bonewald LF, et al., Bioactive glass in tissue engineering., Acta biomaterialia 2011;7:2355-73.
Reffitt DM, Ogston N, Jugdaohsingh R, Cheung HFJ, Evans BAJ, Thompson RPH, et al., Orthosilicic acid stimulates collagen type 1 synthesis and osteoblastic differentiation in human osteoblast-like cells in vitro., Bone 2003;32:127-35.

(56) References Cited

OTHER PUBLICATIONS

Sachar A, Strom TA, Serrano MJ, Benson MD, Opperman LA, Svoboda KK, et al., Osteoblasts responses to three-dimensional nanofibrous gelatin scaffolds., Journal of biomedical materials research Part A 2012;100:3029-41.
Saxena S, et al., Macromolecular bioscience 2011;11:373-82., 2011.
Science (, New York, NY) 1993;260:920-6.
Sipe JD., Tissue Engineering and Reparative Medicine., Annals of the New York Academy of Sciences 2002;961:1-9.
The Periosteum:, Tapping into a Reservoir of Clinically Useful Progenitor Cells., Stem Cells Translational Medicine 2012;1:480-91.
Vacanti CA., Journal of Cellular and Molecular Medicine, 2006;10:569-76.
Varanasi VG, Saiz E, Loomer PM, Ancheta B, Uritani N, Ho SP, et al., Enhanced osteocalcin expression by osteoblast-like cells (MC3T3-E1) exposed to bioactive coating glass ($SiO_2$—CaO—$P_2O_5$—MgO—$K_2O$—$Na_2O$ system) ions., Acta biomaterialia 2009;5:3536-47.56.
Wang H, Zhou L, Liao J, Tan Y, Ouyang K, Ning C, et al., Cell-laden photocrosslinked GelMADexMA copolymer hydrogels with tunable mechanical properties for tissue engineering. Journal of Materials Science: Materials in, Medicine 2014;25:2173-83.
Williams A, Stevens MM., Human periosteum is a source of cells for orthopaedic tissue engineering: a pilot study.
Moore et al., "Photometric Ninhydrin Method for Use in the Chromatography of Amino Acids." The Journal of Biological Chemistry, vol. 176, pp. 367-388, 1948.
McKibbin, B. "The biology of fracture healing in long bones." The Journal of Bone and Joint Surgery, vol. 60-B, No. 2, pp. 150-162, 1978.
Dunne et al., "Influence of particle size and dissolution conditions on the degradation properties of polylactide-co-glycolide particles." Biomaterials, vol. 21, pp. 1659-1668, 2000.
Arnett, T.R., "Extracellular pH Regulates Bone Cell Function." The Journal of Nutrition, vol. 138, pp. 415S-418S, 2008.
Panetta et al., "Tissue engineering in cleft palate and other congenital malformations." Pediatric Research, vol. 63, No. 5, pp. 545-551, 2008.
Sabnis et al., "Cytocompatibility studies of an in situ photopolymerized thermoresponsive hydrogel nanoparticle system using human aortic smooth muscle cells." Journal of Biomedical Materials Research Part A, vol. 91, No. 1, pp. 52-59, 2009.
Bouxsein et al., "Guidelines for Assessment of Bone Microstructure in Rodents Using Micro-Computed Tomography" Journal of Bone and Mineral Research, vol. 25, No. 7, pp. 1468-1486, 2010.
Guda et al., "In vivo performance of bilayer hydroxyapatite scaffolds for bone tissue regeneration in the rabbit radius." Journal of Materials Science: Materials in Medicine, vol. 22, pp. 647-656, 2011.
Sunami et al., "Influence of the pattern size of micropatterned scaffolds on cell morphology, proliferation, migration and F-actin expression." Biomaterials Science, vol. 2, pp. 399-409, 2014.
Gentile et al., "An Overview of Poly(lactic-co-glycolic) Acid (PLGA)-Based Biomaterials for Bone Tissue Engineering." International Journal of Molecular Sciences, vol. 15, pp. 3640-3659, 2014.
Toyota et al. "Controlling Cell Migration with Micropatterns." Innovations in Biotechnology, Dr. Eddy C. Agbo (Ed.), InTech, pp. 187-208, 2012. [Available from: http://www.intechopen.com/books/innovations-in-biotechnology/controlling-cell-migration-with-micropatterns].
Oppenheimer et al., "Craniofacial Bone Grafting: Wolff's Law Revisited." Craniomaxillofacial Trauma & Reconstruction, vol. 1, No. 1, pp. 49-61, 2008.
Bell, R.B., "Computer Planning and Intraoperative Navigation in Cranio-Maxillofacial Surgery." Oral and Maxillofacial Surgery Clinics of North America, vol. 22, pp. 135-156, 2010.
Josh, A.M., "Process planning for the rapid machining of custom bone implants USA.", Graduate Theses and Dissertations, Iowa State University, Digital Repository, Ames, Iowa, pp. 1-81, 2011.
Wang et al., "Orthopaedic Implant Technology: Biomaterials from Past to Future" Annals of the Academy of Medicine, vol. 40, No. 5, pp. 237-244, 2011.
Nichol et al., "Cell-laden microengineered gelatin methacrylate hydrogels." Biomaterials, vol. 31, pp. 5536-5544, 2010.
Zandi, M., "Studies on the Gelation of Gelatin Solutions and on the Use of Resulting Gels for Medical Scaffolds." Dissertation, Universität Duisburg-Essen, pp. 1-154, 2008.
Mandair et al., "Contributions of Raman spectroscopy to the understanding of bone strength." BoneKEy Reports, vol. 4, No. 620, pp. 1-8, 2015.
McElderry, D.P., "Dynamics of Mineralization During Bone Development." Dissertation, The University of Michigan; pp. 1-162, 2012.
Wischke et al., "Fluorescein isothiocyanate labelled bovine serum albumin (FITC-BSA) as a model protein drug: opportunities and drawbacks." Die Pharmazie, vol. 61, pp. 770-774, 2006.
Ma et al., "Hierarchical Nanofibrous Microspheres with Controlled Growth Factor Delivery for Bone Regeneration." Advanced Healthcare Materials, vol. 4, pp. 2699-2708, 2015.

\* cited by examiner

10a)

21a

21b

US 10,442,182 B2

IN VIVO LIVE 3D PRINTING OF REGENERATIVE BONE HEALING SCAFFOLDS FOR RAPID FRACTURE HEALING

CROSS-REFERENCE TO RELATED APPLICATIONS

The present application claims priority to U.S. Provisional Application Ser. No. 62/259,556, filed Nov. 24, 2015, the contents of which are incorporated herein by reference in its entirety.

STATEMENT REGARDING FEDERALLY SPONSORED RESEARCH OR DEVELOPMENT

The invention was made with government support under Grant No. NIH Grant R03DE023872 awarded by the National Institutes of Health. The government has certain rights in the invention.

FIELD OF THE INVENTION

The present invention relates to the field of 3-D technologies and uses thereof in bone repair and bone regeneration.

BACKGROUND OF THE INVENTION

Nearly 4,000,000 bone grafting procedures are performed globally every year at a cost of 2.3 billion dollars and it is projected to reach 3.4 billion dollars in 2023 [30]; around 600,000 of these are performed in the US [31].

Bone grafts are used to fill large volumes of bone loss from fracture, traumatic injury or other physical disorder that affects bone architecture and function in the body. Such types of bone loss lead to formation of critical size defects (CSD), which without grafting or other intervention usually lead to non-union. Bone grafts must have adequate mechanical properties to support new bone formation in the defect and be osteogenic and resorbable to maintain continuity of support during bone regeneration [32]. Currently, allograft, autografts and in some cases xenografts are being used for CSD treatment. However, these materials can cause disease transmission, donor site morbidity, and acute immunological responses that can lead to bone resorption and graft rejection [33]. Also, resources for allografts and autografts are limited. Therefore, there is a vital need for new bone substitutes that can rapidly heal these defects to reduce patient discomfort and medical care costs.

The essential component for an acceptable treatment approach for healing fractures is that the treatment be provided as soon after the bone defect has occurred, and that it facilitates turnover of bone within 4-8 weeks.

Current approached to bone repair have been described to involve the fabrication of a scaffold using a 3-D printing technique. These fabricated scaffold may then be implanted into a patient at a site in need of repair of a small to large bone fracture. Conventional methods that are being used for fabrication of 3D scaffolds are labor-intensive, time-consuming, and do not provide precise control over the scaffold's architecture. Rapid prototyping (RP) is a technique that can be divided into the additive and subtractive method. Additive rapid prototyping (ARP) is more popular because of its ability to create further complex shapes and hollow structures. ARP is increasingly used for tissue engineering [38] and craniofacial reconstruction [37]. Currently in craniofacial reconstruction, APR technology is used for preoperative treatment planning by fabricating a 3D shape of the site of surgery and practicing the surgery on the model [37].

ARP is a broad category that includes many different methods including stereolithography, fused deposition modeling, direct metal laser sintering, laminated object manufacturing, electron beam melting, selective laser sintering, laser engineered net shaping, and 3-dimensional printing (3DP). 3DP does not require heat for its functionality which makes it useful for cell or growth factor incorporation. This feature made 3DP an attractive method for tissue engineering [39]. Robocasting or direct ink writing (DIW) is a subcategory of 3DP that is based on a computer aided fabrication method that uses extrusion of the "ink" while moving in all three axes to make a 2D layer. By adding these 2D layers on top of each other, a 3D object can be created. The robocaster allows precise control of micro patterning by determining the dimensions of filaments, the size and shape of pores and the percentage of porosity of the scaffold [40-42].

Although extensive research has been conducted on suitable biomaterials for 3DP, there are few well-established biomaterials that can be 3D printed and implanted in the body [42]. These materials include bioceramics such as bioglass, TCP, and HA, and biopolymers such as PLA, PGA, and PLGA.

Previously described techniques for achieving bone fracture repair include the use of fixative metals, or the use of resorbable biopolymers. The use of either fixative metals or resorbable polymer materials in bone repair suffers from several disadvantages, including, among other things, a lack of bone bioactivity of these materials. This ultimately results in prolonged patient healing times and, many times, incomplete bone healing results to the patient. In addition, and because metal implants do not resorb into the body, the implant remains fixated in the patient's bone. In addition, optimal complete bony replacement at the bone defect (fracture) site in the patient does not occur.

As noted, biopolymers have also been proposed and used for repair of bone fracture. However, currently described biopolymers for this use in healing bone fracture lacks the needed strength to support rapid bone turnover, among other drawbacks.

Existing 3-D printing methods have also been found inadequate for the repair of bone fracture, primarily because current methods require significant added lead time for fabrication of a suitable scaffold before implant at a fracture site may be made. Moreover, 3-D methods previously described do not provide alternative approaches to a pre-fabricated scaffold implant for bone repair, or of a suitable, biocompatible and visco-elastic material suitable for bone cell integration and bone formation.

Craniofacial reconstruction surgeries present a particularly challenging problem concerning repair of bone because of the complex anatomy of this region and its proximity to the vital tissues, among other challenges. These surgeries have required the fabrication of a custom implant prior to surgery. Such pre-fabrication techniques for a bone graft fabrication are described, for example, in US PUB 20150054195 (Grey). Fabrication of a custom implant is time consuming, and creates a delay in when a patient may undergo a corrective/reconstructive surgery. Delay in surgical intervention is recognized as creating an increased risk that the surgery will not be successful and/or will provide less than patient acceptable results. Therefore, a new surgical method is needed to treat bone defects with the least possible delay, while at the same time not sacrificing any significant loss in bone repair precision or implantation/repair success rate.

The medical arts remain in need of alternative and improved materials and techniques for providing bone fracture repair that are sufficiently strong and suitable for immediate bone treatment without the need for a prefabricated scaffold, and that have improved complete boney replacement at a fracture site than that achievable with metal implants. promote not adapted for use in direct printing of materials into defects for immediate treatment of the fracture/defect site.

SUMMARY OF THE INVENTION

The present invention, in a general and overall sense, provides materials and methods for repairing bone fractures, defects and other bone deficiencies in vivo.

Method of 3-D Printing for Tissue and Bone Defect Repair In Vivo:

In one aspect, a system for printing a porous scaffold in vivo in situ is disclosed. In some embodiments, the method comprises preparing a slurry comprising biosilicate nanoparticles and osteoinductive biopolymers; and applying the slurry, through a printer head attached to a motorized manifold; and being driven by a CAD program, to a bone fracture site.

A method for providing a printing a regenerative scaffold into the defect of the patient is disclosed comprising: selecting an optimized scaffold slurry; calibrating the printer parameters; recording the surface profilometry in 3 dimensions of the defect; programming the defect into the CAD program; engaging the printer head; filling the defect with the printed scaffold while maintaining a small gap; and closing the periosteum and skin.

As part of the method of some embodiments of the 3-D bio printing method, the bio-Ink in its final formulation will be fed into a delivery device, such as the nozzle of an automated 3-D printing device, and provided as a series of layers at the tissue site of an animal, including humans.

In another embodiment, the method may include the step of first preparing a quantity of the bio-Ink by combining an amount of the lyophilized MAG powder with a quantity of silicate-based nanoparticles (such as hydrous sodium lithium magnesium silicate (Laponite™) nanoparticles), and an appropriate volume of a sucrose-containing solution having a defined sucrose concentration may be mixed to form a bio-Ink. This bio-Ink will have a suitable viscosity that will permit it to be extruded through a nozzle having a extrusion component, such as a needle, the needle or other extrusion component having a size of between about a 14 to about a 32 gauge size (in some embodiments, a gauge 30 (0.2 mm) dispenser tip).

Printing (i.e., delivery) of the bio-Ink at a tissue site may be accomplished by providing a defined quantity of the bio-Ink extruded through a small gauge dispenser tip, such as a needle having a size of about 14 (1.55 mm) to about 32 (about 0.1 mm) gauge, into and/or around a defined tissue site sufficient to cover the specific dimensions of the tissue site within about 0.01 mm to about 1.0 mm margin (or within a 0.1 mm to about 0.5 mm margin) of the targeted tissue area perimeter. In the case of a bone defect repair, greater than 80%, or from about 85 to about 99%, or from about 86% to about 99.9833%, of the targeted bone tissue area being repaired, will demonstrate successful new bone growth within a period of less than about 4 weeks upon in vivo treatment with the direct 3-D reconstructive techniques and materials provided here.

The conditions under which the bio-Ink will be delivered will be strictly controlled so as to accommodate the proper formation of filaments of the bio-Ink within the tissue site. For example, the temperature and the rate of deposition shall be controlled so as to avoid any compromise of the extruded bio-Ink material and/or any compromise of the filaments that may be formed upon cross-linking of the bio-Ink material (cross-linking to be initiated in the presence of a physiologically compatible intensity and wavelength of UV light and an appropriate cross-linking agent, such as a photo-initiator (e.g., IRGA-CURE) or chemical initiator compound). The conditions under which the extrusion of the slurry material and/or micro-patterning process are conducted shall be controlled so as to minimize and/or eliminate the probability of any tissue destruction or degradation at and surrounding the tissue site being treated. The conditions under which the deposition are carried out are also optimized to provide the most appropriate conditions for fostering the successful formation of a suitable biodegradable scaffold structure (having a plurality of defined pore sizes of between 300 µm and 700 µm), as filaments of the material solidify and/or "cure" within the wound site, upon exposure to a physiologically compatible wavelength and intensity of UV light (such as an about 365 nm UV light illumination wavelength at an intensity of up to about 50 mW/sq.cm), in the presence of a cross-linking agent.

The method may provide a any number of different configurations and geometries of bio-Ink deposition at a desired site, such as to provide a single layer, multiple stacked or unstacked layers, mesh configuration, triangular configuration, rectangular configuration, or other configuration as may be best suited for the, for example, tissue site, being repaired.

Biocompatible Regenerative Bone Slurry Material:

In another aspect, a pharmaceutical composition comprising a biocompatible soft or hard regenerative tissue material is provided. In some embodiments, this material may be described as a semi-solid-material, such as a slurry having liquid flow properties suitable for use as an extrudable material suitable for extrusion through a nozzle apparatus having a delivery tip, such as a cap or needle of a defined size.

The slurry material may comprise the gel materials described herein, such as MACh or MAG, together with a sucrose component (anywhere from about 5% to about 20% sucrose) and a silicate-based (nanoparticle) component, for example, laponite. The slurry may also comprise a physiologically acceptable solution, such as saline or phosphate buffered saline (PBS). The slurry may also include a cross-linking agent, such as a photo-initiator component (e.g., 2-hydroxy-1(4(hydroxyethoxy)phenyl)2-methyl-i-propanone) or chemical initiator component, or other appropriate cross-linking agent.

The slurry should have a viscosity that will permit the material to pass though or be extruded though the delivery tip, such as a needle, having a 14 (1.55 mm) to an about 32 (0.1 mm) gauge size (about 30 gauge size in some embodiments). These slurry will have a liquid-like viscosity at 37° C. to about 40° C., and a more gel-like viscosity at lower temperatures. The viscosity of the slurry may be described as between about 30 mili-Pascal seconds (0.3 centi-Poise) to about 600 kilo-Pascal seconds (6×106 centi-Poise). The viscosity of the preparation as an extrusion ready formula may be described as between about 300 mili-Pascal seconds (0.3 centi-Poise) to about less than 1 Pascal seconds (less than 1 centi-Poise), or from about 300 mili-Pascal seconds (0.3 centi-Poise) to about 900 mili-Pascal seconds (0.9 centi-Poise).

Soft Tissue and/or Bone Tissue Repair Kit:

In another aspect, a soft tissue and/or bone tissue repair kit is provided. It is envisioned that the kit, and various of the components of the kit, may be used to provide point of care attention to an animal and/or human without the necessity of an immediate hospital stay or visit.

The components of the kit will include a bio-Ink component (or the individual powdered components that make up the bio-Ink to be combined by the user when needed, or an anhydrous form of the MAC or MAG material that includes a laponite or other silicate-containing component, and a sucrose or other sugar component), and a set of instructions describing the methods for using and/or combining the components of the kit. A dispensing device (such as a syringe) for applying a liquid like form of the bio-Ink may also be included. A descriptive material insert illustrating the technique for providing a covering (such as mesh-like or layer-like covering) of the bio-Ink to a desired tissue/bone area may also be included.

By way of example, a powdered component of the bio-Ink (e.g., a freeze-dried preparation (lyophilized) comprising an amount of methacrylated gelatin (MAG)) or MACh, may be included with the kit. An appropriate physiologically acceptable carrier solution, such as saline or PBS, suitable for suspending the MAG or MACh material, may also be included with the kit.

The freeze-dried (lyphylized) preparations of MAG or MAC have an extended shelf-life, and may be stored at $-80°$ C. until the user is ready to use the preparation.

For use, the MAG or MAC powdered material will be combined with a volume of a solution of saline, that may also include a silicate-based material (such as a nano-silicate laponite (LP)) and sucrosepreparation) and sucrose or other sugar. This solution of the silicate-based material (such as LP) and sucrose will in some embodiments include a concentration of sucrose sufficient to provide a sucrose concentration of about 5% to about 20% w/w$_{MAG/MACh}$ in a resulting ready to use gelatin. The sucrose solution and LP nanoparticles will be heated before combining with the MAG and or MACh material. This combination of MAG and MACh in a warmed/heated solution of the laponite/sucrose solution, will be processed (centrifuged, debubbled) prior to use to provide a ready to use bio-Ink medicament suitable for applying as a single bolus to a tissue site or as a series of filamentous layers (such as by extrusion through a delivery tip of a syringe), or for application using an in situ micro-needle deposition technique.

Bio-Ink:

The final extrusion-ready preparation of the bio-Ink may be formulated to include about 1% to about 20% wt. MAG (in some embodiments, about 10 wt. % MAG), about 1% to about 8% wt. LP (in some embodiments, between 2% and about 4% wt. LP), or other appropriate silicate-based material), about 5% to about 20% w/w$_{gelatin}$ sucrose (in some embodiments, about 5% to about 10%), and a pharmacologically acceptable carrier solution or solvent (for example, PBS, or other solvent that is not toxic to (i.e., does not inhibit or prevent) cell viability and/or would impede or reduce the rate of cell bone tissue formation and growth. Examples of harmful, biologically toxic solvents that would not be particularly useful in the present techniques include chloroform, acetone, DMF THF, and others.

Alternatively, the bio-Ink may be formulated to include a methacrylated chitosan (MACh) material. In these formulations, the concentration of MACh may be described as a MACh with sucrose (about 5% to about 20%) preparation provided in a 1:1 mole ratio with chitosan. From this preparation, a 4% by weight MACh formulation, may be prepared for use as a bio-Ink for tissue repair.

In some embodiments, the silicate-based nanoparticle material (for example, laponite nanoparticles) will be combined with a sugar containing preparation, such as sucrose (SU), in a defined volume of a physiologically acceptable buffer solution, such as Dulbecco's Phosphate Buffered Saline (DPBS), prior to being combined with the MAG of MAG-LP composite material.

The bio-Ink may in some embodiments, also contain a variety of ingredients such as, but not limited to, demineralized allograft bone matrix (DMB) 145, a cross-linking agent (such as a photo-initiator (IRGACURE 2529) or chemical initiator (Genepin), an antibiotic, a compound to increase the biodegradability of the bio-Ink, or any combination of these ingredients.

The antibiotic may, for instance, be a compound such as, but not limited to, amoxicillin, doxycycline, gentamicin or clindamycin or some combination thereof. The compound to increase the biodegradability of the scaffold material once formed in situ in the animal after deposition of the bio-Ink may, for instance, be a compound such as, but not limited to, cellulose acetate (CA), or cellulose acetate phthalate (CAP) or some combination thereof.

The bio-Ink preparations may be described as having a particular viscosity. The viscosity of the bio-ink must be sufficiently fluid-like and/or liquid-like to permit the microextrusion of the bio-Ink through a needle having a 14 (1.55 mm) to an about 32 (0.1 mm) gauge size. The viscosity may be further described as between about 30 mPs·s to about 600 kPa's, having a droplet size of about 5 micron to 1 millimeter wide. The average storage modulus (as well as depends on strain rate and frequency) is varied between 7,500 to 10,000 Pa and loss modulus is approximately 10-Pa. The special resolution and gelatin speed is medium (7 to 13 MM/SEC) as compared to laser-assisted printing and inkjet printing. The gelatin methods of micro-extrusion include chemical photo-crosslinking, shear-thinning, and temperature.

The bio-Inks of the present invention are characterized by being able to form a partially- or fully-gelatinous phase with the gelatin, chitosan, or other gelatinous components, such that any included particulate material included as part of the gel, such as particles of synthetic bone substitute, are not simply suspended, but are partially or fully homogenous with the preparation as a mixture.

The following abbreviations are used throughout the description of the preset invention.

0-10 A bio-ink of 0% LP, 10% MAG, 2% Suc, and 0.05% I2959
2-10 A bio-ink of 2% LP, 10% MAG, 2% Suc, and 0.05% I2959
2D Two Dimensional
3D Three Dimensional
3DP 3-Dimensional Printing
4-10 A bio-ink of 4% LP, 10% MAG, 2% Suc, and 0.05% I2959
6-10 A bio-ink of 6% LP, 10% MAG, 2% Suc, and 0.05% I2959
6-15 A bio-ink of 6% LP, 15% MAG, 3% Suc, and 0.075% I2959

6-20 A bio-ink of 6% LP, 20% MAG, 4% Suc, and 0.1% I2959
α-MEM Alpha modified Minimum Essential Media
μCT Micro Computed tomography
ACGIH American Conference of Governmental Industrial Hygienists
ARP Additive Rapid Prototyping
BMP Bone Morphogenetic Protein
bpm Beats Per Minute
BSA Bovine Serum Albumin
BSE Back-Scattered Electron microscopy
Ca Calcium
CAD Computer Aided Design
CAM Computer Aided Manufacturing
CSD Critical Size Defects
CT Computed tomography
DAPI 4',6-Diamideino-2-Phenylindole
DMF Dimethylformamide
DPBS Dulbecco's Phosphate Buffered Saline
ECM Extra Cellular Matrix
EDS Energy-Dispersive X-ray Spectroscopy
EtO Ethylene Oxide
FBS Fetal Bovine Serum
FGF Fibroblast Growth Factors
FITC-BSA Fluorescein isothiocyanate conjugated bovine serum albumin
FTIR Fourier Transform Infrared Spectroscopy
GPS Global Positioning System
H&E Hematoxylin and Eosin
HA HydroxyApatite
I2959 IRGACURE2959
IACUC Institutional Animal Care and Use Committee
ICP-OES Inductively coupled plasma optical emission spectrometry
IR Infrared electromagnetic wave
IRB Institutional Review Board
ISP In-Situ Printing
Krpm Kilo Revolutions Per Minute
LP Laponite
MA Methacrylate Anhydride
MAG Methacrylated Gelatin
MI Mineral isle
MRI Magnetic Resonance Imaging
NH3 Amino chemical group
O Oxygen
OH Hydroxyl chemical group
P Phosphorous
PBS Phosphate Buffered Saline
PCL Poly Caprolactone
PDPC Periosteum Derived Progenitor Cells
PEG Poly Ethylene Glycol
PII Prosthetic Implant Infection
PLA Poly Lactic Acid
PGA Poly Glycolic Acid
PLGA Poly Lactic-co-Glycolic Acid
RB Regenerated Bone
RGD Arginylglycylaspartic acid
RMF Re-Mineralization Front
RP Rapid Prototyping
rpm Revolution Per Minute
RUNX2 Runt-related Transcription Factor 2
SB Surrounding Bone (indigenous rat bone)
SEI Secondry Electron Imaging
SEM Scanning Electron Microscopy imaging
Si+4 Silicon ion with a charge of +4
Suc Sucrose
TCP Tri-Calcium Phosphate
THF Tetrahydrofuran
UV Ultra Violet light
VEGF Vascular Endothelial Growth Factor

DETAILED DESCRIPTION OF THE PREFERRED EMBODIMENT

Figure 1:
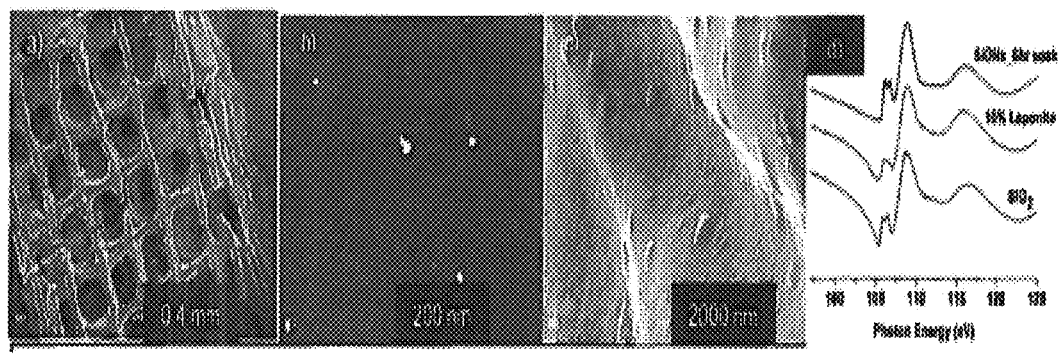
FIG. 1 is shows bio silicate nanoparticle-gelatin methacrylate 30 printed scaffolds for bone regeneration. Scaffolds (a, SEM) showed for dispersed biosilicate nanoparticles (b), ECM-like surface nanostructure (c). and similar chemistry similar to SiONx and SiOx chemistry (d, XANES)

Embodiments of the claimed invention are directed to a system for printing a porous scaffold in vivo in situ comprising: slurries comprised of biosilicate nanoparticles and osteoinductive biopolymers wherein the ratio of inorganic to polymer phase optimizes tensile, compressive, and bending strength of the material; a printer head; a motorized manifold, wherein the motorized manifold permits the movement of the printer head; and a CAD program, wherein the CAD program is able to generate a file to print based on the recorded profilometry of the area of interest. In certain embodiments, the biosilicate nanoparticles may be comprised of laponite, while in other embodiments the biosilicate nanoparticles may be comprised of silicon oxynitride other embodiments may utilize a combination of both compounds. Other embodiments can include bioactive glass nanoparticles or microparticles that can be fabricated to also take on the bone defect shape. Other embodiments can include the combination of laponite, bioactive glasses, and silicon oxynitride nano/micro-particles. In certain embodiments, the osteoinductive biopolymers may be comprised of gelatin methacrylate, while in other embodiments, the osteoinductive biopolymers may be comprised of chitosan methacrylate. In certain embodiments, the osteoinductive biopolymers may be comprised of a combination of both materials. In certain embodiments, the scaffold structural stability may be ensured through the utilization of dispersants, flocculants, and titrants in order to overcome inadequate slurry viscoelastic properties.

An embodiment of the claimed invention is directed to a method of in vivo "live" (in situ) 3-D printing of regenerative bone healing scaffolds comprising: preparing an optimized scaffold slurry comprising a bio-ink of methacrylate chitosan, wherein the bio-ink comprises biosilicate nanoparticles and osteoinductive biopolymers with optimized modulus and compressive strength, that maximally up-regulate antioxidants, reduces reactive oxygen species activity, and accelerates biomineral formation; determining the specific size and depth parameters of a tissue defect area and calibrating these parameters into a printer (e.g., defect size, depth), recording the surface profilometry in 3 dimensions to record the defect shape; programming the defect into the CAD program; engaging the printer head near the defect using the motorized manifold; applying the bio-ink to form a printed scaffold at the tissue defect site, maintaining less than a 0.3 mm gap (such as a gap of 0.1 mm) from the outside perimeter of the tissue defect and the printed scaffold, and exposing the printed scaffold to UV light in the presence of a photo-initiator to form a gelatinous printed scaffold at the tissue defect. A step of closing the periosteum and skin may also be part of the method. During the deposition process of the bio-Ink, the periosteum and skin are to be kept moist in saline.

Scaffolds will structurally and mechanically support the site of implantation while degrading and sustaining ionic Si release and facilitate new bone growth, ingress, and bone union. In certain embodiments where defect scanning prior to live printing is insufficient to adequately resolve the needed scaffold dimensions for scaffold printing, ultrasonic scanning and/or computed tomography scanning and/or digital image scanning may be used. In certain embodiments requiring long-term sustained performance of the scaffold, an amorphous silica or amorphous silicon oxynitride-based nanoparticle device may be utilized that has the potential to sustain the release of ionic silicon and rapidly form hydroxyapatite, especially where a larger defect/fracture is being repaired.

In certain embodiments of the invention where defect curvature disrupts continuous printing of scaffold matrices, scaffold layers may be built in the defect with gelatin-biosilicate nanoparticle slurries to act as a UV absorbing material, clot the blood from the tissue damage site, and the defect leveled to accommodate printing of a scaffold.

Throughout the specification and claims, the following terms take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, the term "or" is an inclusive "or" operator and is equivalent to the term "and/or" unless the context clearly dictates otherwise.

The term "based on" is not exclusive and allows for being based on additional factors not described, unless the context clearly dictates otherwise.

The term "a," "an," and "the" include plural references. Thus, "a" or "an" or "the" can mean one or more than one. For example, "a" cell and/or extracellular vesicle can mean one cell and/or extracellular vesicle or a plurality of cells and/or extracellular vesicles.

The meaning of "in" includes "in" and "on."

As used herein, "bio-Ink" refers to a biocompatible, non-toxic material that comprises a methacrylated gelatin or methacrylated chitosan component and a silicate-based nanoparticle component, that is a liquid like material at a temperature of about 37° C. to about 40° C. and a gel-like material at a temperature of less than about 30° C.

As used herein, the terms "administering", "introducing", "delivering", "placement" and "transplanting" are used interchangeably and refer to the placement of the extracellular vesicles of the technology into a subject by a method or route that results in at least partial localization of the cells and/or extracellular vesicles at a desired site. The cells and/or extracellular vesicles can be administered by any appropriate route that results in delivery to a desired location in the subject where at least a portion of the cells and/or extracellular vesicles retain their therapeutic capabilities. By way of example, a method of administration includes intravenous administration (i.v.).

As used herein, the term "treating" includes reducing or alleviating at least one adverse effect or symptom of a disease, disorder, or defect, such as a bone defect, through introducing in any way a therapeutic composition of the present technology into or onto the body of a subject.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "pharmaceutically acceptable preparation" or "pharmaceutical preparation" refers to a combination of the A1 exosomes, with, as desired, a carrier, inert or active, making the composition especially suitable for diagnostic or therapeutic use in vitro, in vivo, or ex vivo.

As used herein, the teens "pharmaceutically acceptable" or "pharmacologically acceptable" refer to compositions that do not substantially produce adverse reactions, e.g., are not toxic or, or create/induce any allergic, or immunological reactions, when administered to a subject. For example, normal saline and phosphate buffered saline (PBS) are pharmaceutically acceptable carrier solutions.

As used herein, the terms "host", "patient", or "subject" refer to organisms to be treated by the preparations and/or methods of the present technology or to be subject to various tests provided by the technology.

The term "subject" includes animals, preferably mammals, including humans. In some embodiments, the subject is a primate. In other preferred embodiments, the subject is a human.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, the term "or" is an inclusive "or" operator and is equivalent to the term "and/or" unless the context clearly dictates otherwise.

The term "based on" is not exclusive and allows for being based on additional factors not described, unless the context clearly dictates otherwise.

The term "a," "an," and "the" include plural references. Thus, "a" or "an" or "the" can mean one or more than one. For example, "a" cell and/or extracellular vesicle can mean one cell and/or extracellular vesicle or a plurality of cells and/or extracellular vesicles.

The meaning of "in" includes "in" and "on."

As used herein, "stem cell" refers to a multipotent cell with the potential to differentiate into a variety of other cell types (which perform one or more specific functions), and have the ability to self-renew.

As used herein, "adult stem cells" refer to stem cells that are not embryonic stem cells. By way of example, the adult stem cells include mesenchymal stem cells, also referred to as mesenchymal stromal cells or MSC's.

As used herein, the terms "administering", "introducing", "delivering", "placement" and "transplanting" are used interchangeably and refer to the placement of the extracellular vesicles of the technology into a subject by a method or route that results in at least partial localization of the cells and/or extracellular vesicles at a desired site. The cells and/or extracellular vesicles can be administered by any appropriate route that results in delivery to a desired location in the subject where at least a portion of the cells and/or extracellular vesicles retain their therapeutic capabilities. By way of example, a method of administration includes intravenous administration (i.v.).

As used herein, the term "treating" includes reducing or alleviating at least one adverse effect or symptom of a disease or disorder through introducing in any way a therapeutic composition of the present technology into or onto the body of a subject.

As used herein, "therapeutically effective dose" refers to an amount of a therapeutic agent (e.g., sufficient to bring about a beneficial or desired clinical effect). A dose could be administered in one or multiple administrations (e.g., 2, 3, 4, etc.). However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., cells and/or extracellular vesicles as a pharmaceutically acceptable preparation) for aggressive vs. conventional treatment.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "pharmaceutical composition" refers to the combination of an active agent the subcellular vesicles, with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject. For example, normal saline is a pharmaceutically acceptable carrier solution.

As used herein, the terms "host", "patient", or "subject" refer to organisms to be treated by the preparations and/or methods of the present technology or to be subject to various tests provided by the technology.

The term "subject" includes animals, preferably mammals, including humans. In some embodiments, the subject is a primate. In other preferred embodiments, the subject is a human.

The following examples are provided to demonstrate and further illustrate certain preferred embodiments and aspects of the present technology, and they are not to be construed as limiting the scope of the technology. It is specifically intended that the present invention not be limited to the embodiments and illustrations contained herein, but include modified forms of those embodiments including portions of the embodiments and combinations of elements of different embodiments as come within the scope of the following claims.

Example 1—3D Printed Biosilicate Scaffolds

During initial attempts to synthesize porous scaffolds, materials were utilized that resembled the inorganic (synthetic HA) and organic (PLA) matrix for which they were later to be used. These scaffolds were able to promote the ingress of cells into their matrices, however, dense collagen and mineralized matrix formation was not observed within 28 days. Thus the central focus shifted to biosilicate nanoparticles (laponite nano-platelets) to fabricating structurally stable regenerative scaffolds to facilitate bone regeneration, ingress and complete replacement of lost bone.

Biosilicate nano-platelets offer unique advantages including the ability to modify the rheological properties of slurries to control scaffold fabrication during printing and also their afore-mentioned osteoinductive properties for the inorganic component of the scaffold. The inorganic component (biosilicate nanoparticles or laponite, 10-30 nm diameter) and organic component (gelatin methacrylate) were dissolved in sterile saline, centrifugally centrifuged and de-foamed to removed soluble air, and heated in a water bath for 10-20 minutes at 45° C. These solutions were then combined to make slurry as the liquid precursor to 3D printed solid forms. These solvents are used to control the viscosity and evaporation kinetics of the combined slurry during the printing. The slurry is then printed into solid 3D shapes using Robocast Assisted Deposition. Porous scaffolds were designed using CAD-CAM. The robotically controlled nozzle is directed to move in x and y planes within a programmed x-y range. Multiple layers of the scaffold are then extruded in a mesh-like pattern. Scaffolds are printed into 5 mm×3 mm sheets with 1 mm thickness (about 10 layers) (size chosen based on dimensions of rat critical-sized calvarial defects). The mesh center-to-center rod spacing and rod diameter (0.15-0.3 mm) and rod spacing (0.1-0.2 mm) are varied to optimize scaffold porosity and structural stability, which is shown in FIG. 1a. UV light (10-40 mW/cm2) was used to cross-link layers as they are printed and dried onto glass slides. Biosilicate particles were dispersed within the gelatin scaffold (FIG. 1b). FIG. 1c shows a ECM-like surface nanostructure for the scaffold. Scaffold surface chemical coordination analysis by X-ray absorbance near edge structure Spectroscopy (XANES) showed similar surface chemistry as pure $SiO_2$ (model/standard) and $SiONx$ overlays and indicates similar surface reactivity (FIG. 1d).

3-D printed biosilicate nanoparticle-gelatin methacrylate scaffolds were implanted into critical-sized calvarial defects Unfilled defects (no scaffold implant) remained critical sized after 4 weeks (FIG. 3a, less than 10% bone re-growth). Implantation of scaffolds composed of FDA approved materials (polycaprilactone-tri-calcium phosphate (PCL-TCP)) did not show healing and were not fixated in the defect (FIG. 3b).

Upon implantation, laponite-gelatin scaffolds initially induced clotting and were observed to fixate into bone and stimulated healing and ingress of new bone after 4 weeks (~50% of defect was filled with new bone, FIG. 3c). Although these scaffolds showed the potential to rapidly heal bone defects; they degraded too quickly and did not maintain their structure after 4 weeks. This was owed to the low loading rate of laponite nanoparticles (<10%) and the weak gelatin-based scaffolds. Moreover, no antioxidant activity was observed after testing laponite in vitro.

Thus, SiONx nanoparticles improve scaffold strength and stimulate antioxidant activity and further accelerate bone healing versus laponite-gelatin scaffolds (control).

Figure 3:
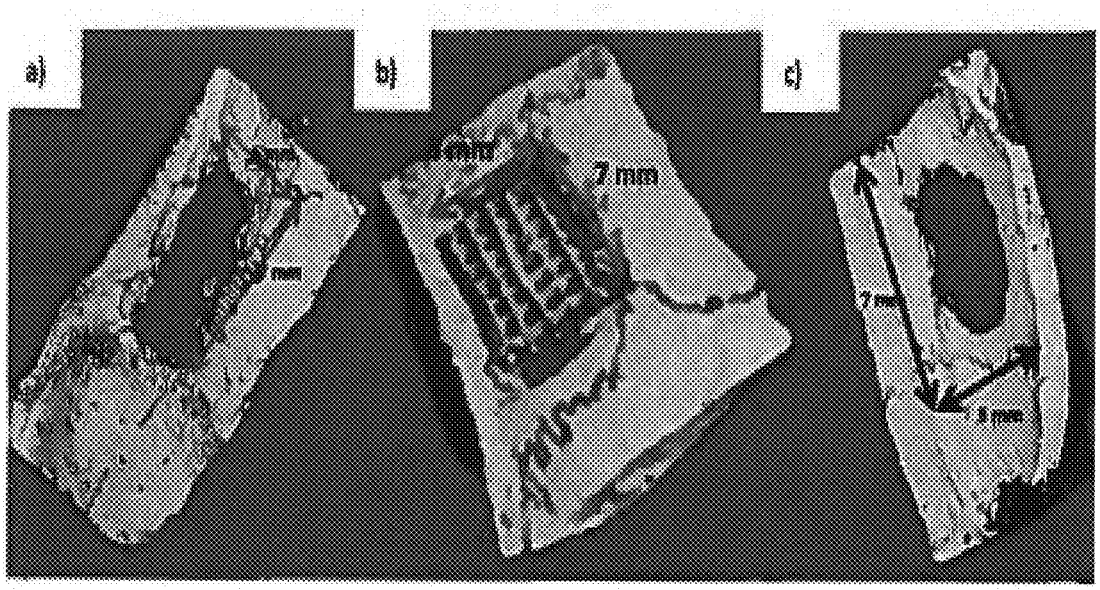
FIG. 3 shows that Biosilica nanoparticle scaffolds enhance healing of calvarial defect. Calvarial defects remain critical sized after 4 weeks (a). Addition of poly caprolactonetri-calcium phosphate scaffolds did not fixate or promote bone healing (b) whereas biosilica nanoparticle-gelatin methacrylate remained fixed in bone and healed ~50% of defect (c)
Figure 4:
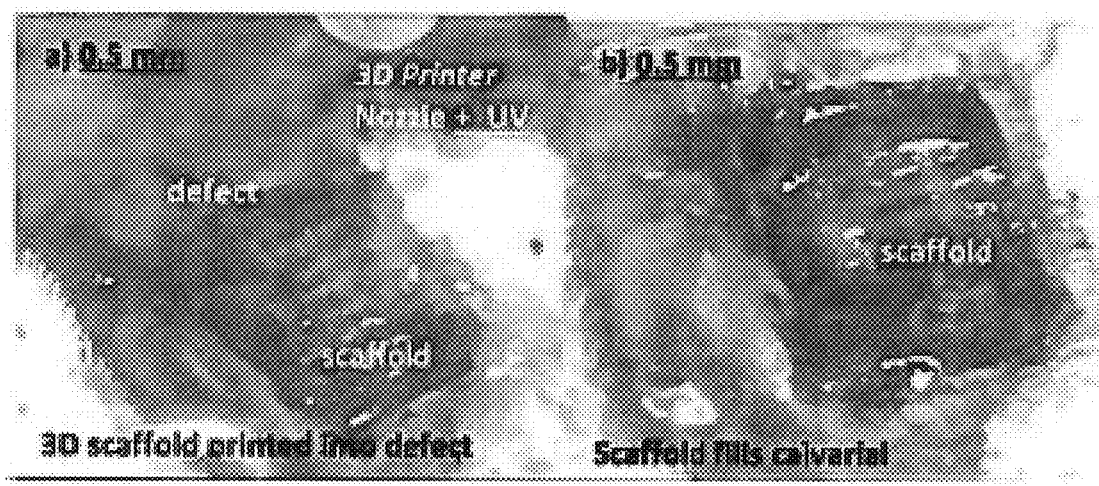
FIG. 4 shows in situ 3D printing method where scaffolds can be fabricated directly into the calvarial defect of an animal subject. Biosilica nanoparticlegelatin methacrylate scaffold was printed directly into anesthetized rats (a). Scaffold printing time was approximately 2 minutes into the 7 mm×5 mm×0.6-0.8 mm deep calvarial bone defect. Scaffolds were printed with in situ low-intensity UV light cure (10-12 mW/sq. em). Scaffolds completely filled defects and maintained their 3D structure (b).
Figure 5:
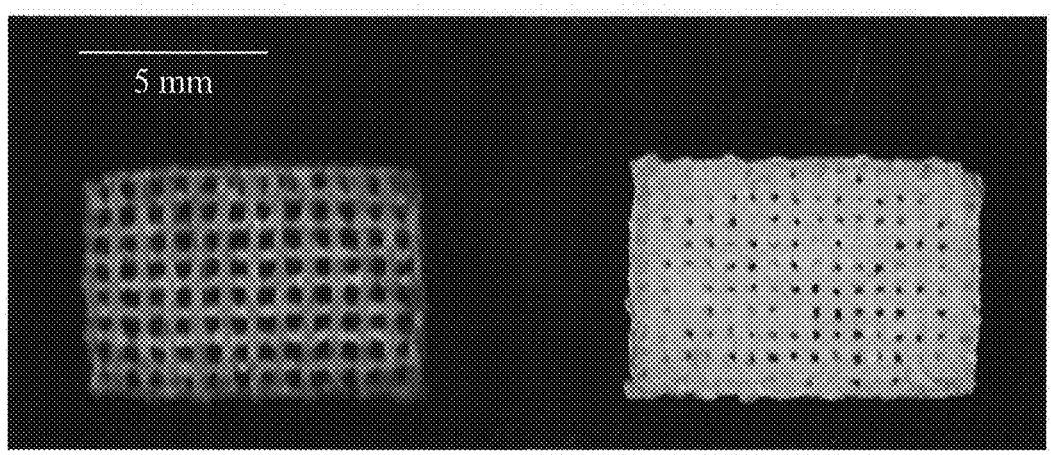
FIG. 5 shows the gross shape of the bio-ink scaffold, 5 mm reference.

As shown in FIG. 4, an in situ 3D printing method where scaffolds can be fabricated directly into the calvarial defect of an animal subject is disclosed. (FIG. 4a). The scaffolds were able to maintain a stable structure and completely fill the defect (FIG. 4b). The animal was observed to have normal behavior and showed no signs of pain on the days following surgery. The scaffolds that were printed into the defect were the same as those a priori printed and then placed (FIG. 3c).

Example 2—In Situ Printing into Calvarial Bone and Bone Defect Repair

The present example demonstrates the utility of the present invention for providing a method for repairing and/or reducing a bone defect in an animal by direct deposit of the reparative, biocompatible materials ("bio-Ink") disclosed herein. The methods are demonstrated to provide high fabrication precision in formation of a tissue scaffold in vivo, the tissue scaffolds being characterized by pores having high resolution definition of between about 0.3 mm to 0.5 mm. The in situ bone tissue repair methods are demonstrated to provide an immediate point of care technique for providing bone repair and/or bone restoration at a defect, thus eliminating and/or reducing the several disadvantages and/or limitations associated with existing bone tissue defect repair methods.

Methodology

Micropatterning and microporosity in the scaffolds provided in the present techniques provide high resolution and precisely sized scaffold structures that facilitate live cell migration and attachment in vivo within a damaged bone tissue site, and are shown here to significantly enhance bone healing rate.

In some embodiments, the in-situ printing technique of a 3-D scaffold into the tissue site of a bone defect in a living animal employs a robotically controlled nozzle-containing device, the nozzle having a needle or needle-like component through which the bio-Ink may be extruded into a defined tissue site. The robotically controlled device is programmed to provide an initial 3-D scanning of the shape of a tissue-site in need of repair, and to create a 3-D scaffold model of the tissue site, using a suitably configured computer software program. The 3-D scaffold model is then used to direct the extrusion and/or injection of the bio-Ink material into the tissue site. This tissue repair process may be employed to deliver treatment to a patient/animal in a single session. Delivery of tissue repair may be provided as part of a surgical procedure where bone is compromised or is found to have a defect during a surgical procedure. Consequently, the need for any secondary surgery event is eliminated.

Material

The bio-Ink of the described in-situ printing (ISP) exists in a liquid-like state upon injection/deposit onto a desired tissue site. The bio-Ink will become more gel-like at the tissue site upon the exposure of the bio-Ink to ultraviolet light. The exposure of the bio-Ink to ultraviolet light, in the presence of a cross-linking agent, results to cross-linking and the formation of filaments in tissue site. Since the bio-Ink is deposited directly into and on living tissue, it is not used with any toxic solvent or together with any solidification process that would compromise a living tissue. For this purpose, natural polymers, such as a gelatin, provides a scaffold of a biodegradable matrix at the tissue site upon deposit of the bio-Ink.

The liquid-like characteristics of the bio-Ink at temperatures between 37° C. to about 40° C. facilitates the deposit/extrusion of the bio-Ink as a series of filaments at the tissue site as part of the present method. The bio-Ink will include a photo-initiator component, and upon exposure to ultraviolet light, will initiate cross-linking within the extruded filaments, and result in the material becoming more gel-like, as the filaments begin to set at the tissue site. In this manner, the filaments do not set and/or turn to gel during the injection/deposition process prior to the cross-linking step. A bio-Ink having the presence of cross-linked filaments would not be suitable for deposit by extrusion/injection, as such would render them incapable of handling the shear stresses exerted during the injection process. The extruded filament(s) as provided in the present methods will have an unsmooth surface and numerous micro-cracks. If the viscosity of the bio-Ink viscosity is too high (i.e., more gel-like), extruded filament would risk breakage into several pieces during the printing process, resulting in a defective scaffold structure at the tissue site.

To improve the printability of bio-ink (reducing gelation and increasing the viscosity of MAG), a sugar, such as sucrose is added to the bio-Ink. Sucrose, or any other sugar, may be used to enhance the "liquid-like state of the bio-Ink by interrupting gelatin gelation through filling the gaps between two polymer chains and weakening polymer chains bonding. This effect makes the bio-Ink take on a more viscous liquid state rather than a gel-like state. Gelation can interrupt extrusion/injection, and therefore, for injecting purposes, a consistency that is or is more similar to a viscose liquid is preferred to gel.

Weaker gelation (such as that resulting from the addition of a sugar/sucrose to the bio-Ink), also permits the formulation of higher gelatin containing bio-Ink preparations. without any compromise on the homogeneity. Higher concentration of gelatin increases available sites of crosslinking and consequently increases the number of cross-links that may be created in the resulting scaffolding structure. However, sucrose effectiveness has an optimum concentration and after this optimum, gelation will increase again. At low concentrations, sucrose and gelatin would not compete for ionic interaction with water molecules. At high concentrations of sucrose, less water is available, and sucrose and gelatin would compete for limited available binding sites on the water molecules. This competition for water results in a tenderness and high gelation behavior of the solution.

Pure gelatin does not possess osteogenic properties. To induce the osteogenic property, gelatin may be composited with silicon-based ceramics. Among these ceramics, LP showed consistent and improved results for healing bone defects in vivo. A MAG-LP composite was therefore prepared and chosen as the base of the bio-Ink deposit method.

Since printing will be performed directly on a live animal's tissue, using organic and toxic solvents can compromise the healing process. Therefore, a system of cross-linking with the lowest possible cytotoxicity is used in the present methods. One cross-linking system with the least cytotoxicity is based on carbon-carbon double bonds opening using free radicals generated by ultra violet (UV) light. C=C does not exist in gelatin, therefore through an addition reaction, methacrylate, which has C=C, was grafted to gelatin and converted to provide the Methacrylated Gelatin (MAG) material of the present bio-Ink preparations.

To initiate the crosslinking reaction, a photo-initiator is used. A photo-initiator is defined as a type of crosslinking agent with a linear molecular structure and two special functional groups at their two ends. These functional groups are unstable, and in the presence of UV light, lose electrons and become free radicals. Free radicals at the two end of a photo-initiator will readily react with two C=C groups from different MAG molecules, and crosslink them together.

There are many different photo-initiators that may be used as part of the present method, and the one selected and used should also have low cytotoxicity. A photo-initiator molecule that may be used in the present methods is 2-hydroxy-1-(4-(hydroxyethoxy)phenyl)-2-methyl-1-propanone, also known as IRGACURE 2959 (12959). This compound has the lowest cytotoxicity among other available photo-cross-linking agents [87]. The photo-initiator will generate radicals and initiate the crosslinking reaction in the presence of 365 nm UV light illumination.

MAG was synthesized and its successful methacrylation reaction was confirmed by Fourier Transform Infrared Spectroscopy (FTIR). Different printing setting was tested to achieve the optimal setting for ISP application. Also, different concentration of sucrose and LP is tested in order to achieve a uniform and stable scaffold. The minimum UV intensity required for complete crosslinking the bio-ink were evaluated. The optimized bio-ink was used for in situ deposit of a tissue repair scaffold in-vivo. The in-vivo studies involved in-situ printing into calvarial bone defects of live rats to evaluate the effect of in-situ printed modified material (bio-ink) on bone healing. Micro-CT, Scanning Electron Microscopy (SEM), Raman Spectroscopy, and histological analysis was done to characterize healing rate, mineral chemistry and structure of regenerated bone.

Materials and Methods

Sterilization Using Ethylene Oxide

Due to the presence of sucrose and gelatin, bio-ink is highly vulnerable to bacterial and fungal growth. Therefore, before preparing bio-Ink, all ingredients were sterilized by ethylene oxide (EtO) for 24 hours and desiccated for an additional 24 hours to remove virtually all residual ethylene oxide. Ethylene oxide is a highly toxic; treated materials should stay in a low-pressure condition after the sterilization process to remove all diffused gas. Ethylene oxide was chosen for sterilization because of its less harsh temperature and pressure requirement relative to other sterilization methods which keep methacrylated Gelatin fairly undamaged [88]. All bio-ink preparation was performed in biosafety cabinet to reduce the chance of any contamination.

In some preparations, the bio-Ink may contain structural material ingredients; ingredients to form a porous, resorbable, matrix; and additives such as, but not limited to, synthetic BMPs, antibiotic chemicals, anti-inflammatory chemicals and radiopaque chemicals, or some combination thereof. The structural material ingredients may, for instance, include a substance such as, but not limited to, Hydroxyapatite, allograft particulate bone, xenograft particulate bone or some combination thereof. The ingredients to form a porous, resorbable matrix may include substances such as, but not limited to, methyl methacrylate, cellulose, resorbable cements, or precursors to resorbable cements or some combination thereof.

The bio-Ink may also include, in some embodiments, an antibiotic or combination of antibiotics. Such antibiotics may include demeclocycline, doxycycline, minocycline, oxytetracycline, tetracycline, thiamphenicol, ciprofloxacin, enoxacin, gatifloxacin, levofloxacin, lomefloxacin, moxifloxacin, nalidixic acid, norfloxacin, ofloxacin, bacitracin, colistin, amoxicillin/clavulanate, ampicillin/sulbactam, piperacillin/tazobactam, ticarcillin/clavulanate, or some combination thereof.

Methacrylated Gelatin Synthesis 0.1 gr/ml powdered cell culture tested gelatin from porcine skin with a Bloom Index of 300 (G1890 Sigma) was mixed with Dulbecco's phosphate buffered saline or DPBS (21-031-CV CORNING cellgro) at 60° C. and stirred for 20 minutes to dissolve gelatin completely. Later on, the temperature was reduced to 50° C. and 0.8 ml Methacrylate Anhydride or MA (276685 ALDRICH) per each gram of gelatin was added to the solution under a continuous stirring condition at a rate of 0.5 mL/min. After adding MA, the solution was kept under the stirring condition for 3 hours. FIG. 3 illustrates the methacrylation reaction.

The solution was transferred to 12-14 kDa dialysis tubes (Spectra/Pore 4, Dialysis Membranes, MWCO 12000 to 14000, Spectrum® Laboratories INC) and dialyzed against ultrapure DI water (MILLIPORE MILLI-Q PLUS ZD5211584) at 18.2Ω. The dialysis system was under a continuous stirring condition for a week at 40° C. to filter unreacted reagents. The water changed every day to maintain osmotic pressure in the system. The purified solution was transferred to freeze-dryer (LABCONCO FreeZone 2.5) and lyophilized for 1 week to isolate Methacrylated gelatin (MAG) and then stored at ~−80° C. to preserve the lyophilized MAG.

After synthesis of each batch, samples were analyzed by FTIR (Thermo SCIENTIFIC NICOLET iS10 SMART iTR) to confirm successful methacrylation.

Fourier Transform Infrared Spectroscopy or FTIR is a chemical analysis method based on energy absorption of covalent bonds in a sample. IR radiation excites covalent bond from a lower vibrational energy to a higher one. This energy can be in a form of vibrational bending, rotating, wagging, stretching, twisting, etc. Each covalent bond can absorb electromagnetic wave at a specific frequency. By monitoring the absorption of IR spectra, covalent bonds in a material can be determined. Note that exact absorption frequency is not possible to be assigned to a covalent bond because each covalent bond can be affected by many factors; these factors include polarity of neighbor bonds, distortion, three-dimensional shape, etc. Therefore, a range of frequencies or wavenumbers is attributed to a covalent bond. Alternatively, molecules can be identified by the whole spectrum of absorption as a fingerprint of that molecule. FTIR absorption data always graphs as a dependent variable for "wavenumber". Wavenumber is a reciprocal of wavelength (wavenumber=1/wavelength).

Adjusting Material and Printing Setting

As mentioned previously, ISP needs both modified ink and adjusted printing setting to become compatible for the unique warm and wet condition of ISP environment (living tissue). Since ISP is a new technique, there is no modified material or printing protocol designed for it. Parameters that can affect printing and needed to be adjusted are printing speed, extrusion speed, materials gelation, trapped air inside the ink, rod-rod distance in the scaffold, Z-distance between each printed 2D layer, and Z-distance from the substrate at printing starting point. Some of these parameters depend on to each other and changing one, need some adjustment on the other. For example, extrusion speed and printing speed a have direct relation; an increase in extrusion speed requires an increase in printing speed to prevent filament distortion. To adjust the MAG-LP composite for ISP, two factors are needed to be considered: temperature and viscosity. The temperature will reduce gelation and viscosity of the ink [89].

Figure 8:
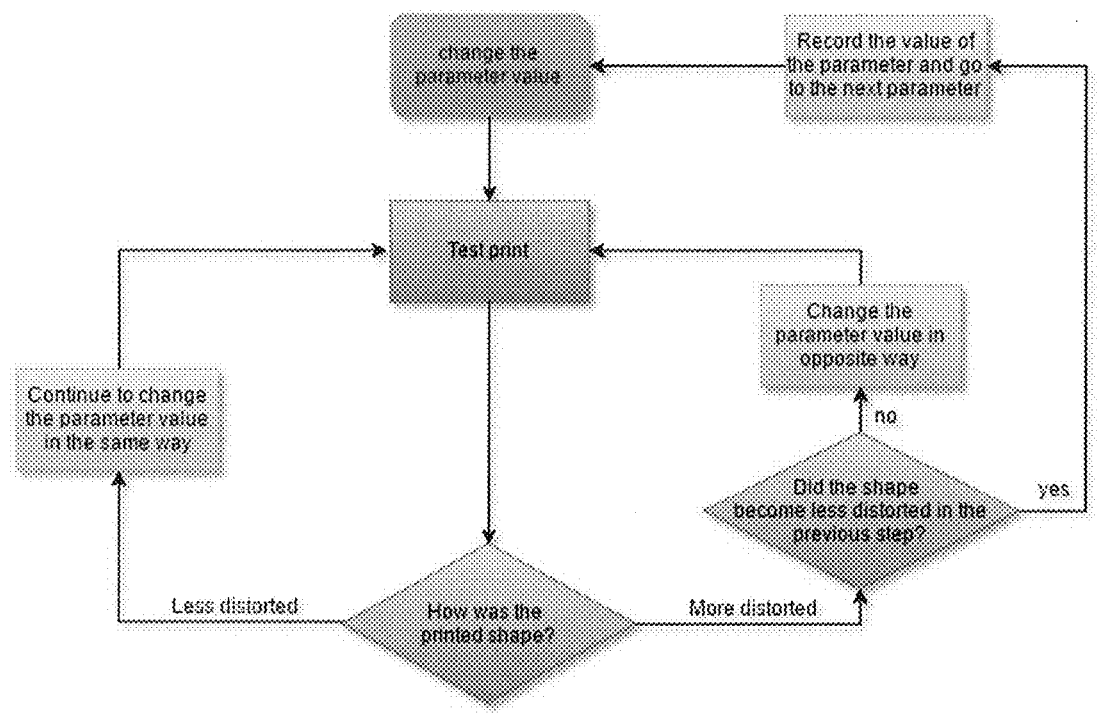
FIG. 8 shows the schematic of the algorithm used for modifying printer values.

To adjust printing setting, the algorithm in FIG. 8 is followed where a parameter was changed while the rest were fixed and the effect on printing was evaluated. Based on these data, a new setting was suggested and tried. If it did not work, the problem was identified and based on that, a new modified setting was suggested.

The filament diameter should be thin enough to make it possible to produce more pores in a unit of volume. However, too thin filament will compromise the scaffold integrity and distort it easily. A 0.2 mm dispenser inner diameter was chosen for this purpose. Ideally, the plunger movement will define the extrusion speed at the tip of the dispenser. By assuming that ink has hydraulic behavior (it cannot be compressed). Volume reduction in the tube resulted from plunger movement should be equal to the volume of extruded filament. This concept can be formulized into the equation below:

$$V_p \times D_t = V_f \times D_f \quad \text{(Equation 1)}$$

Where $V_p$ is the plunger speed, $D_t$ is the dispenser tube diameter, $V_f$ is the filament extrusion speed, and $D_f$ is the filament diameter.

The printing speed should be adjusted according to "filament extrusion speed." Slower printing speed than filament extrusion speed will result in accumulation and distortion of extruded filament and faster printing speed will result in overstretching and tearing of filament.

For material adjustment, scaffolds printed with the reason for increasing LP was because of the constructive effect of LP on the viscosity of the solution that previously discussed in section [00122]. The results are reported as successful or unsuccessful printing and a reason for the unsuccessfulness was provided.

Figure 2:
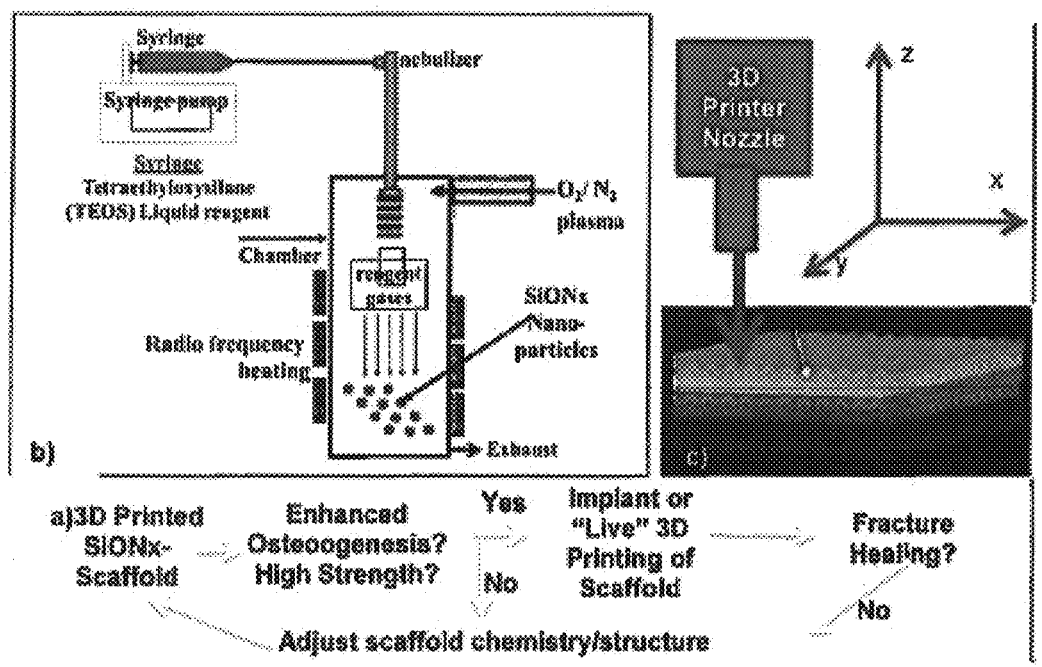
FIG. 2 is shows the overall design of Aim 2 (a). Nanofabrication of biosilica nanoparticles will be conducted using a novel plasma-enhanced chemical vapor condensation (CVC) system (b). The nanoparticles will be embedded into biopolymer scaffolds (gelatin, chitosan) and printed into 30 constructs for direct printing into live rat calvarial defects (c). Schematic flowchart of Aim 2 will be used to test 30 scaffolds and in vitro and in vivo.

Bio-Ink Preparation 0.5% w/w$_{(MAG)}$ I2959 was added to pre-heated DPBS (at 50° C.) and mixed. Next, Lp (Laponite XLG, BYK Additives Inc. Texas, USA) and sucrose (S0389 SIGMA) were gradually added to the solution under continuous stirring condition. Sucrose (Suc) was added in a ratio of 20% w/w$_{(MAG)}$. The solution was stirred at 50° C. for 15 minutes. Afterward, a pre-weighted MAG was added to the solution and transferred to a Planetary Centrifugal Mixer (THINKY ARE-310) and Mixed for 15 minutes at 2000 rpm and defoamed for one minute at 2200 rpm. FIG. 2 shows a schematic process of bio-ink preparation in micro scale. After mixing, the nanocomposite was transferred to a 3 cc UV protected dispenser tube (Nordson EFD Optimum® Light Block AmberBarrels), sealed and centrifuged for one minute at 4.4 krpm to remove all the air trapped inside the ink. This is a very crucial step; if the syringe is not properly de-bubbled, the continuous material injection in robocaster will be interrupted, the filament will rupture and the whole scaffold will distort.

Minimum UV Intensity for Bio-Ink Cross-Linking

The cross-linking process is initiated by UV light and the degree of crosslinking has a direct relation with UV light intensity [90]. To determine the optimum UV light intensity, scaffolds with dimensions of 6×8×6 mm were printed (The average weight of scaffolds at this size was measured 0.10 gr<x<0.15 gr) with a printing speed of 9 mm/min. While printing, injected material were exposed to UV spotlight right at the tip of the printer's nozzle (THORLAB CS2010). Five groups were designated and each group was treated with a different light intensity (5, 10, 20, 30, 40 mW/cm$^2$). After printing, samples were transferred to wells filled with 4 ml PBS and incubated at 37° C. During incubation, scaffolds were monitored for any sign of dissolution and degradation. The degradation rate of Bio-ink is directly related to the degree of cross-linkage [90]. At 37° C., up to 5% wt. gelatin can readily be dissolved in water without creating a gel [91]. Therefore, to eliminate the effect of gelation on the test, the total weight of scaffold in the media keep below 5% of the PBS. As a result, each scaffold was incubated in 4 ml PBS.

To run the test, a bio-ink is selected that can be dissolved fairly fast in uncrosslinked state. Therefore, it can make scaffolds gross changes easier to track and also contain all the ingredients of bio-ink. Since the dissolution of bio-inks with a higher concentration of MAG or LP usually increases the viscosity of the solution and slow down further dissolution, a composition with a lower concentration of MAG and LP was more proper for this test. As a result, a 2-10 bio-ink (2% LP, 10% MAG, 2% Suc, 0.05% 12959) was selected for this test.

Partial Removal of Rat's Calvarial Bone

Defects with dimensions of 4±1 mm by 6±1 mm was created on the right side of the sagittal suture on a rat's calvarium according to the IUCUC approved protocol #2014-0153. The procedure is explained below.

The rat was anesthetized with 5% isoflurane (Henry Schein) with a flow rate of 4-5 L/min until breathing speed dropped to about half. Then, the rat's head was shaved from caudal end of the skull to the bridge between two eyes. Later on, its head was fixed on a stereotaxic device and an oximeter/heart rate monitor clip attached to its leg. Afterward, the isoflurane concentration reduced to 1-2% and delivered to the rat through a nasal mask. The rat's heart rate was constantly monitor and kept between 225-300 bpm.

Figure 9:
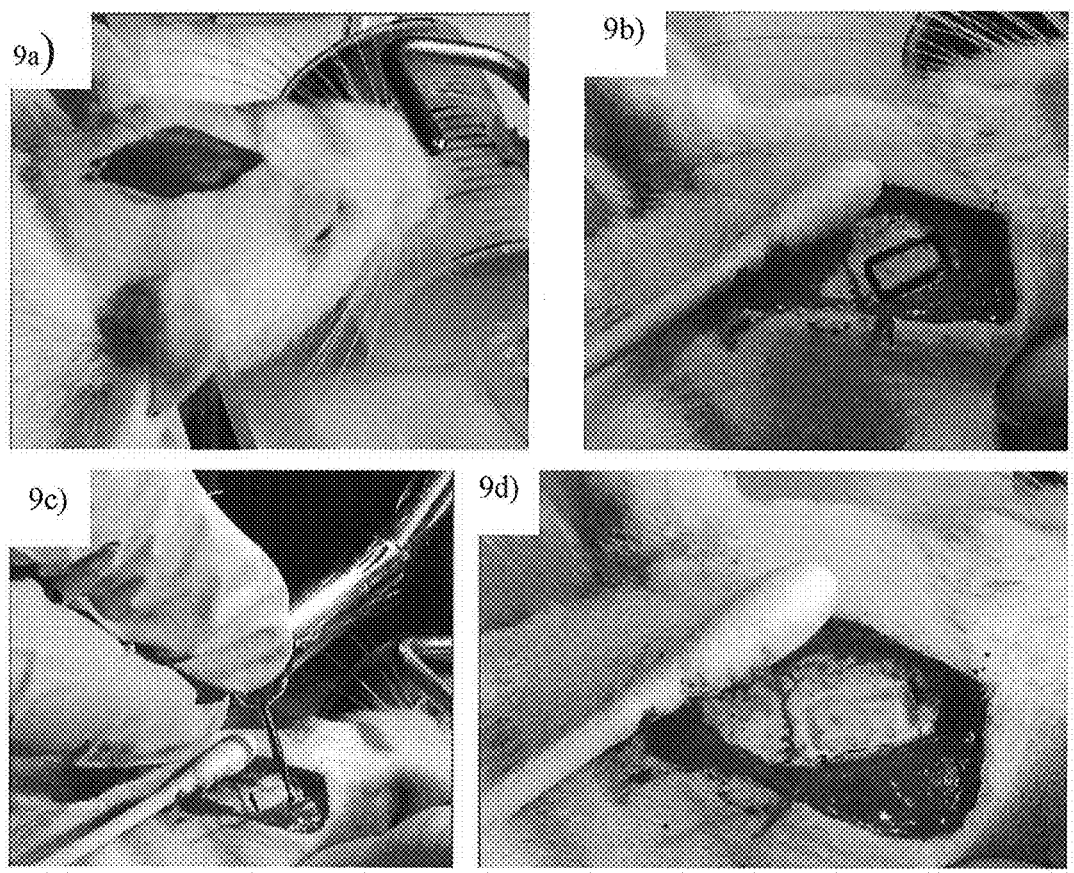
FIG. 9 shows creation of defect in a rat's calvarium.
Figure 10:
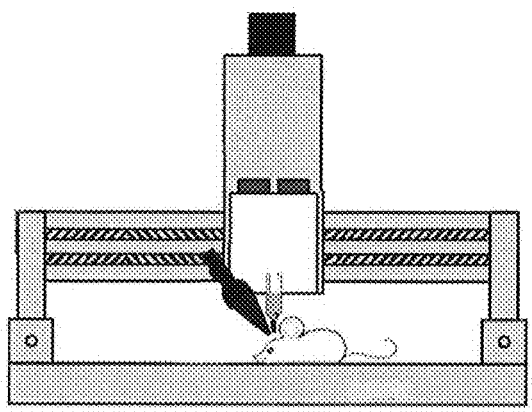
FIG. 10 shows (a) the schematic shape of in-situ printing, a UV spotlight is continuously cross-linking scaffolds as they extruded out. (b) the process of recording the coordination and the shape of a defect (calibration) by hitting bone's wall and recording their relative position. (c) in-situ printing in progress (the bright blue light is the UV spotlight illumination at the tip of the dispenser. This spotlight had a diameter of 2 mm) (3) the final outcome of in-situ printing before suturing the incision.
Figure 10:
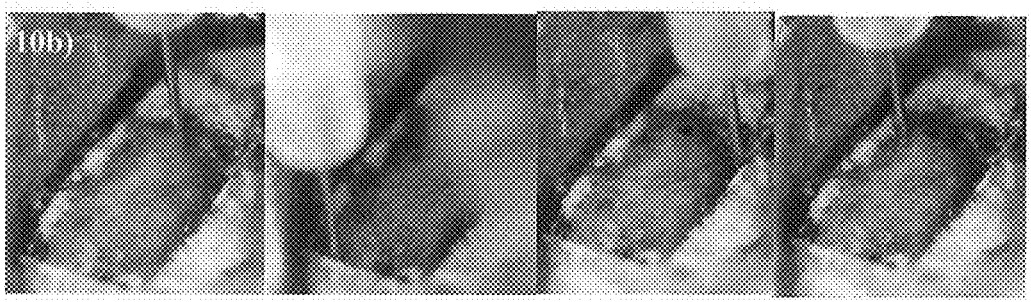
Figure 10:
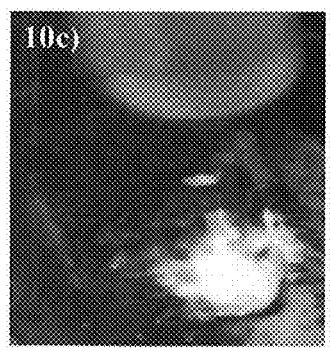
Figure 10:
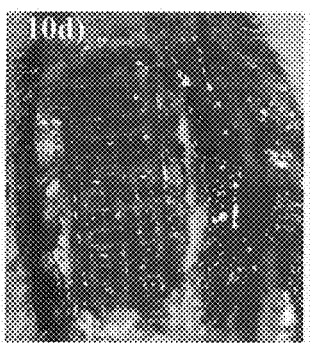

A 1.5 cm sagittal incision from forehead to the caudal end of the skull was created by scalpel blade #15 and the periosteum layer was scratched away to expose the bone. The bone was irrigated by sterile saline solution and then dried by sterile gauze and air blowing. Defect's boundaries were drawn on calvarium using a sharpie and a template. Later on, the bone was gradually cut using high-speed dental handpiece with #1 Round Carbide dental burr. The cutting was continued until a pinkness become visible on drilling lines. A forceps was used as a leverage to lift the bone. FIG. 9 shows the process of cutting the bone. Later on, the exposed dura was cleaned and dried. This bone cutting process is very delicate and the burr can damage the dura if it passes all the way through the bone. Damage to the dura may cause some serious damage to the rat's brain and/or bone healing process.

In-Situ Printing

The bio-ink filled dispenser tube was installed on the 3D printer and a gauge 30 (0.2 mm) dispenser tip was attached to it. Afterward, the rat was transferred to the printing area of the robocasting machine.

The printer's probe was brought lower along Z-axis of the printer (height) until dispenser tip touched the dura on the lateral side of the defect and the coordination was recorded. This step was repeated on the medial, rostral and caudal sides of the defect. If these measurements showed that dura is not horizontal and is tilted, the stereotaxic device was adjusted accordingly to make the dura's plane horizontal. By this action, the Z-axis coordination of dura also was achieved. The shape, position, and size of the defect are recorded by moving the dispenser tip along Y- and X-axis of the printer and touching side walls of the defect and recording coordination. The thickness of the bone was measured by subtracting the coordination of the top surface of the bone and the surface of the dura.

Based on recorded coordination, a suitable shape for a scaffold was designed. The scaffold was designed 0.2-0.4 mm smaller in length and width to give the printed scaffold a margin of 0.1 to 0.2 mm from each side of the defect. Printing setting was set for a printing speed of 9 mm/s, pore size (rod to rod distance) of 0.65 mm, and layer deposition with a thickness of 0.15 mm. The number of required layers was calculated by dividing the bone thickness to each depositing layer thickness (thickness of bone (mm)/0.15). A margin of 0.1 to 0.2 mm was considered for scaffold swelling after absorbing blood and serum in the periphery. The printing speed was adjusted based on the viscosity of the bio-ink and the speed that the material extruded out from the dispenser tip. This number determined experimentally according to section [00142]. As it discussed before, the optimum pore size of scaffold for cell migration is 0.5 mm. The printing filament had a thickness of 0.2-0.15 mm. Therefore, a rod-rod distance of 0.65 mm would give us a pore size of close to 0.5 mm. Starting position of printing was determined in a way that the dispenser tip was 0.15 mm above the dura. This distance is designated for the first depositing layer.

To verify the printing process and the pressure inside the dispenser, a test print on a sterile, flat surface was performed. The 365 nm UV spotlight with a diameter of 2 mm was adjusted to directly illuminate the tip of the dispenser with an intensity of 31 mW/cm$^2$ to crosslink material as it extruded out. After checking all parameters and coordination, in-situ printing started. When in-situ printing is finished, the printed scaffold was irrigated by PBS to wash all unreacted reagents. Later, the flapped skin was sutured with 4-0 braided silk suture and the incision area cleaned by saline and sterile gauze. On that time, isoflurane concentration reduced to zero. When animal's heart beat started to increase, a 0.1 ml of painkiller (nalbuphine) was injected intramuscularly.

If for any reason printing was not successful, it was immediately stopped, the defect cleaned by a sterile gauze, dried by air, and the printing was repeated.

To evaluate the effect of bio-ink and in-situ printing, six different treatment for healing rats' calvarial bone defect were implemented: empty defect or no treatment (served as control), implantation of pre-fabricated bio-ink of 2-10 (current conventional implantation method served as a treatment control), implantation of pre-fabricated FDA approved 30% PCL-70% TCP composite hybrid, in-situ printing of the 2-10 bio-ink and in-situ printing of a 4-10 bio-ink (4% LP, 10% MAG, 2% Suc, 0.05% I2959). All treatments were done in triplicates. 4 weeks after surgeries, calvarial bones were harvested.

Scanning Electron Microscopy

Scanning electron microscopy (SEM) is a microscopy technique that uses high voltage electron beam instead of an electromagnetic wave to detect objects. SEM scans an object with a focused beam of electron and produces images. When electrons hit the sample they either reflect or scatter. Also, they can knock out an electron from sample's atom. By collecting these electrons using a different detector, different information about specimens can be generated including surface topography and surface chemistry.

Secondary Electron Imaging (SEI) detector collects knocked out electrons from a specimen's surface. These electrons gained momentum from a non-elastic interaction between emitted electron and electron form molecule's K-shell or L-shell. As a result, secondary electrons do not have a high energy and cannot pass through the specimen unless these secondary electrons are very close to the surface. The number of escaped SE depends on the angle of the electron beam with the specimen's surface. Collection and translation of these SEs can provide a high-resolution image (up to 1 nm, depend on the sensor) from the surface of a sample. Due to nature of SEI, acquired imaged have a high depth of focused field and make it a powerful technique to take images from rough or uneven surfaces in high magnifications.

Backscattered Electrons (BSE) detector collects electrons that scattered from the surface of a sample after being shot by an electron gun. This scattering phenomenon resulted from an elastic collision between emitted electron and atoms of the sample. Heavier atoms are bigger and therefore can scatter more electrons, versus small atoms that scatter less number of electrons. This phenomenon makes it possible to identify atoms and acquire topographical and chemical information from the surface of the sample.

Energy-dispersive X-ray spectroscopy (EDS) is another detector that usually are available in SEM microscopes. When electrons from SEM's electron gun hit the target atom, if the electron energy is high enough it can knock out an electron from inner shells and create an "electron hole." The electron hole will be replaced by an electron from a higher shell which has higher energy. This difference in energy will generate a characteristic X-ray that is unique to that element. By collecting these X-ray beams the element at radiated point can be detected. Mapping elements distribution on the surface is also possible by using scanning electron beam.

SEM rely on electron beams. Therefore to get a reliable and strong electron beam and reduce air interference, the imaging should be done in a vacuum. Furthermore, since high-density electron beam is shooting toward the surface, the surface should be conductive to transfer trapped electrons to the earth. Biological samples are often prone to vacuum and usually are not conductive. Therefore using SEM for these samples could be challenging. To solve this problem, samples usually become fixated, dehydrated and coated with an electron conductor material to protect their structure and also make them conductive.

There are many electron conductor materials that can be used for coating but the most common ones are carbon and gold. The type of coating material is important when EDS analysis is desired. EDS will capture some signals from the coating material along with signals from the specimen. Therefore, the coating material can interference with the result and generates some artifacts. Carbon coating is usually an effective solution for this problem. Unlike gold it has a low atomic number and does not add unwanted peaks to the X-ray spectrum.

In this study, BSE (at 20 kV) and EDS were used to analyze the chemical composition of scaffolds and dissected bone. The SEM machine used for these tests was JEOL-JSM-6010LA (USA, Peabody, Mass.) and carbon used for coating samples.

Micro-Computed Tomography

X-ray scanning is a well-known technique that is used in the diagnosis of hard tissue trauma and pathology. A modified version of X-ray scanning is Computed Tomography (CT) scanning. This technique creates a 3D image from a hard tissue by taking multiple sections of x-ray scans and combining them which can provide more information. This technique also is used by scientist and a standard method of collecting μCT results developed for that reason [93]. Micro-computed tomography or "μCT" is similar to clinically used CT scans, but on a smaller scale and significantly higher resolution. High resolution of these machines technically made them a 3D microscopy technique for radio-opaque materials.

In this study μCT scanning was done on harvested calvaria to analyze the amount of regenerated bone and also the pattern of healing in the region, All μCT works were done using the Scanco Medical 3.5 μCT.

Raman Spectroscopy

Raman was done on calvaria samples to evaluate the quality and chemistry of regenerated bone and also to provide a better understanding of the healing pattern and fate of the scaffold in the defect. Four different spots around remineralization front (RMF): surrounding bone (SB), remineralized tissue, RMF, and fibrous tissue were analyzed. These data then compared with the data from crosslinked bio-ink.

Raman Spectroscopy is a material characterization method that can characterize functional group and chemical structure of a material. The advantages of this technique over FTIR is that there is no interference between water (OH peak) and other functional groups. This feature makes Raman very attractive for organic tissue characterization since they usually contain a high portion of water and molecules with many —OH groups. Recently, this technique gains a lot of attention among bone biologist as a technique to characterize bone composition [94], evaluate bone maturity, and quantify re-mineralization [95, 96]. Previous studies showed that mature bone in mouse and other rodents has characteristic Raman spectrum [94]. In this spectrum, there is a band at around 960 cm$^{-1}$ which is related to phosphate. There are also Amide I and amide III bands that represent organic components of bone and are located at 1660 cm$^{-1}$ and 1242 cm$^{-1}$ respectively. The intensity ratio of amide I or amide III to primary phosphate band represents the organic to mineral ratio (degree of mineralization) in the bone.

Histology

Histology or "microanatomy" is the study of the biological microstructures from tissues to cells. This is a very powerful technique to study tissue structure, development, and also for diagnostic purposes. Malignant tumors, microbial infection, osteoarthritis, autoimmune disease, and necrotic tissue, all cannot be recognized without the histological examination [12].

To see biological specimen under a microscope, they need to be "fixed." Fixation process stops all cells metabolic activities and stabilizes proteins of the cell and/or tissue by cross-linking them. This process eventually hardens a tissue and preserve its microstructure. Fixation also, inactivates autolytic enzymes, bacteria, and fungi.

Bright field microscopy is the most common way to study histological structure. For that reason, samples should cut thin enough to let the light pass through it. However, tissue structure still is not hard enough and the sectioning process will disrupt their structure. To make tissue stronger, the water inside will be changed by a harder yet diffusible media like pure paraffin or plastic. Since water is not miscible with embedding medium, it will be replaced by ethanol first through a process called "dehydration." Ethanol also is not miscible with embedding medium and will be replaced by xylol in "clearing" process. Later on, xylol replaced with paraffin in "infiltration" step and tissue get hardened. Afterward, tissue will be embedded in paraffin or plastic and sectioned in 5-15 μm thickness. This process will be done by "Microtome." At this thickness, most of the structure either is transparent or so dim in colors that make them hard to be identified. Therefore, staining is required to color different region of tissue. Each type of staining dyes binds to a specific region of tissue based on their unique chemical features and color them. This will make the histological section easier to analyze. For staining with water soluble dyes, sections will undergo "rehydration" process which essentially is the reverse of infiltration, clearing, and dehydration process.

For the purpose of this study, dissected calvaria were cut in coronal section and stained with Hematoxylin and Eosin (H&E) and Stevenel's Blue stain and Van Gieson Picro-Fuchsin counterstain (or in short, Stevenel's Blue). H&E is the most common histological stain.

Hematoxylin has blue/purple color and binds to basophilic components like nucleic acids. Eosin has red color and binds to acidophilic components like proteins. Stevenel's Blue stains connective/fibrous tissue blue-green and osteoid light green. Van Gieson counterstain stains bone sharp red.

Fourier Transform Infrared Spectroscopy

Figure 11:
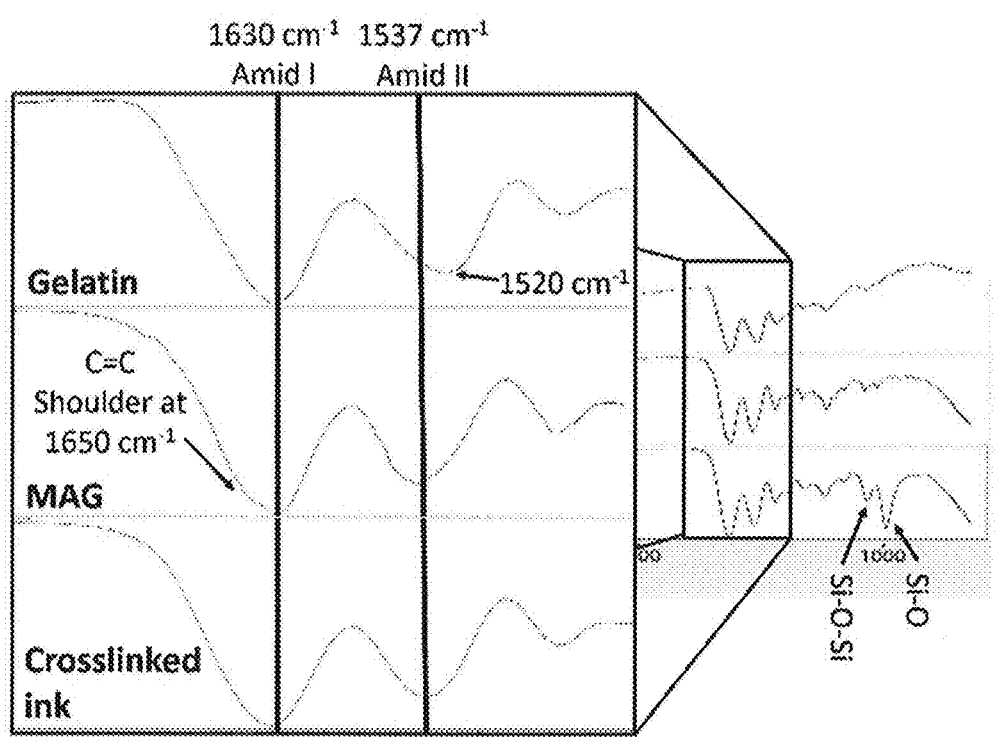
FIG. 11 shows FTIR Spectroscopy from gelatin, MAG and crosslinked bio-ink.

FIG. 11 shows the FTIR results from the synthesized MAG, Gelatin and crosslinked bio-Ink. This figure showed amide I peak at 1630 cm$^{-1}$ and amide II at 1520 cm$^{-1}$ in the gelatin spectrum. These amide peaks can be found in a collagen (gelatin) structure [97]. In the synthesized material spectrum, amide II peak shifts toward 1537 cm$^{-1}$. In the synthesized MAG spectrum, a shoulder at ~1650 cm$^{-1}$ is visible which was not detected in the crosslinked Ink spectrum. The spikes at 990 cm$^{-1}$ and 1068 cm$^{-1}$ are known as signals for Si—O ad Si—O—Si respectively [98].

Adjusting Material and Printing Setting

The optimum setting and material composition for ISP was achieved by evaluating different setting through many trials. The summary of all attempts are listed in Table 1, Table 2, Table 3, Table 4 and Table 5. For each setting, a set of 10 to 15 attempts was done. For each attempt, scaffold's shape was different (cylinder, cubic, and rectangular prism with different dimensions). If all attempts failed, the result recorded as unsuccessful printing. If more than one attempts but not all succeeded, the result recorded as successful printing but with low consistency. If all attempts were successful, the result recorded as successful printing.

TABLE 1

Attempts to adjust the centrifuge speed and duration to remove the trapped air in the ink
Centrifuging to remove trapped bubble

| | Successful printing | If no, reason | Suggestion |
|---|---|---|---|
| 1 Krpm for 1 min | No | Trapped bubble caused segmented extrusion | Using higher centripetal forces or longer centrifuge time |
| 1 Krpm for 2 min | No | Trapped bubble caused segmented extrusion | Using higher centripetal forces or longer centrifuge time |
| 1 Krpm for 5 min | No | Trapped bubble caused segmented extrusion | Using higher centripetal forces or longer centrifuge time |
| 2 Krpm for 5 min | No | Trapped bubble caused segmented extrusion | Using higher centripetal forces or longer centrifuge time |
| 3 Krpm for 5 min | No | Trapped bubble caused segmented extrusion | Using higher centripetal forces or longer centrifuge time |
| 4.4 Krpm for 5 min | No | Trapped bubble caused segmented extrusion | Reduce centrifuge time |
| 4.4 Krpm for 2 min | Yes | N/A | N/A |
| 4.4 Krpm for 1 min | Yes | N/A | N/A |

De-bubbling, plunger speed, and printing speed trials were done on all four different compositions to evaluate the optimum setting for each (if it was possible to find). All four composition behaved similarly in these attempts.

TABLE 2

Attempts to adjust bio-ink composition for the most reliable printing Composition

| | Successful printing | If no, reason | Suggestion |
|---|---|---|---|
| No Suc, 2% LP (0.3 mm pore size) | No | Filaments fused in each other | Increase viscosity by increasing LP conc. |
| No Suc, 2% LP (0.5 mm pore size) | Yes, but not consistent | In some areas, filaments fused in each other | Increase viscosity by increasing LP conc. |
| 20% Suc, 2% LP (0.3 mm pore size) | No | In some areas, filaments fused in each other | Increase viscosity by increasing LP conc. |
| 20% Suc, 2% LP (0.5 mm pore size) | Yes, but not consistent | In some areas, filaments fused in each other | Increase viscosity by increasing LP conc. |
| No suc, 4% LP (0.3 mm pore size) | Yes, but not consistent | There were many failed printing (occasionally the filament was segmented) | Reduce gel strength by adding sucrose |
| No suc, 4% LP (0.5 mm pore size) | Yes, but not consistent | There were many failed printing (occasionally the filament was segmented) | Reduce gel strength by adding sucrose |
| 20% Suc, 4% LP (0.3 mm pore size) | Yes | N/A | N/A |
| 20% Suc, 4% LP (0.5 mm pore size) | Yes | N/A | N/A |

It is noted that higher concentrations of MAG and LP that were used in next chapter also went through printer speed trial, and the 6-20 bio-ink (6% LP, 20% MAG, 4% Suc, 0.1% Photo-initiator agent (I2959) was determined to have the optimum printing speed of 6 mm/min. Other of the bio-Inks tested here had successful printings using the chosen setting presented here.

TABLE 3

Attempts to evaluate the optimum distance between substrate and dispenser tip

Z-distance from the substrate at printing starting point

| Tip and substrate distance | Successful printing | If no, reason | Suggestion |
|---|---|---|---|
| Touching the substrate | No | The material was not extruded. A pressure built up and a burst extrusion happened in the second layer. | Increase the distance |
| 0.1 mm | Yes but the first layer was distorted | Filaments of the first layer were flattened and merged. Other layers were printed with no problem | Increase the distance |
| 0.15 mm | Yes | N/A | N/A |
| 0.2 mm | No | The filament did not stay on to the substrate and moved as printer moved | Decrease the distance |

Z-distance between each printed 2D layer

| Average distance between layer | Successful printing | If no, reason | Suggestion |
|---|---|---|---|
| 0.2 | No | Filaments cannot stick to bottom layers | Increase the distance between layers |
| 0.15 | Yes | N/A | N/A |
| 0.1 | Yes, but resolution was reduced | The filament slightly flattened that caused a reduction in pore size | Decrease the distance between layers |

TABLE 4

Attempts to modify plunger speed
Plunger speed

| plunger speed | successful printing | If no, reason | Suggestion |
|---|---|---|---|
| 0.5 mm/min | No | After a few layer, a built up pressure ejected the dispenser tip | Reduce the plunger speed |
| 0.4 mm/min | No | After a few layer, the material leaked out from the sides of the dispenser tip | Reduce the plunger speed |
| 0.3 mm/min | Yes | N/A | N/A |
| 0.2 mm/min | No | The extrusion speed was too slow | Increase the plunger speed |
| 0.1 mm/min | No | Ink did not extrude out in the entire printing process | Increase the plunger speed |

TABLE 5

Attempts to adjust printing speed for the most replicable results
Printer speed at plunger speed of 0.3 mm/min

| Printing speed | Successful printing | If no, reason | Suggestion |
|---|---|---|---|
| 14.75 mm/min | No | The filament stretched and broke | Reduce the printing speed |
| 12 mm/min | No | The filament stretched and broke | Reduce the printing speed |
| 10 mm/min | Yes, but not consistent | There were some occasional segmentations | Reduce the printing speed |
| 9 mm/min | Yes | N/A | N/A |
| 8 mm/min | No | Couldn't print straight filaments | Increase the printing speed |

The most consistent and successful result was for a bio-ink with 20% w/w$_{gelatin}$ Sucrose and 4% wt. LP, centrifuging with 4.4 Krmp for 1 minute, dispenser tip to substrate distance of 0.15 mm, plunger speed of 0.3 mm, and printing speed of 9 mm/min.

Minimum UV Intensity for Bio-Ink Crosslinking

Figure 12:
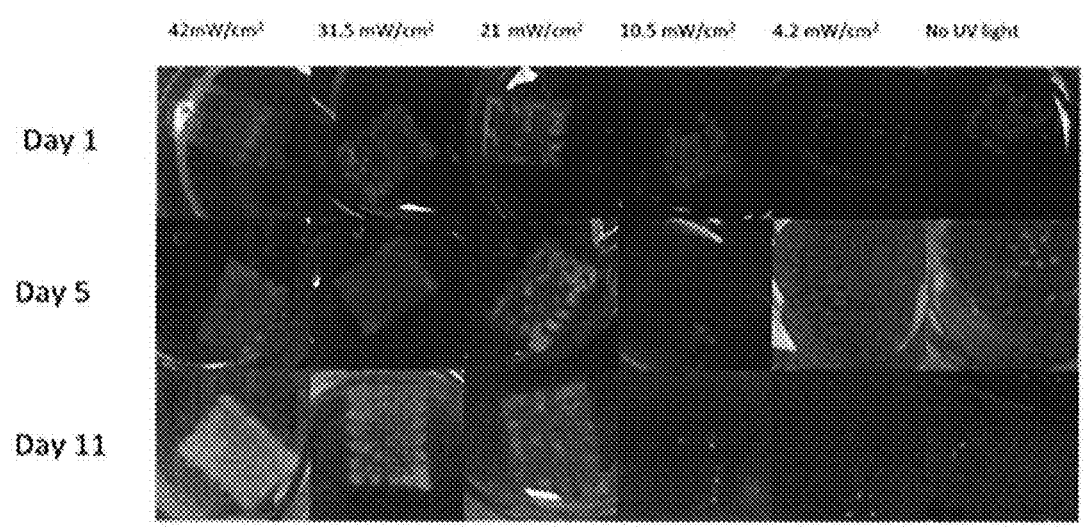
FIG. 12 shows effect of real-time UV illumination intensity on Bio-ink solubility.

Cross-linking test on bio-ink revealed that as UV intensity increases, the scaffold can hold its integrity for a longer time. FIG. 12 shows that scaffolds crosslinked with light intensity below 21 mW/cm$^2$ completely dissolved in PBS in less than five days. The scaffold cross-linked by 21 mW/cm$^2$ also shows some signs of deformity and hyper-swelling. Scaffolds crosslinked by 31.5 and 42 mW/cm$^2$ stayed intact in the environment for 11 days. Note that there is a color difference between scaffolds crosslinked with UV intensity above 21 mW/cm$^2$ and those crosslinked with lower intensity.

Scanning Electron Microscopy

Figure 13:
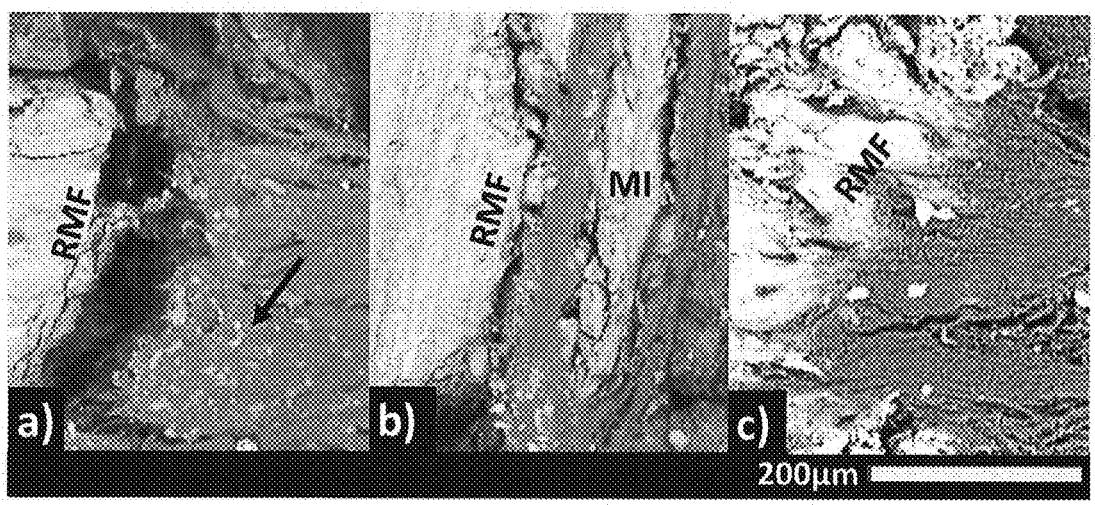
FIG. 13 shows backscattered Scanning Electron Microscopy (BS-SEM) from a coronal section of the defect shows the area around remineralization front (RMF).

Backscatter SEM images from a coronal section of the defect are shown in FIG. 13. Dark areas belong to elements with a low atomic number (like carbohydrates). Bright areas are belong to elements with a relatively higher atomic number like inorganic atoms (Ca, P). There are some bright dots in the dark region (arrowhead in FIG. 13) and also some islands composed of heavier atoms (FIG. 13.b). Also, in FIG. 13.c heavy elements and light elements are seems to diffuse in each other and there is not a clear boundary.

Figure 14:
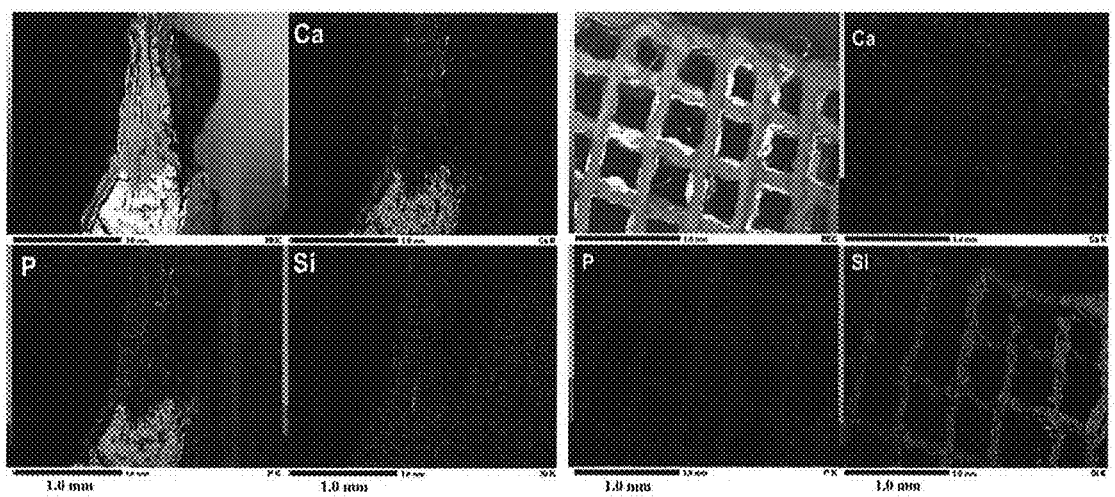
FIG. 14 shows (left) EDS analysis from a coronal section of a harvested calvarium. This mapping was done 4 weeks after in-situ printing of the 4-10 bio-ink and showed Ca and P in regenerated hard tissue and no detectable amount of Si in both hard and fibrous region. (Region) EDS analysis of crosslinked bio-ink scaffold showed the presence of Si all over the scaffold and no Ca and P.

EDS mapping analysis from a coronal section of harvested calvaria showed that the defect is not fully healed (FIG. 14 left). It also showed that hard regenerated tissue contains calcium and phosphorous. Note that the scaffold did not contain either Ca or P (FIG. 14 right). It also showed that there is no Si trace in either regenerated or fibrous region of defect (FIG. 14 left). However, the scaffold itself contain a detectable amount of Si (FIG. 14 right).

Micro-Computed Tomography

Figure 15:
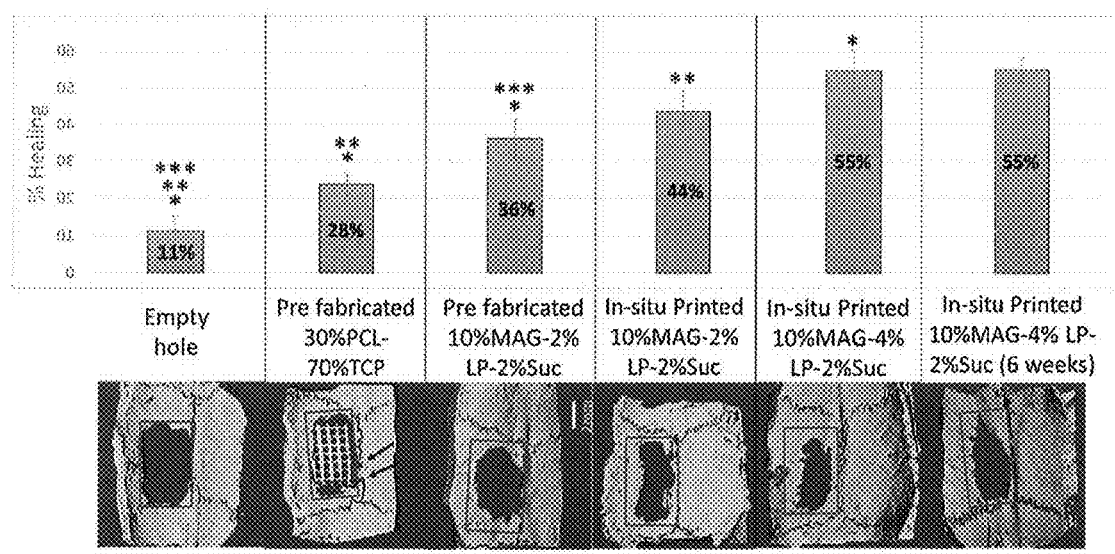
FIG. 15 shows Micro-CT images from six different treatment and their corresponded healing percentage (n=3).

Micro-CT imaging from calvarial bones (FIG. 15) showed that empty hole treatment only exhibits 11% remineralization in 4 weeks that was the lowest healing rate among all treatment (P<0.05) but not have any significant difference with Pre-fabricated 30% PCL-70% TCP composite. This PCL-TCP composite despite causing some minor healing, showed signs of bone resorption in defect site (arrows FIG. 15). On the other hand, the pre-fabricated 2-10 bio-ink showed an increase in remineralization and in 4 weeks versus empty-hole treatment (P<0.05). Furthermore, in-situ printed scaffolds with the same bio-ink composition of 2-10 showed near 44% improvement in bone healing that was higher than PCL-TCP treatment. In another treatment, scaffolds with the in-situ printing of the same bio-ink but with doubled concentration of LP (4-10) has been used and it was able to heal more than the pre-fabricated 2-10, PCL-TCP, and empty hole. The same treatment was used for the last group but calvaria were harvested 6 weeks after the surgery. It was shown that there is no difference in healing between 4 and 6 weeks.

Raman Spectroscopy

Figure 16:
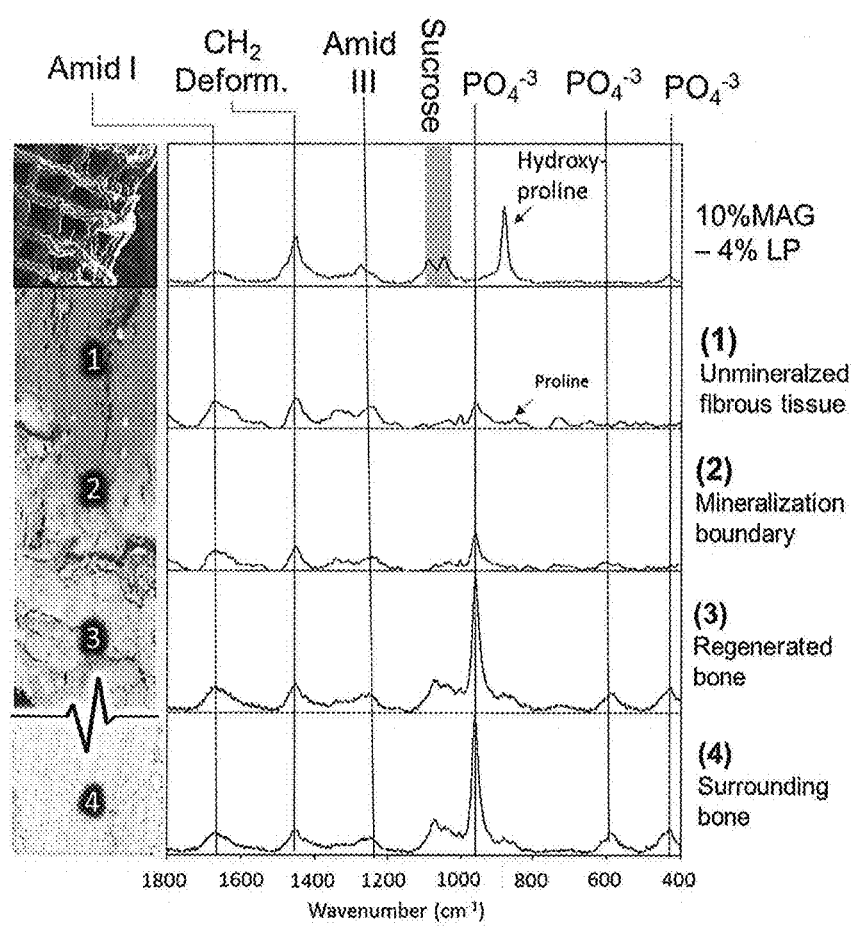
FIG. 16 shows Raman Spectroscopy from the crosslinked 4-10 scaffolds and four different regions around RMF.

Raman spectroscopy showed that bio-ink had two characteristic bands of sucrose and sharp hydroxyproline peak (FIG. 16) that were not found in any region of calvarial bones. Moving from fibrous tissue in the middle of the bone defect toward surrounding bone, PO$_4$ band intensity increases and also PO$_4$ band intensity relative to amide peaks increased in a similar fashion (FIG. 16). Finally, Raman spectrum of the regenerated mineral is identical to surrounding endogenous bone.

Histology

Figure 17:
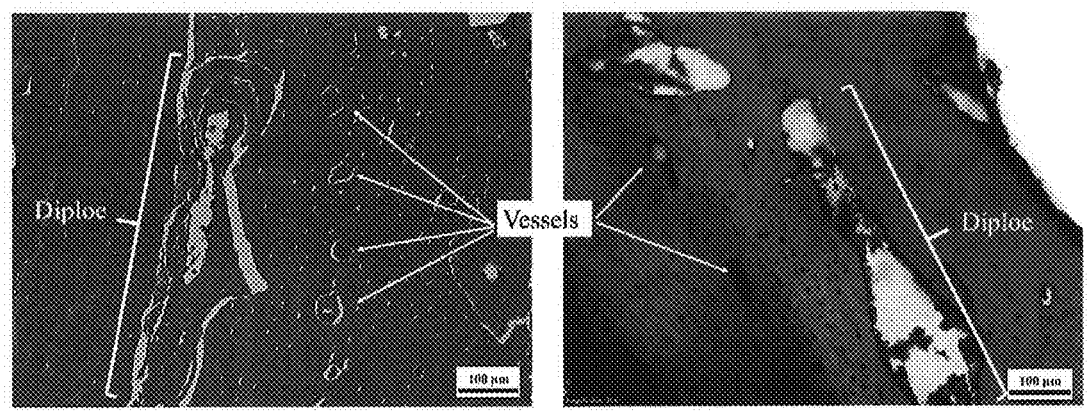
FIG. 17 shows H&E stained (left) and stevenel's blue stained (right) section from a coronal plane of the defect.
Figure 18:
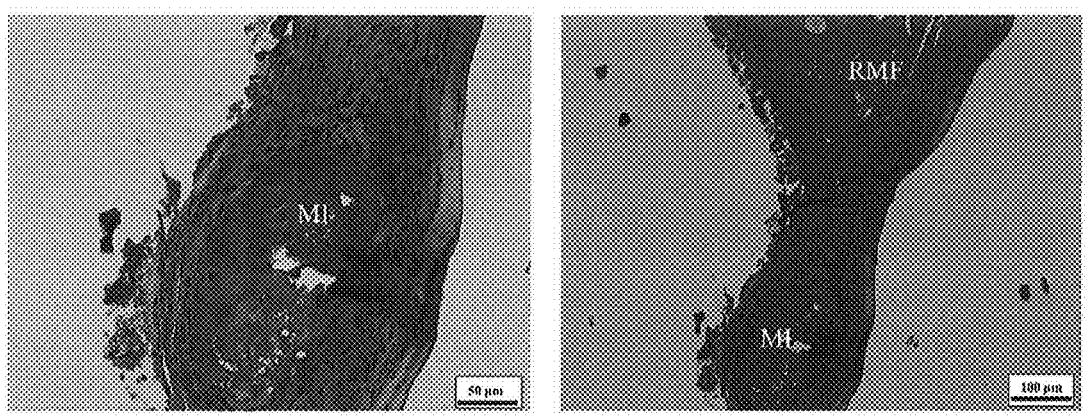
FIG. 18 shows H&E stained section from a coronal plane of the defect. This image was taken from a calvarium of a rat dissected 4 weeks after in-situ printing of the 4-10 bio-ink. A distinct mineral isle (MI) is visible in the defect.

Histological analysis from the rat's native bone (FIG. 17) shows organized lamellae and parallel collagen bundles in the matrix. Also, vessels and a narrow diploe are visible. Rats used for this project had around a year old. Reduced diploe and thick cortical bones on both sides of the calvarium are characteristics of rat's bone at this age Two different type of regenerated bone was seen in RMF; they were either attached to surrounding bone (SB) (FIG. 19) or free and distanced from SB (FIG. 18). Similar regeneration patterns were observed in SEM images (FIG. 13). Purple color at the edge of Regenerated bone (RB) (white arrow in FIG. 18) is belong to hypo mineralized bone. These areas are in the process of mineralization. Raman spectroscopy and BS-SEM also confirmed the presence of hypo mineralized area at RMF (FIG. 16 and FIG. 13 respectively).

Figure 19:
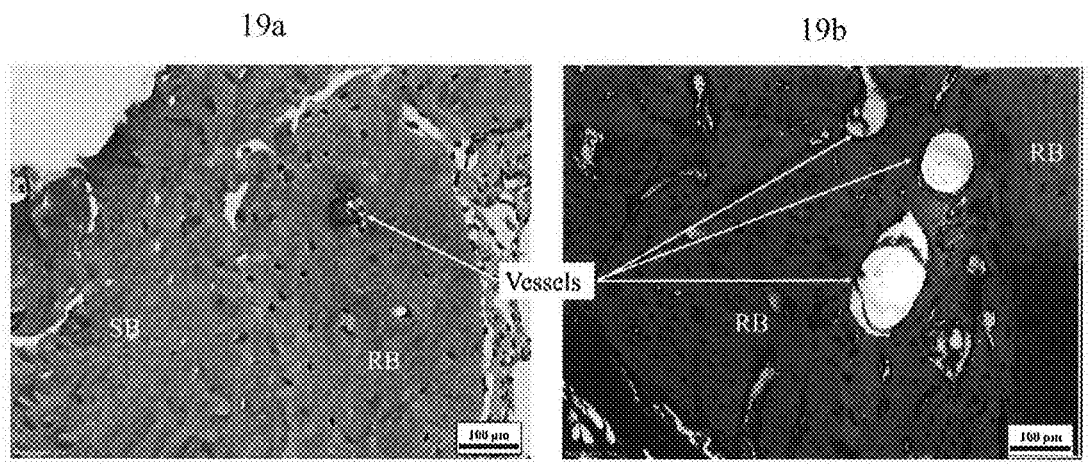
FIG. 19 shows H&E stained (left) and stevenel's blue stained (right) section from a coronal plane of the defect. This image was taken from a calvarium of a rat dissected 4 weeks after in-situ printing of the 4-10 bio-ink. In some areas, RB was continuous with SB, suggesting that these bone are regenerated by proliferation and migration of osteoblasts rather than differentiation of stemcells.
Figure 20:
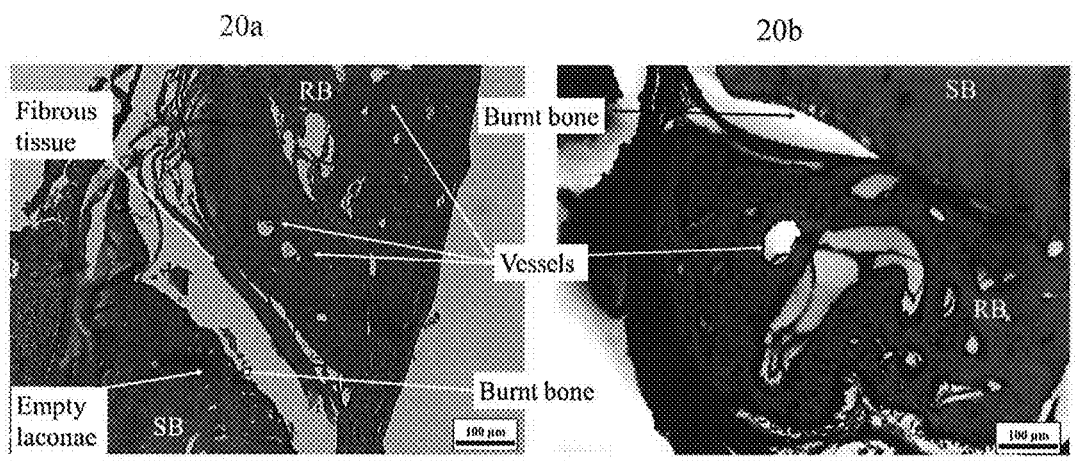
FIG. 20 shows H&E stained (left) and stevenel's blue stained (right) section from a coronal plane of the defect. This image was taken from a calvarium of a rat dissected 4 weeks after in-situ printing of the 4-10 bio-ink. Vascularized regenerated bone (RB) is isolated from surrounding bone (SB) by a fibrous capsule. Cutting bone by high-speed dental burr generated enough heat to burn the bone and kill osteocytes (empty lacunae).

Regeneration of bone also accompanied by vascularization. FIG. 19 and FIG. 20 show some vessels in the RB region. Note that collagen fibers in these new RBs are randomly oriented and do not have a distinct lamellae structure. In other words, RBs are in a form of woven bone and did not go under remodeling process yet.

FIG. 20 shows signs of burnt bone and empty lacunae. Burnt bone were the result of generated heat during partial calvaria removal. The generated heat also killed osteocytes in the SB and essentially killed the peripheral bone. As a result, the rat's body isolated the dead tissue with a fibrous capsule.

Figure 7:
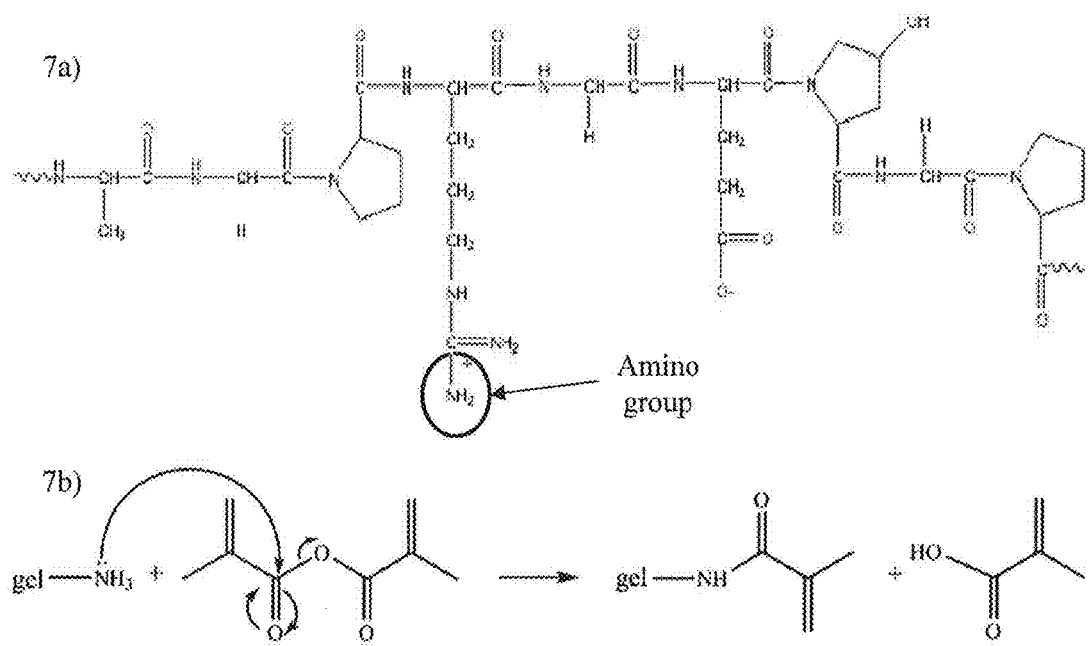
FIG. 7 shows the structure of a gelatin monomer

FTIR results showed that amide peak in MAG compare to gelatin shifted toward higher wavenumbers. This shift is a characteristic of methacrylated gelatin [99-101] and could possibly be attributed to methacrylation reaction that converts gelatin's amino groups to an amide group (FIG. 7). In this addition reaction, methacrylate group of MA was added to the amino group on gelatin chain. In MA molecule, the carbon of —C=O replaced by a proton of the amino group (—NH$_3$) and consequently, an amide bond was created (FIG. 3.b). This newly formed amide group has a slightly different energy level due to interaction with adjacent groups. This different energy level could possibly affect amide's peak in FTIR spectrum and shift the peak toward higher wavenumber. In MAG's FTIR spectrum, a shoulder near amide I peak was visible (near 1645 cm$^{-1}$). This shoulder could be attributed to C=C of grafted methacrylate group. Since crosslinking initiated by opening of C=C bond, this shoulder is not detectable in cross-linked Ink spectrum.

As demonstrated herein, incorporation of sucrose in the MAG-LP nanocomposite has a significant impact on its printability. While not intending to be limited to any particular theory or mechanism of action, this result could be related to two factors. First, cracks in extruded filaments that sometimes led to filament rupture. These cracks are attributed to the weak shear strength of hydrogel's filaments [102]. Hydrogels behave like solid materials and can resist shear stress [103]. In robocasting, extruded filament exhibits an aggressive bending force in order to change its direction from vertical to horizontal. Gelatin hydrogel cannot tolerate this force and breaks. The second factor that interrupts MAG-LP printability is the compressibility of the hydrogel under pressure [104]. Compressibility prevents a uniform extrusion of bio-ink from the tip of the dispenser. Also, under the compressed situation, maintaining a constant pressure in the barrel is challenging, considering that the pressure gradually built up as the printing starts and gradually drops as printing finishes. Gradual increase in pressure causes defected print in first few layers and a fluctuation in extrusion speed afterward. Also, the remained pressure causes the materials to keep flowing out even after the print finished. Therefore, an agent to reduce gelation of MAG-LP could help solve the issue and considerably improve the printing quality.

The printing speed which gave the best result was lower than what was calculated using (Equation 1). The calculated printing speed is 14.75 mm/minute for a plunger speed of 0.3 mm/minute while to best printings achieved at the speed of 9 mm/minute. The reason for this difference could be due to not considering effects of friction, viscosity, and compression in the formula. This formula works when there are no friction, viscosity's resistance, and material compression involve. However, as it mentioned previously, hydrogels tend to become compressed in respond to pressure. Also, the synergic effect of the viscosity and friction during extrusion affect the result [105]. The ratio of (tube cross section area)/(extrusion cross section area) has a reverse relationship with squared extrusion force. In other words, if the cross section area of extruded shape dropped to half (when tube cross section area is constant), the required pressure should be quadrupled to let the extrusion happens [105]. This force will be consumed to oppose friction force. It is reported that in high friction forces, the extrusion rate is controlled by viscosity [105]. That means if the friction is too high, the pressure inside the tube will overcome viscosity before being able to overcome friction and the materials away from friction forces start to move toward extrusion tip and extruded out. Since the dispenser needle that is used for ISP has an inner diameter of only 0.2 millimeters (nearly 50 times smaller than tube's inner diameter), a considerably high friction is involved. Thus, viscosity force controls the extrusion speed. That phenomenon also explains the reason that the optimum printing speed for the 6-20 bio-ink is slower than others (6 mm/minute).

The optimum "dispenser to substrate" distance was reported to be 0.05 mm less than filament's diameter. This difference provides the extruded filament a better grip to the substrate and gives the best printing.

The minimum UV light intensity test determined that at the printer speed of 9 mm/min, 31 mW/cm2 UV intensity is necessary for the cross-linking process. However, higher intensity can also be used. 365 nm UV light fall into UV-A category. UV lights in this category are fairly unharmful and non-mutagenic [106]. The ACGIH minimum exposure recommendation is 1.0 J/cm2 for periods lasting less than 1000 seconds [106]. In ISP with a printing speed of 9 mm/min, UV exposure is around 1 second. Therefore, 31 mW/cm2 is considerably lower than maximum safe exposure at 365 nm. However, it is always recommended to use the lowest possible irradiation. Therefore, UV light (wavelength: 365 nm) with the intensity of 31.5 mW/cm$^2$ used as a standard for all printing. Note that UV exposed homogeneously throughout the entire sample since UV illumination was occurring while the material was extruded out from the dispenser. This fact also was also noticeable from the uniformity of scaffolds cross-linked by intensities above 31.5 mW/cm$^2$ (FIG. 8). Minimum thickness required for crosslinking depends on many factors, including the ability of the material to scatter light [107]. For MAG-LP nanocomposites, it is reported that UV light with intensity as low as 6.9 mW/cm$^2$ can successfully cross-link a film with a thickness of 0.4 mm. Therefore, cross-linking in ISP method is expected to be uniform throughout the entire filament as the filament had a thickness of only <0.2 mm.

BSE-SEM images from remineralization front (RMF) revealed that two mechanisms are involved in remineralization. The first mechanism starts with nucleation of minerals near RMF (arrow in FIG. 13a). These mineral spots later grow and combine with each other and create mineral isles (MI) (FIG. 13b). Afterward, mineral isles merge into RMF and healing continues. The second mechanism that is evident in FIG. 22.c involves simple diffusion of mineral components into the unmineralized tissue. This diffusion probably is a result of cell migration into the effect from RMF and can suggest an active process of osteoconduction.

Raman spectroscopy results showed that $PO_4$ band intensity increases from fibrous toward SB direction (FIG. 16). This shows mineral content increased in this direction which is similar to what was found in SEM images. Bone maturity which is determined by the peak intensity ratio of $PO_4$ to amide band [95] also increase in a similar fashion (from the center of the defect to the SB). This finding is similar to what observed in histological sections that show areas of hypomineralization at the edge of RB (FIG. 17).

EDS analysis detected calcium and phosphorous in the healed area, whereas no calcium and phosphorus were detected in the bio-ink scaffold. This observation indicates that the source for this newly formed Ca and P is something other than the scaffold, perhaps the rat's body. Considering the fact that Raman data showed the presence of phosphorus in a form of $PO_4$, the detected Ca in EDS could be a part of the structure in coordination with $PO_4$. This structure can possibly be a newly formed calcium phosphate or HA.

Raman data from regenerated mineral (that contained Ca and $PO_4$) and SB revealed that these two regions have identical Raman spectrum. This result proofs that regenerated mineral is actually a bone with the same chemistry and elements coordination as rat's native bone.

These findings coincide with those events of the ossification process, and demonstrate that the healing process observed in the presence of bio-Ink occurred according to normal physiological bone healing. No inflammation or infection at healing sites was observed. However, there were some signs of foreign body reaction at RMF (FIG. 20). These reactions were in respond to burnt bone at dissection boundaries and was not related to bio-ink. Dead bone encapsulation made osteoconduction and nutrient transfer to these part impossible. Therefore healing process in these areas was only possible through osteoinduction and the only way for nutrient and oxygen transfer was through the dura. This excess generated heat could possibly compromise healing rate and slowed it down.

EDS data revealed that there was no trace of Si element in both fibrous areas and RB. However, EDS taken from scaffold showed a detectable amount of Si in its matrix. This finding suggests there is no sign of scaffold in the defect and probably the scaffold is completely degraded before dissecting the calvaria (scaffold degraded before 4 weeks). Raman and histological analysis also confirm this finding. Raman analysis showed that two distinct bands of bio-ink (sucrose and hydroxyl proline) are not present in any region of the calvarial bone defect FIG. 16; also, no clear sign of MAG or LP was found in histological sections.

µCT results showed that there was a subtle increase in healing comparing conventional implantation of the scaffold and in-situ printing. However, these data are not statistically significant.

Histology images display the presence of vessels in the RB. The presence of vessels in RB can make it possible for newly developed bone to grow and become thicker since nutrients and oxygen are available to them. In fact, vascularization in RB help enhances healing rate specifically in CSDs [108, 109].

µCT also revealed that implantation of the scaffold with a higher concentration of LP (4-10) resulted in a faster healing compared to the pre-fabricated 2-10. This observation can show the effect of LP concentration on enhancing bone healing rate and supports previous findings about the role of LP in osteogenesis [78-81, 110, 111]. Also, the empty hole had significantly lower healing than pre-fabricated and in-situ printed bio-ink (P<0.05). This finding suggests that regardless of technique, bio-ink has the potential to enhance bone healing in CSD. No statistical difference in healing rate between the pre-fabricated 2-10 and the ISP 2-10 was found. Yet, low power of the study prevents us from ruling out the advantage of ISP in bone healing rate. Although the power of the study for the omnibus ANOVA analysis is >99%, this high power could be due to the presence of empty hole and PCL-TCP treatment. Without considering those two treatments, the study power drops to 38% and also no statistical differences were found between groups. With fewer groups and more replicates the power is expected to increase and provide more in-depth understanding of in-vivo aspects. Note that even if there were no actual differences between the healing rate of the pre-fabricated 2-10 and the ISP 2-10, it would not rule out the advantages of using ISP for craniofacial reconstruction, since this method is devised to also remedy defect repair deficiencies associated with delays in fabrication and precision in implantation.

This data demonstrates an injectable, biocompatible bio-Ink composite and in-situ printing technique for healing CSDs. A practical way of combining fabrication and implantation of micropatterned scaffolds, and thereby eliminate and/or reduce delay in fabrication, as well as to improve implantation precision and provide capacity to modify scaffold's shape during surgery, is demonstrated here.

Example 3—the Effect of a Silicate-Containing Materials (Laponite) and MAG on Physical Properties of Bio-Ink In example 2, it is shown that by incorporating sucrose to an already established polymer nanosilicate, an ISP compatible material (bio-ink) was created. The in-situ printing concept is also demonstrated and validated as a useful bone-defect repair method.

The physical behavior of bio-ink and the role of its main components in this behavior are demonstrated. Printed scaffold is demonstrated to be resorbed faster than the rate that bone is healed. The degradation properties of the bio-ink is demonstrated in the present example.

It is hypothesized that degradation rate, swelling rate, and protein release of bio-ink can be adjusted by controlling LP and MAG concentration.

Implant integration has two steps; bony union between the surface of the implant and native bone segments, and then graft remodeling and resorption in coordination with new bone formation [46]. Graft remodeling is defined as dynamic scaffold degradation and resorption in coordination with new bone formation. This is a critical step; degradation faster than bone formation will cause scaffold loosening and eventually leads to scaffold resorption before the defect heals. On the other hand, a degradation slower than the bone formation is not desirable and can slow the healing process. Therefore, an adjusted degradation rate is needed to optimize the healing rate.

A big challenge in using gelatin hydrogel scaffolds is how to keep scaffold shape and micropatterning intact after fabrication [112]. Fabrication of gelatin-based 3D scaffolds are labor intensive and do not provide precise control over architecture due to high percentage of water in the hydrogels [113]. These hydrogels have the tendency to dehydrate in dry and swell in humid environments [83]. Both of these conditions will damage hydrogel scaffold's shape and precision which makes its manufacturing and handling hard and expensive. An advantage of the ISP technique is that there is no need for handling scaffolds. Also, its fabrication is easier and more precise than current conventional methods. However, the wet environment of the body can still causes the scaffold to swell. Thus, limiting swelling rate can be useful and improve bio-ink scaffold's precision. A swelling test can provide information about the effect of LP and MAG on the swelling rate of the bio-ink and how to control it.

MAG scaffolds have the ability to absorb water and water soluble molecules. Therefore, in the biological environment, they absorb blood, serum, and in general water soluble proteins. Protein release studies can evaluate the ability of scaffold to release already absorbed blood and serum proteins into the peripheral environment. These factors can contribute to enhancing the healing process. These experiments can also demonstrate the capability of the scaffold to carry and release a drug into the defect.

Another aspect of the scaffold fabrication that can also be of benefit to defect healing is the ability to 3D print programmable pores into the scaffold structure. This facilitates the ingress of endothelial cells and mesenchymal stem cells. Endothelial cells are involved in the formation of blood vessels in the defect while mesenchymal stem cells are the progenitors of osteoblasts, which are responsible for bone formation. Thus, the porous network is not only important for mineralized tissue formation, it is also advantageous for vascularization of the bone defect and improving the overall healing rate of the bone.

Materials and Methods

Scaffolds Compositions

The composition of each of the bio-Ink preparations used to prepare the scaffold constructs in this study are provided in Table 6. The total weight shows the amount of bio-ink prepared in each process. Note that this is the minimum recommended weight to prepare. Below these number, mixing process may not yield a homogeneous composite using the mentioned method.

TABLE 6

The composition of each bio-ink used in this thesis.

| | 6-20 | 6-15 | 6-10 | 4-10 | 2-10 | 0-10 |
|---|---|---|---|---|---|---|
| Lp (gr) | 0.3 | 0.3 | 0.3 | 0.2 | 0.1 | 0 |
| Suc (gr) | 0.2 | 0.15 | 0.1 | 0.1 | 0.1 | 0.1 |
| I2959 (gr) | 0.044 | 0.033 | 0.022 | 0.022 | 0.022 | 0.022 |
| MAG (gr) | 1 | 0.75 | 0.5 | 0.5 | 0.5 | 0.5 |
| PBS (gr) | 4 | 4.25 | 4.5 | 4.5 | 4.5 | 4.5 |
| total (gr) | 5.544 | 5.483 | 5.422 | 5.322 | 5.222 | 5.122 |

Sterilization Using Ethanol

All scaffolds not used for in-situ printing purposes went through another sterilization process after printing. The current robocaster 3D printer used for this study does not have an isolated and sterile environment. Therefore, there is a chance of scaffold contamination during and after printing. Thus, scaffolds went under another round of sterilization. Ethylene oxide (EtO) was not used at this step since it has a desiccation step (as mentioned above) that can dehydrate and deform the scaffold. As a result, 70% ethanol was used for scaffolds sterilization [114].

Scaffolds were incubated in well-plates filled with 4 ml of 70% ethanol over a night followed by UV irradiation. Then, they were transferred to new well-plates and soaked in 4 ml PBS twice, each time for two hours. Later on, they were immersed in 4 ml α-MEM for 2 more hours. Finally, they transferred to new well-plate and were ready for a test.

Swelling Test

Gelatin hydrogels have the tendency to absorb water and proteins. In general, they tend to absorb any polar solvent or solute [83]. As a result, they swell in a humid environments and release moisture in a dry environment. This phenomenon changes the shape of the scaffold and causes swelling and shrinkage respectively. Biological environments are a wet environment and can cause hydrogel scaffolds to swell. Therefore studying the swelling rate of bio-ink in exposure to a wet environment is necessary.

Scaffolds in dimensions of 9×6×2 mm were printing and weighed subsequently ($W_d$). Later, they were immersed in α-MEM (Life Technologies, Grand Island, N.Y.) at 37° C. for an hour. Afterward, scaffolds were removed from the medium, their surface dried by a filter paper, and they were weighed again ($W_w$). the percentage swelling was calculated using the following equation:

$$\% \text{ Swelling} = \frac{W_w - W_d}{W_w} \times 100 \qquad \text{Equation 2}$$

Three different compositions of the 0-10, 6-10, and 6-20 scaffolds were prepared according to concentrations mentioned in Table 6. These compositions used to determine the effect of LP and MAG on swelling and four samples per each group were prepared. The 0-10 scaffolds served as a control for pure MAG, the comparison of this bio-ink with 6-10 can show the effect of LP in the swelling rate. Swelling was expressed as mean±SD.

Protein Release Assay

To track the release of protein from the matrix of cross-linked gelatin, fluorescent labeled proteins were added to scaffolds. These labeled proteins are easy to track and distinguish from the gelatin of the scaffold (since MAG is not labeled). There are many different types of fluorescent dyes in the market, but fluorescein is one of the most popular labels for proteins [115]. Also among fluorescein labeled proteins, fluorescein isothiocyanate conjugated bovine serum albumin (FITC-BSA) is a well-established protein for drug delivery [115-117].

For this test, 0.1% wt. FITC-BSA (A9771 SIGMA) was added to bio-inks of the 0-10, 6-10, and 6-20 scaffolds to determine the effect of LP and MAG on protein release rate. Scaffolds with dimensions of 9×6×2 mm were printed and used. Eight samples per each group were designated and each sample was immersed into 2 ml of the degradation media and stored at 37° C. for a week. Degradation media was selected for the in-vitro environment to observe protein release behavior of bio-ink resulting from both diffusion and enzymatic degradation.

Samples were collected at 4 hours, 1 day, 4 days, and 7 days. At each time point, a 50 μL sample was collected from the medium in each well and replaced by 50 μL fresh medium. All samples were then assayed at 488 nm using UV-Vis spectroscopy. The FITC-BSA concentrations were calculated from absorbance using a calibration curve. Swelling ratio was expressed as mean±SD.

To graph the calibration curve, a set of media with known concentrations of FITC-BSA was prepared according to Table 7 (n=3). The absorbance of these media was measured at 488 nm. Based on achieved absorbance, a graph of concentration vs. absorbance was generated. The relation between absorbance and concentration was achieved by a linear regression and used to calculate unknown concentration of FITC-BSA in the supernatant.

TABLE 7

Diluted media used for generating the standard curve. Stock media of 1 mg/mL FITC-BSA in degradation media was used for the standard curve. Degradation media was used for dilution

| | stock | 1:1 | 1:3 | 1:7 | 1:15 | 1:31 | 1:63 | 1:127 | 1:255 | 1:511 | 1:1023 | 2047 |
|---|---|---|---|---|---|---|---|---|---|---|---|---|
| Conc. Of FITC-BSA (mg/mL) | 1 | 0.5000 | 0.25 | 0.125 | 0.0625 | 0.0313 | 0.0157 | 0.0079 | 0.004 | 0.002 | 0.001 | 0.0005 |

Cell-Free Degradation Test

Figure 22:
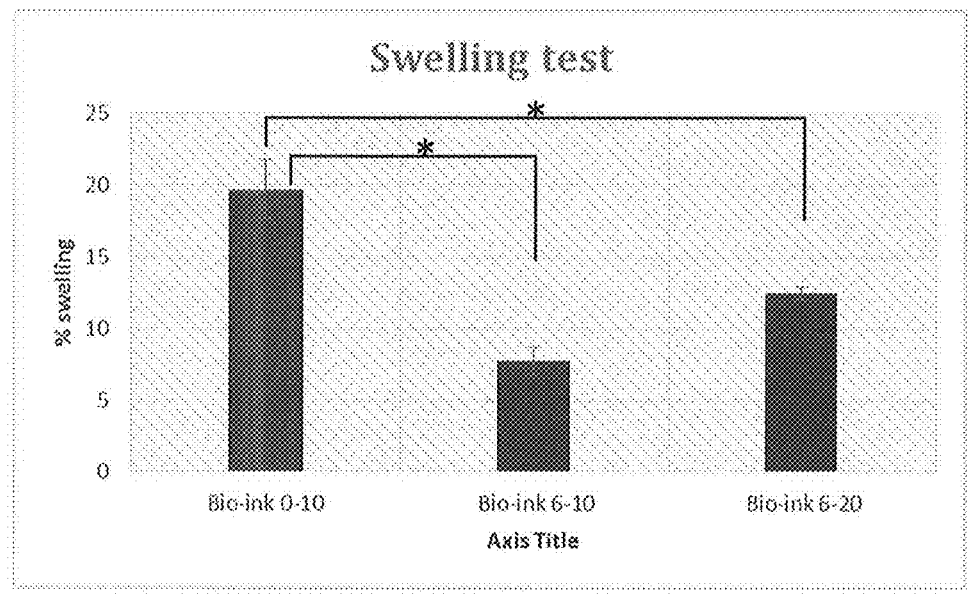
FIG. 22 shows % swelling of different compositions of bio-ink, showing the effect of LP and MAG on degradation (n=4).

To sustain remineralization and maturation of bone, the ability of the scaffold to degrade and remodel in a biological environment is crucial. Degradation rate is important and should be almost similar to bone healing rate of the host to always keep in contact with the defect periphery and support Swelling Test All scaffolds exhibited an increase in weight when they were immersed in the alpha-MEM solution (FIG. 22). The highest swelling rate belongs to bio-ink without LP with 19.7±2.08% swelling which was significantly ($P<0.05$) higher than all other samples (Table 8).

TABLE 8

% swelling of bio-ink with different compositions after immersion in alpha-MEM

| | 0-10 | | | 6-10 | | | 6-20 | | |
|---|---|---|---|---|---|---|---|---|---|
| | weight before immersion (gr) | weight after 1 h immersion (gr) | % swelling | weight before immersion (gr) | weight after 1 h immersion (gr) | % swelling | weight before immersion (gr) | weight after 1 h immersion (gr) | % swelling |
| | 0.16 | 0.188 | 17.5 | 0.146 | 0.159 | 8.90411 | 0.159 | 0.179 | 12.57862 |
| | 0.158 | 0.194 | 22.78481 | 0.131 | 0.143 | 9.160305 | 0.153 | 0.173 | 13.0719 |
| | 0.161 | 0.199 | 23.60248 | 0.15 | 0.162 | 8 | 0.152 | 0.172 | 13.15789 |
| | 0.16 | 0.184 | 15 | 0.141 | 0.148 | 4.964539 | 0.153 | 0.17 | 11.11111 |
| | | Average: | 19.72182 | | Average: | 7.757238 | | Average: | 12.47988 |
| | | SE | 2.075121 | | SE | 0.963588 | | SE | 0.473767 | cell migration [46, 118]. A slow degradation rate should lead to slow healing rate. A cell-free degradation test is a comparative test to study the speed of degeneration of scaffolds and the effect of each ingredient of on the rate of degradation. This test was performed according to previous studies on cell-free degradation of gelatin-based scaffolds [119-121]. For this test two different media were prepared; 1% Pen-Strep in α-MEM was prepared to investigate only hydrolytic degradation rate, and 1% vol. penicillin and streptomycin mixture (Pen-Strep) and 2 U/ml Collagenase type II in α-MEM (degradation media) to evaluate enzymatic degradation. The presence of calcium for active functioning of collagenase is necessary. In other words, calcium is a cofactor of collagenase [122]. Collagenase units (U) are defined as a concentration that cleaves peptides of collagen of bovine Achilles tendon to 1.0 µmole of leucine in 5 hours at pH 7.4 and 37° C. [123].

Scaffolds with dimensions of 4×6×4 mm in six different compositions were printed, weighed, and immersed into 3 ml of medium. Six different compositions of the 0-10, 2-10, 4-10, 6-10, 6-15, 6-20 scaffolds were used for the study and four samples were designated per each group. At 1, 2, 5, 7, 10, and 14 days time points, 50 µL media were collected from each specimen's supernatant and replaced by 50 µL fresh medium. Collected media was analyzed for leached ions using inductively coupled plasma optical emission spectrometry (ICP-OES). At the end of the test, samples were removed (if they were still present in the media), freeze-dried and weighed again. Degradation rate was determined by comparing the adjusted change in weight of each scaffold at the end of the test.

The statistical power of the study was 41% which is too low to claim there is no statistical difference between the 6-10 and 6-20.

Protein Release Assay

Figure 23:
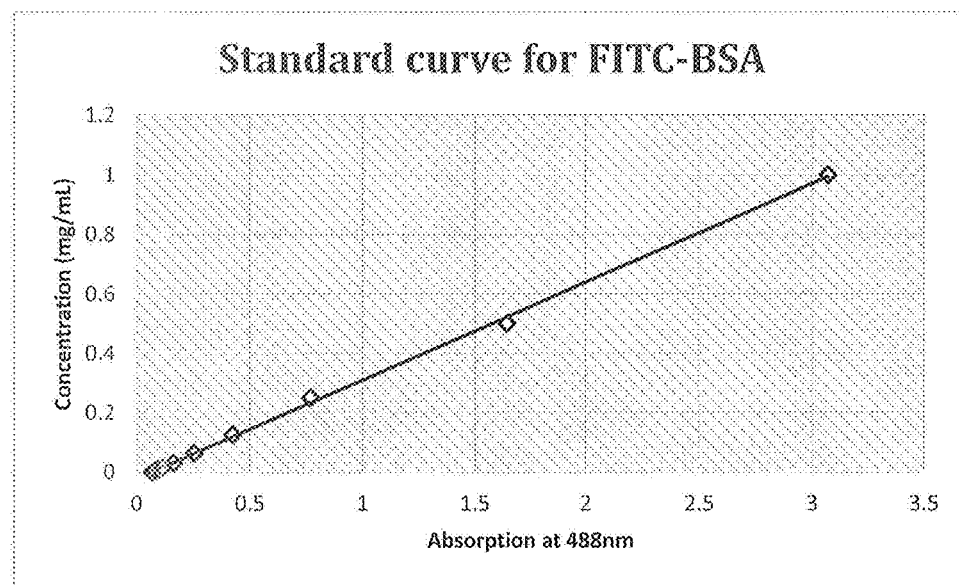
FIG. 23 shows standard curve created for evaluating FITC-BSA concentration in the supernatant.

A standard curve was generated for the assay. This curve was generated by diluting known concentrations of FITC-BSA in alpha-MEM. The concentration of FITC-BCA has a linear relationship with absorption at 488 nm (FIG. 23). This relation follows the formula:

$$\text{Conc.}=(0.3307\pm0.003)(\text{Abs})+(0.0226\pm0.003),$$
$$R^2=0.9992 \quad \text{Equation 3}$$

Using this formula, FITC-BSA concentration in supernatants were calculated.

Figure 24:
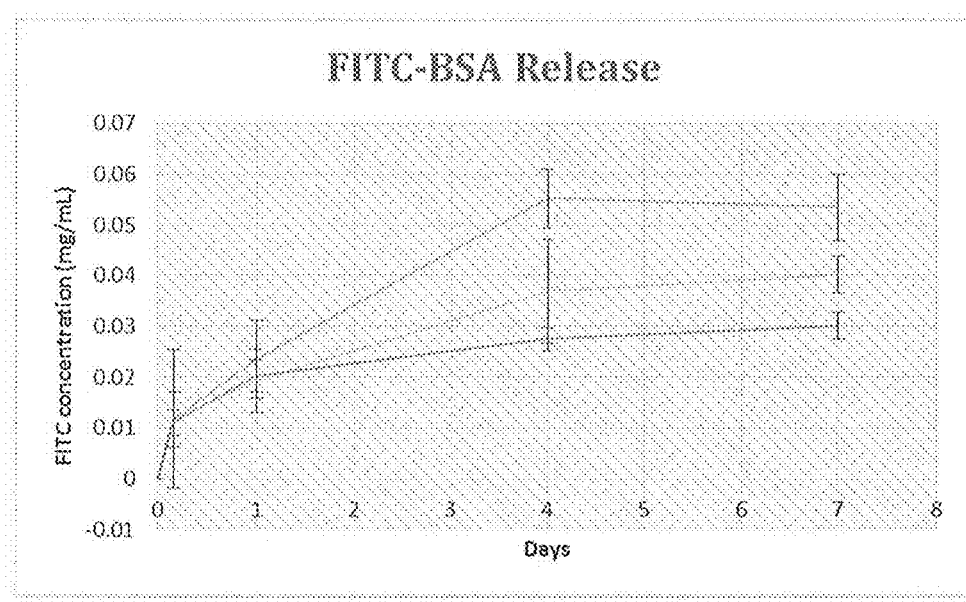
FIG. 24 shows FITC-BSA concentration release pattern.

Release studies showed that scaffolds from the different groups had similar behavior at 4 hours of study (FIG. 24). However, protein release for the 0-10 scaffolds increased from day 1 and continued until day 4. At this point, the scaffold was completely dissolved. The maximum concentration of FITC-BSA measured in the media was 0.055 g/mL.

The results showed that all groups behaved significantly different than the others ($P<0.05$). 6-10 showed the lowest release of FITC-BSA among all types of scaffolds and the 6-20 scaffolds had an intermediate release rate.

Cell-Free Degradation

Figure 21:
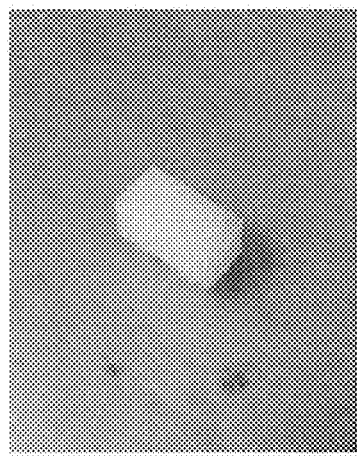
FIG. 21 shows a scaffold of 6-20 before (left image) and after (right image) immersion in a growth medium.
Figure 21:
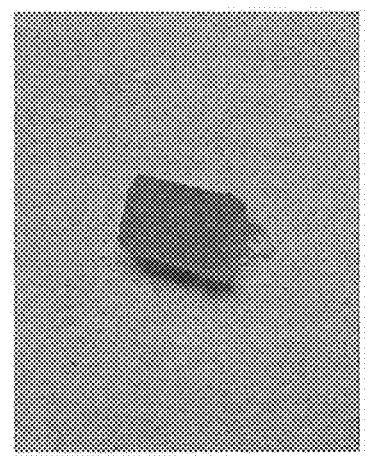
Figure 25:
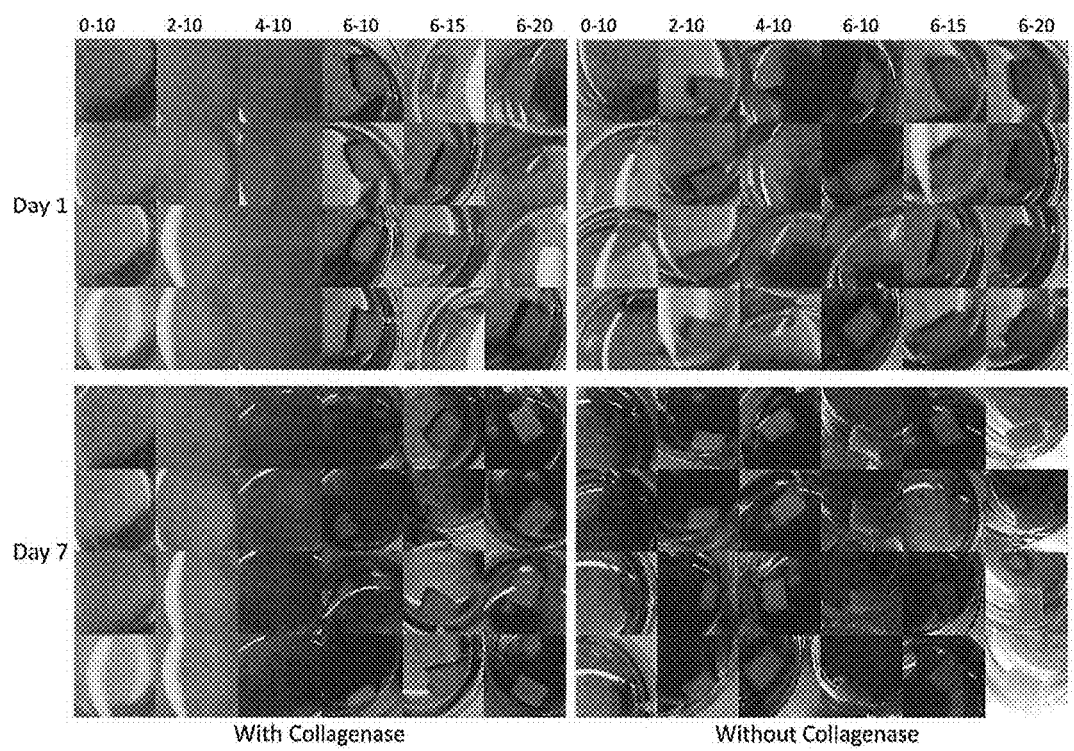
FIG. 25 shows the gross appearance of the scaffolds in degradation media with and without collagenase.
Figure 26:
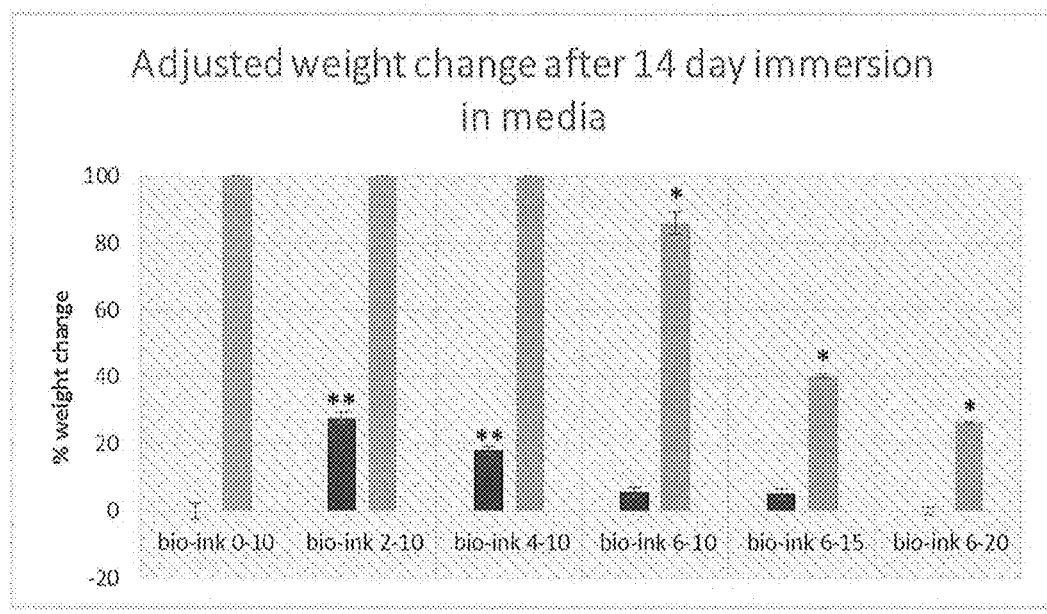
FIG. 26 shows adjusted weight changes of scaffolds after 14 days immersion in the media. (n=4).
Figure 27:
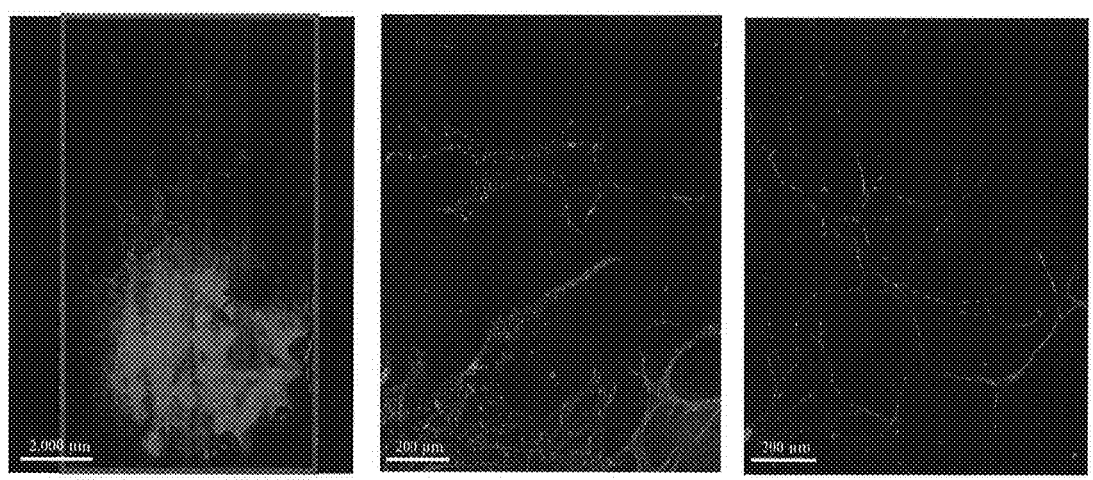
FIG. 27 shows immunohistochemistry images from human PDPCs on bio-inks of the 0-10 scaffolds.
Figure 28:
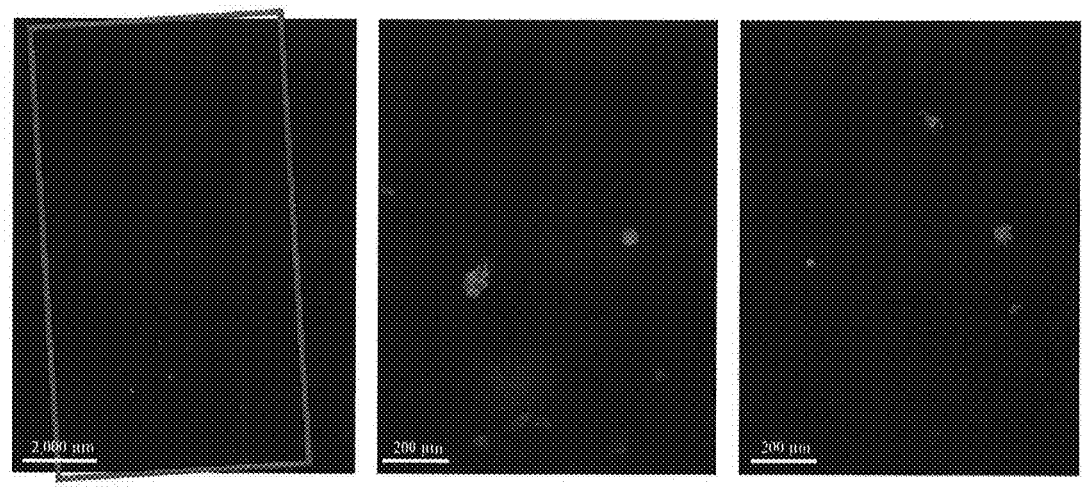
FIG. 28 shows immunohistochemistry images from human PDPCs on bio-inks of 6-10.
Figure 29:
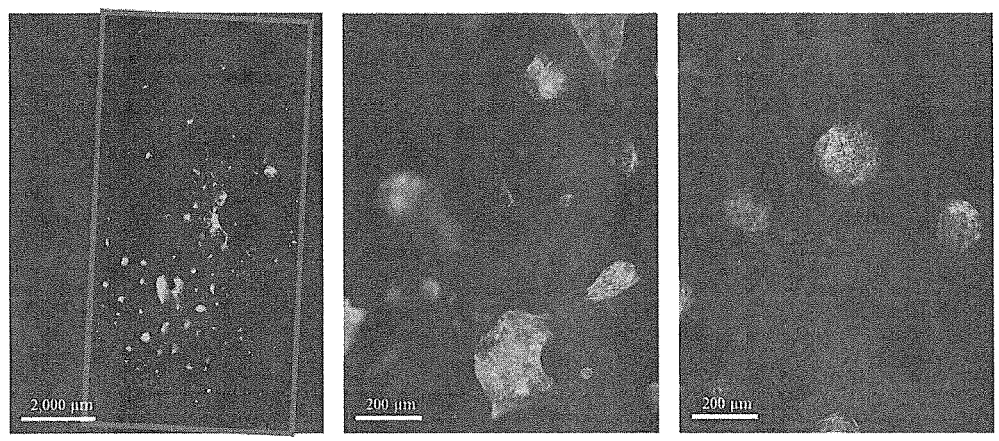
FIG. 29 shows immunohistochemistry images from human PDPCs on bio-inks of 6-20. Immunohistochemistry images from human PDPCs on bio-inks of 6-10. Blue color represents cell's nucleus and green color represents cell's F-actin. Cells were seeded on the bottom side of each scaffold and incubated for one week. The red box shows the scaffold's boundaries.

In the cell-free degradation study, 6 different compositions of scaffold in two different media (w/collagenase and w/o collagenase) were tested. Visual changes of the samples in degradation test is shown in FIG. 21. In degradation media (with collagenase), the 2-10, and 4-10 scaffolds were completely degraded in less than a day. Interestingly, the scaffolds in 0-10 group did not completely degraded and only become smaller. At day 5, the 0-10 scaffolds samples were completely degraded. At day 7, the 6-10 scaffold started to disintegrate into small pieces FIG. 25. The pattern of degradation for 6-10 was totally different from what was observed for the 0-10 scaffolds. No notable changes in samples gross appearance were observed from day 7 until the end of the study (14 days) except disintegration and degradation of 6-10 scaffolds. The degradation test in alpha-MEM (without collagenase) showed that none of the scaffolds exhibited any notable changes in their gross appearance in two weeks of study.

Two weeks after immersing samples into each media, all samples were taken out, lyophilized, and weighed ($D_{14}$). To compare degradation among different groups, the scaffolds' lyophilized weights were compared to the adjusted dry weight of the samples at day zero (lyophilized right after printing). Day zero dry weights were adjusted because samples did not have same exact weight after printing. Considering that dried samples are light in weight, the weight difference after printing between the degradation study samples and day zero samples (which are different scaffolds) could introduce artifact and error into the analysis. To adjust the difference, the average weight reduction after lyophilization was measured for day zero samples of each composition. This average was termed "day zero constant" and showed the average weight reduction of each type of bio-ink if they were lyophilized right after printing (day zero). To determine "day zero constant" 8 samples per each group were used (n=8).

$$\text{Day zero constant} = \frac{\sum_{group}\left(\frac{W_w - W_d}{W_w} \times 100\right)}{n} \quad \text{Equation 4}$$

$W_w$: Day zero samples weight after printing
$W_d$: Day zero samples weight after freeze-drying This constant was used on the degradation study samples to evaluate their dry weight if they were lyophilized after printing:

$$D_0 = d_0 X \text{ (Day zero constant)} \quad \text{Equation 5}$$

$D_0$: Adjusted degradation study samples dry weight after printing
$d_0$: Degradation study samples dry weight after printing Afterward, the adjusted degradation rate was measured by the following formula:

$$\% \text{ weight change} = \frac{D_0 - D_{14}}{D_0} \times 100 \quad \text{Equation 6}$$

$D_0$: Adjusted degradation study samples dry weight after printing
$D_{14}$: Degradation study samples weight after 14 days The degradation study in alpha-MEM showed no weight change in the 0-10 group (the actual mean of weight change was −1.002%) and the highest weight loss was belong to the 2-10 scaffolds and then the 4-10 scaffolds (FIG. 22). None of the other groups had significant differences in degradation. The power of the study is >99%.

In collagenase media, the 6-20 scaffolds showed the least weight loss followed by the 6-15 scaffolds. The 6-10 scaffolds exhibited more than 85% weight loss and other compositions (0-10, 2-10, 4-10) degraded completely after 14 days.

Figure 6:
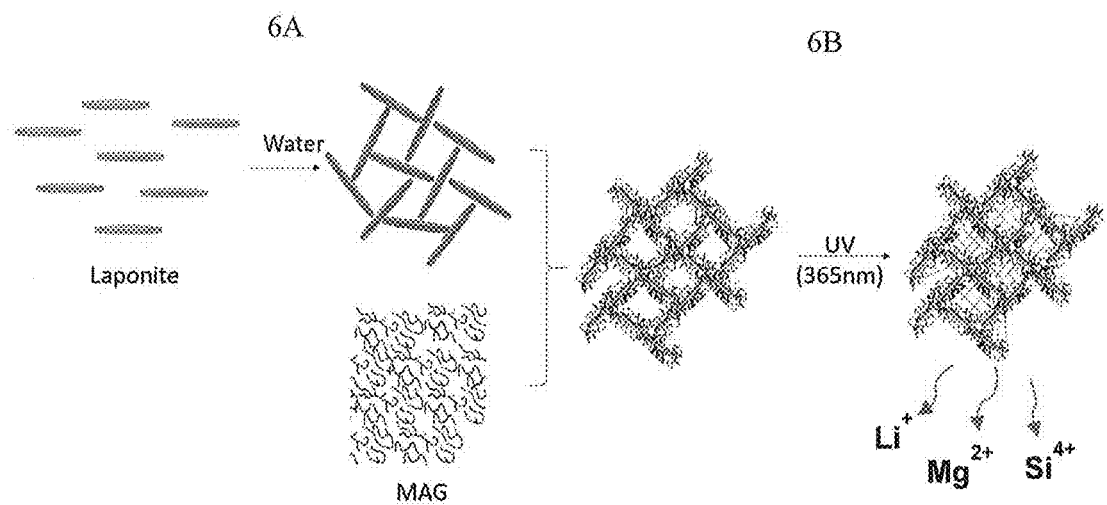
FIG. 6 shows the mixing step to prepare a bio-ink.

Bio-ink swelling decreased by increasing LP concentration and conversely increased by increasing MAG. It shows that water diffusion into the hydrogel is regulated by the concentration of LP. The reason for this phenomenon could be related to the entangled structure of LP-MAG complex. This microstructure interaction with MAG polymer chains creates an entangled and rigid structure (FIG. 6). At low LP concentration, its nanoplatelets surface completely covered by MAG. Increasing LP will provide more sites of attachment for gelatin and increases the ionic interaction between LP and MAG which results in a more rigid structure [124]. Rigid structure provides less flexibility for the hydrogel network which makes it harder for water molecules to penetrate. Hence, the scaffold's water absorption decreases. On the other hand, the addition of more MAG to the bio-ink will introduce more free-MAG (not in interaction with LP) in the matrix. These free chains can readily absorb water and consequently swell. In other words, network strength is regulated by LP and the swelling rate depends on the MAG to LP ratio.

Data from the protein release studies indicates that all three types of bio-inks (0-10, 6-10, 6-20) exhibited a burst release initially and the release rate dropped gradually. When area close to the surface of scaffold released their FITC-BSA, continuation of the release depends on diffusion of FITC-BSA from the core of scaffold to the surface. Reduction in release rate implies that release (diffusion) of FITC-BSA from the surface to the media is faster than diffusion of FITC-BSA within the scaffold. In other words, the protein release is limited to diffusion of FITC-BSA within the scaffold [125]. Note that the media contained collagenase. Therefore, some of FITC-B SA molecule release is due to gelatin degradation rather than diffusion. Enzymatic degradation of gelatin occurred from the surface. Mladenovska K et al also reported the same pattern of enzymatic degradation of gelatin [126]. As the scaffold degrades, it gets smaller and its surface area reduces. Reduction of surface area reduces available sites for enzymatic degradation. Thus, this phenomenon also can contribute to the reduction in release rate of FITC-BSA as a function of time.

The lowest protein release rate belonged to the 6-10 group. This result was expected due to the prediction of the LP and MAG interaction. Since MAG to LP ratio is the lowest in the 6-10 scaffolds, it has the strongest network of all groups. While strong networks resist water diffusion, they would not let the trapped molecules escape either [127].

In the protein release study, the average weight of a 0-10 scaffold printed was 140 mg. At this weight, scaffolds contained about 140 μg FITC-BSA. If the whole scaffold dissolves in 2 mL media (which happened in this study), the concentration of FITC-BSA should be 70 μg/mL. This difference could be because of some burst release while scaffold was being washed (after printing and before immersion). Also, more importantly, replacement of 50 μL of media with a fresh one at each time point gradually diluted it. It also explains the drop in concentration after 4 days for the 0-10 scaffolds. Since the scaffold is completely degraded no more FITC-BSA was released and collecting a sample only diluted the supernatant.

The degradation study reveals that hydrolytic degradation plays a small role in MAG degradation. It is slow enough that no weight loss was detectable at 2 weeks in the 0-10 scaffolds. By this time, the 2-10 scaffolds had the most weight loss. The reason for this weight loss could be a release of LP into the media considering that MAG is not subjected to degradation in two weeks. The 2-10 scaffolds have a low concentration of both LP and MAG and a considerably higher water portion which resulted in a weaker microstructure. In this weak microstructure LP can release into the media easier [127]. The 4-10 scaffolds are probably suffered from the same issues. Therefore, a collagenase-free environment probably provides a situation in which LP release is controlled by diffusion [124]. Other scaffolds (6-10, 6-15, and 6-20) have strong enough microstructure that significantly slowed down the release of LP [127]. Inductively coupled plasma optical emission spectrometry (ICP-OES) is a very precise technique to measure ion concentration in a media. This technique can reveal more in-depth information about LP release rate. Thus, it is highly recommended to investigate this theory using ICP-OES.

Enzymatic environments are more similar to the in-vivo situation in a way that cells in the body use different proteases to break down collagen fibers and matrix to remodel them [128]. Therefore studying degradation in collagenase media can provide more realistic results for scaffold degradation rate and factors affecting them. Results from the degradation study using collagenase media showed that as gelatin concentration increased, scaffold's weight loss was reduced so scaffolds with low MAG such as the 0-10, 2-10, 4-10 scaffolds are completely degraded and the 6-10 scaffolds lost a significant portion of its mass. This observation suggests that enzymatic degradation possibly is controlled by gelatin concentration [119, 120, 129]. The reason that the 6-10 scaffolds showed a slower degradation rate relative to the 0-10, 2-10, and 4-10 scaffolds, could be due to its high LP concentration. Overall, increased LP concentration will reduce degradation rate of hydrogels [130] relative to other bio-inks with lower LP. This high LP concentration can possibly halt the release of gelatin's by-products and trap them in a locally created thixotropic gel [131]. In other words, this gel makes it harder for collagenase to access the inner network of gelatin. This phenomenon could explain the reason that the 6-10 scaffolds degradation pattern was different from that of the 0-10, 2-10, and 4-10 scaffolds. Those disintegrated pieces of the 6-10 scaffolds were actually local thixotropic gels that held gelatin by-products together. This theory is strengthen when it was observed that lyophilized remnants of the 6-10 scaffolds were powder instead of pieces of scaffolds. The 6-20 scaffolds showed the least weight loss followed by the 6-15 scaffolds.

These tests provide a more in-depth understanding of bio-ink and the role of LP and MAG on bio-ink physical behavior. To summarize, it was shown that an increase in LP and/or MAG concentration reduces degradation rate. However, MAG concentration plays a bigger role in enzymatic degradation. In other words, MAG concentration controlled enzymatic degradation. Furthermore, an increase in LP concentration reduces protein release and swelling rate, while an increase in MAG concentration increases protein release and swelling rate.

Example 4—Effect of Increasing MAG and LP Concentrations on the Biological Properties of Bio-Ink Increasing LP and MAG concentration in the bio-Ink is demonstrated to significantly reduce the degradation rate of the scaffold prepared therefrom. The present example demonstrates the effect of these changes on biological properties of bio-ink. To propose an optimum concentration for bio-ink, a set of in-vitro studies will be conducted to examine cell toxicity, attachment, proliferation, migration, and differentiation.

Materials and Methods

Cell Migration and Attachment

A key characteristics of an ideal scaffold is to enhance cells' migration and attachment. Therefore, the capacity of different bio-ink compositions to facilitate cells' migration and attachment was evaluated. For this study, scaffolds with dimensions of 6×12×1.5 mm were printed. Three different compositions of the 0-10, 6-10, and 6-20 hydrogels were used for the study and 6 replicates were designated for each composition. PDPCs were seeded on one side of each scaffold's top surface. On each scaffold approximately 25,000 cells were seeded. A week after seeding, scaffolds were fixed and stained by Hoechst and Phalloidin immunohistochemical dyes. Immunofluorescence microscopy images were obtained using a Large Fields Fluorescence Stereo Zoom Microscope (Axio Zoom.V16, ZEISS, US).

Periosteum derived progenitor cells (PDPCs) have several advantages for bone regeneration in-vitro studies. A minimal invasion is needed to harvest these cells. PDPCs can keep their differentiation capacities through many passages (usually P5) and also grow fast [132]. They maintain their growth curve for more than thirty doubling [133] and would not become senescence until around eighty doubling. PDPC's growth would not be inhibited by contacting each other, and they continue to proliferate into higher densities [134, 135]. PDPCs have the capacity to differentiate into osteogenic, chondrogenic, and adipogenic lineages [136]. Harvested PDPCs from old individuals also keep their growth potential but lose the capacity to differentiate into chondrocytes and adipocytes [137]. Furthermore, PDPCs regenerate bone de novo and have osteoinductive effects [138]. Also, reagents to induce in-vitro differentiation in PDPCs are well-established. All these factors make PDPCs ideal for regenerative tissue engineering and a more accurate clinical translation [136].

PDPC were obtained according to IRB protocol (Study ID STU 012011-181) as previously described [139]. These cells (passage 2) were cultured in 75 cm$^2$ flasks with growth media in a humidified atmosphere of 95% air and 5% CO2 at 37° C. and incubated for a week. The media was changed every two days to keep the growth condition optimum and also prevent any potential contamination. Growth media was an α-MEM based media contained 10% fetal bovine serum or FBS (VWR, Radnor, Pa.), and 1% streptomycin and penicillin or Pen-Strep (HyClone, 10,000 unit/ml) as an antibiotic.

A week after plating, cells were trypsinized (T4049 SIGMA) and counted. Cell concentration was adjusted to 2,750,000 cells/ml and 20 μL of the cell media (25,000 cells) was used for seeding (passage 3). Cells were seeded on scaffolds inside 12-wells plates. Cells were tried to be seeded only on one side of the scaffold in order to analyze cells' migration. However, due to the hydrophilic surface of bio-ink, in many samples cell media spread all over the scaffold once they were seeded.

Cell culture media is a solution that can provide essential inorganic and organic components that cells need for growth. It has three main component of "Minimum Essential Media" or (MEM), a blood serum, and an antibiotic.

The minimum essential media (MEM) contains essential inorganic salts, amino acids, vitamins, and sugars for cell viability. It also has a buffer and pH indicator such as phenol red to keeping the track of pH. There are many different types of MEM such as Eagle's MEM, Dulbecco's modified Eagle's Medium (D-MEM), and alpha-modified minimum essential media (α-MEM). Each is designed for different application and cell line. For our study, α-MEM (gibco by life Technologies™) was the suitable MEM [125] and used for the entire study.

The serum contained proteins, vitamins, hormones, and growth factors required for cell viability and growth. The penicillin and streptomycin antibiotic also added to growth media to eliminate any bacterial growth in case of contamination.

An immune-histochemical staining technique was used to stain cells' nuclei and actin filament. By staining those two, studying the osteoblasts adhesion, migration, and proliferation can be visualized and analyzed using fluorescent microscopy and image processing techniques.

The blue-fluorescent Hoechst dyes are nucleic acid stains that are sensitive to DNA conformation and chromatin. These bisbenzimidazole derivatives are supravital stains that bind to the minor groove of DNA. The dye's fluorescence will be enhanced two times more by binding to AT-rich dsDNA regions versus GC-rich strands. For that reason, Hoechst can be used for many different applications from flow cytometric recognition of DNA damage [140] to cell counting [141]. The advantages of Hoechst over DAPI staining for cell counting application is that Hoechst is cell permeable and non-toxic which makes it a more efficient dye. For this study Hoechst 33342, trihydrochloride, trihydrate, (H3570, Invitrogen, US) with absorption at 405 and emission at 440-500 nm was used.

Phallotoxins are toxins that are isolated from Amanita phalloides mushrooms. These toxins can bind competitively to F-actin. Therefore, by labeling the toxin with a Fluorescent dye, the amount of F-actin in cells can be quantified under a fluorescent microscope [142]. For this study Alexa Fluor® 488 Phalloidin (A12379, Invitrogen, ThermoFisher scientific) is used that excites at 488 nm and emit at 500 nm-650 nm.

To prepare samples, cells were fixed by adding 2 ml of 4% PFA to each well for 10 min and washing twice with PBS. Then, samples were permeabilized by immersing them in absolute acetone at −20° C. for 2-3 minutes. Afterward, the acetone was diluted gradually with cold PBS. Later on, hydrogels incubated in PBS with 1% BSA for more efficient staining. After aspirating BSA solution, nuclei stained by incubating samples in a Hoechst solution of 2 µg/ml for 15 min and washing twice with PBS. F-actin stained by incubating the samples with 200 µL of 0.33 µM Phalloidin for 30 minutes and then washing twice with PBS. The whole process of staining was done in a dark area to prevent bleaching of the dyes.

Cell Migration and Attachment

A week after incubating the seeded 0-10 scaffolds, PDPCs spread on the surface. After proliferation on the seeded spot, they immigrated and colonized unneeded areas of samples. Their stretched filopodia) shows that the sample's surface is cellophil and cells were in the process of migration On the 6-10 scaffolds, very few cells survived and those survived had rounded shapes). Cells can only be found in seeded region and did not migrate to other areas of the scaffold. No clear filopodia and lamellipodia were detected.

Fluorescent microscope images from 6-20 scaffolds showed colonies of cells on the scaffold although the covered area by cells on the 6-20 hydrogels is smaller than the covered area on the 0-10, it is much bigger than the covered area on the 6-10 hydrogels. In high magnification, some stretched filopodia and lamellipodia are evident. Furthermore, presence of the colonies outside the seeding area, indicating that the cells were able to migrate. Moreover, microscope images show the cells colonies in different planes; considering that scaffold's surface is relatively flat, colonies in different planes can indicate that cells were migrated into the scaffold.

Immunohistochemistry staining showed cells reaction to the surface of the 0-10, 6-10, and 6-20 bio-inks Overall, cells on the 0-10 hydrogels were stretched (fibrillar adhesions) and connected with filopodia and also moved from seeding area to cover the scaffold. These observations indicate that the surface of the 0-10 hydrogels enhanced cells attachment and facilitate their migration [114, 143]. On the other hand, rounded shape of cells on the 6-10 hydrogels shows that cells did not attach well to its surface. Low cell count also indicates its toxicity to cells. It is shown that a high concentration of LP could be toxic to cells. Previously, Gaharwar et al. showed that LP concentration above 1 mg/mL in the media can be toxic to cells [80]. At those concentrations, LP nanodisks engulf cells and limit cells functionality. Also, LP nanoplatelets can electrostatically bind to proteins in the media and make them inaccessible for cells. Therefore, LP release should be limited.

Cells arrangement on the 6-20 hydrogela under the fluorescent microscope shows a higher count of cells relative to the 6-10 hydrogels with more stretched morphology. Cells colonies outside seeding area were also noted. These findings reveal that cell's attachment, migration, and growth are improved on the 6-20 compared to 6-10 hydrogels. However, cells still struggle reaching their maximum attachment and growth. It can be indicated that the toxicity a scaffold with a high level of LP can be reduced by increase MAG concentration. In addition, cells attachment can be restored in a similar way. This improvement in cell attachment can be due to a reduction in LP release rate in a similar way as we saw in [00254]. A control on LP release is possible through two distinct ways, by reducing LP concentration or by increasing MAG and trapping LP particles inside the matrix. The first option can limit overall LP release however it would not fix the LP burst release that was seen in degradation study. As a result, the initial burst in LP release still can damage cells. An increase in MAG concentration besides limiting LP release can provide more binding sites (RGD motifs) for cells and consequently enhances cell's attachment.

By increasing LP and MAG concentration, degradation rate significantly reduces. However, high concentrations of LP is toxic to cells. Like other drugs, LP can be toxic if it exceeds its toxic dosage. Here, a strong relation between bio-ink's components and its physical and biological properties is established.

Additional compositions will be tested in-vitro to find the optimum composition of bio-ink. A 4-20 or 5-25 bio-Ink preparation which have a high gelatin portion to control LP release will be examined, as well as to enhance cell attachment and possibly reduce degradation rate will be gauged. Also using MTS assay can help understanding the bio-Ink's toxicity. Cell differentiation will also be examined.

Example 5—The Effect of Nanosilicate on Osteogenic Properties of Gelatin Based Hydrogel for In-Situ 3D Printing Applications Gelatin hydrogels have innate properties suitable for tissue regeneration, yet they are not viable for healing bone critical size defect (CSD) because they do not maintain precise scaffold micropatterns after fabrication and do not facilitate rapid bone regeneration. Biosilicate nanoparticles (Laponite) integration has the potential to improve healing rates by enhancing osteogenesis. In situ printing can improve scaffold micropattern stability by direct printing into the defect site. Thus, in situ 3D printing of laponite-gelatin scaffolds for inducing rapid healing of CSDs via enhanced osteogenic differentiation is presented here.

The Laponite-gelatin scaffold was prepared by mixing Laponite with methacrylated gelatin (MAG), which was tested for methacrylation using Fourier Transform Infrared (FTIR) spectroscopy. Sucrose was used to increase viscosity and reduce gelation of the printing ink. IRGACURE 2529 was used as a cross-linking agent. During printing, cross-linking was initiated by UV light (365 nm) at the tip of printer nozzle. UV light intensity (0-42 mW cm-2) was optimized for degradation rate in vitro prior to in vivo testing. Scaffolds were in-situ 3D printed directly into calvaria bone CSD using varied Laponite concentration (0-4 wt. %) to determine optimal bone density (microcomputed tomography) and chemical structure (x-ray absorbance near edge structure [XANES] spectroscopy).

FTIR confirmed successful MAG synthesis. The addition of Lp increased integrity of printed hydrogel. In-situ printing using 10% MAG, 5% Suc, 4% Lp and 37 mW·cm-2 UV light showed more than 50% bone regeneration in CSD after 4 weeks. XANES analysis showed that newly regenerated bone in CSD had similar calcium phosphate-based chemical structure as that of the surrounding calvarial bone. Thus, the MAG-Lp-Suc construct successfully in-situ printed and induced rapid CSD bone regeneration.

Relatively high levels of silicate nanoparticles enhance the mechanical stability of hydrogel scaffolds while enhancing the bone healing rate in bone defects.

MAG was synthesized by reacting 0.1 gr/ml porcine gelatin and 0.8 ml/gr$_{(MAG)}$ Methacrylate Anhydride in Dulbecco's phosphate buffered saline (DPBS).

To make the bio-ink, LP, MAG 5% w/w$_{(MAG)}$ sucrose, and 0.5% w/w$_{(MAG)}$ IRGACURE 2959 mixed in DPBS.

Nano-disk shaped Lp powder in aqueous environment form a hollow structure. Charged surface of Lp attracts MAG strings and in presence of UV light, MAG strings crosslinks and create a rigid structure. A bone defect of 4±1 mm by 6±1 mm on rat's calveria was created. After mapping the defect by printer, a scaffold with average pore size of 0.5 mm was designed and printed directly into the empty space with a 0.2 mm margin from each edge. The composite was crosslinked while printing by pinpoint UV illumination (wavelength: 365 nm) with output intensity of 31 mW/cm$^2$.

The presence of Si in scaffold but not in unhealed region of bone in EDS analysis demonstrated the complete degradation of scaffold before harvesting the bone (4 weeks). It also shows presence of "Ca" and "P" in healed region that can suggest presence of calcium phosphate.

Micro-CT results show improvement in healing from empty hole to implanting prefabricated 10% MAG-2% Lp that shows the effect of material on bone healing. In-situ printing of the same bio-ink shows bone healing improvement from 35% to 45% that could be due to perfect matching of scaffold in defect and facilitated cell immigration and ingress. In-situ printing of same bio-ink with doubled concentration of Lp (4%) showed a 10% improvement in healing over bio-ink with 2% Lp. This supports the role of Lp in enhancing osteogenesis.

BSE-SEM images showed two mechanism of bone healing in regeneration front. First mechanism starts with ectopic nucleation of minerals. As they grow, they combine and form mineral isles. Eventually, these isle merge with regeneration front and healing proceeds. The second mechanism involves gradual mineralization from the regeneration front, which starts at the edges of the defect and migrates into the defect.

Raman Spectroscopy shows that sucrose and hydroxy-proline which are characteristics of bio-ink were not in unhealed area that confirms scaffold degradation. Mineral content increases moving from unhealed region to surrounding regenerated bone. The mineral to organic ratio which associates with bone maturity increased. regenerated bone had identical spectrum to surrounding bone. This fact demonstrates that regenerated mineral in the defect is bone having an identical chemistry to indigenous bone. It also demonstrates that new regenerated bone was able to become fully mature.

Example 6—Methacrylate Modified Chitosan Synthesis

The present example describes a methacrylate modified chitosan. This material may be used as the bio-Ink and therefore also as part of the 3-D bio printing method for tissue repair described herein.

Methacrylated chitosan (MAC) is used in a 3_D printing technique to micro-pattern chitosan hydrolysis. 3D printing was used to micro-pattern chitosan hydrogels into 3D structures for applications in bone regeneration. Thus, we test the hypothesis that 3D printed chitosan hydrogels have sufficient strength and stability to be used in applications of bone healing.

Methods:

Methacrylated chitosan (MaCh) was synthesized by mixing acetic acid, deionized (DI) water, chitosan, methacrylate anhydride, pyridine, and ethanol. Ethanol was added to open chitosan chains, exposing more amino groups to methacrylate anhydride. Conversely, too much ethanol promotes gelation of the solution, halting the methacrylation process. After synthesis, the solution was dialyzed against ultrapure water (18.2Ω). After purification, two groups were created from the solution to be freeze-dried for one week: 1) MACh without sucrose, and (2) MACh with added sucrose in a 1:1 mole ratio to chitosan. Methacrylation was tested by FTIR. Each group was tested for solubility. 4 wt. % MACh from the sample with sucrose was prepared for 3D printing, and IRGACURE 2959 was used for cross-linking. During printing, cross-linking was initiated by UV light (365 nm, 42 mW·cm-2) at the tip of printer nozzle.

FTIR confirmed successful methacrylate grafting into chitosan backbone. The 45 ml ethanol concentration resulted in the greatest dissolution, indirectly indicating the highest degree of methacrylation. Addition of sucrose to dialyzed MACh considerably increased its solubility. This may be attributed to the sucrose interaction with chitosan (making them globular) and preventing water from aligning the chitosan chain parallel and packed. 4 wt. % MACh was printed successfully with good integrity of micropatterns.

The present results demonstrate that methacrylated chitosan (MAC) may be used as a 3-D printing material and is suitable for providing a micropatterned tissue scaffold. These properties can be used for applications in soft tissue and bone tissue repair.

Materials and Methods

Figure 30:
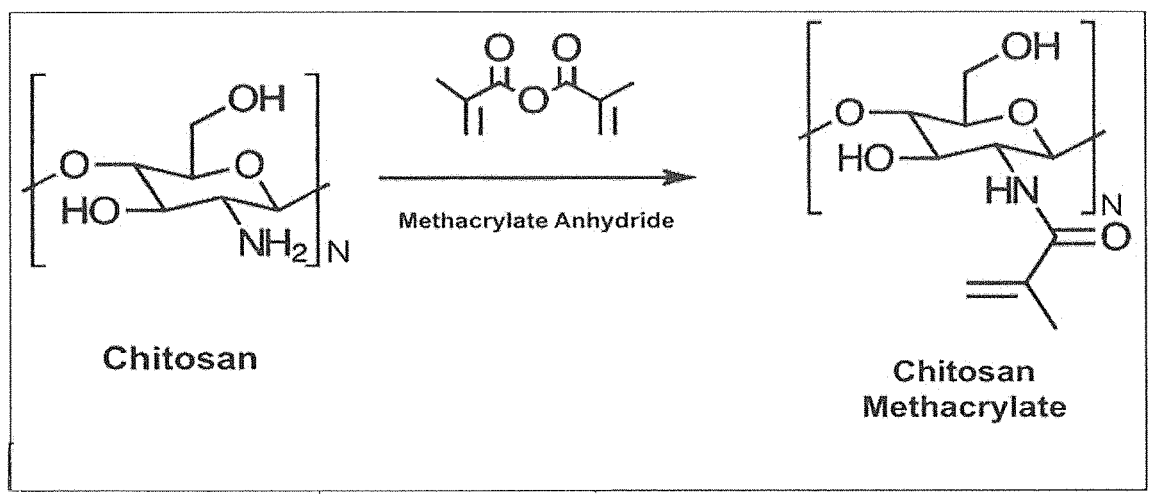
FIG. 30 shows the methacrylation of chitosan to provide chitosan methacrylate (MAC).
Figure 31:
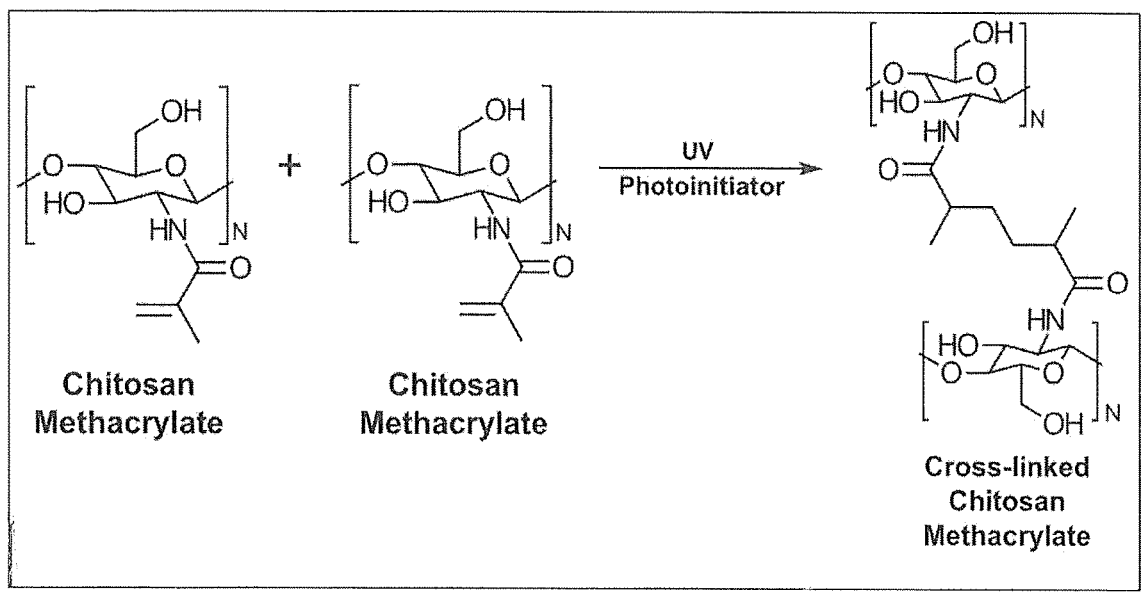
FIG. 31 shows UV-initiated cross-linking of MACs.
Figure 32:
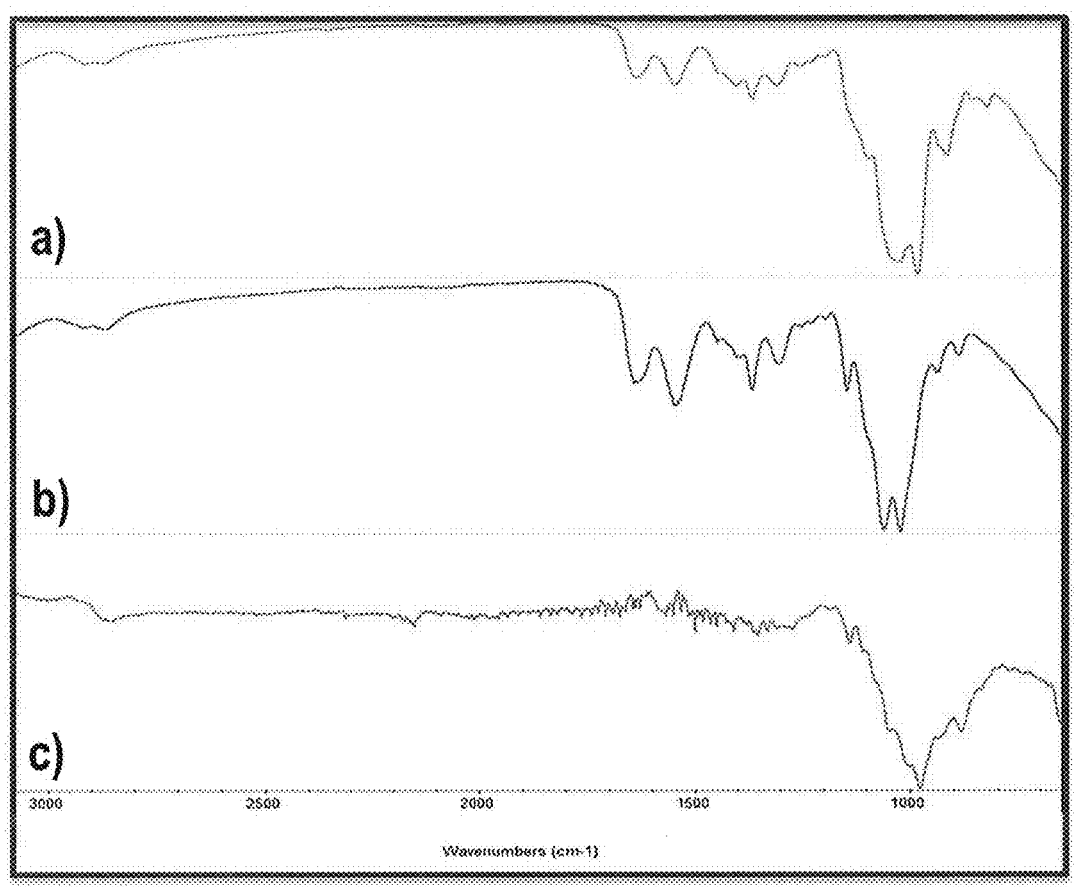
FIG. 32 shows an FITR results, that confirm the successful methacrylate grafting into the chitosan backbone structure.

Methacrylated chitosan (MACh) was synthesized (FIG. 30) by mixing acetic acid, deionized (DI) water, chitosan, methacrylate anhydride, and pyridine. Ethanol was added to stabilize the linear chitosan chains dissolved in acetic acid, exposing more of the amino groups to methacrylate anhydride. Conversely, too much ethanol promotes gelation of the solution, halting the methacrylation process (Lu et al., 2004). The degree of methacrylation determines solubility in water. Six different volumes of ethanol were chosen to determine this point of gelation which was signified by a solidified material. 45 mL of ethanol were used due to the fact that it was the highest volume added without gelation; the lack of gelation signified that the methacrylate chain was still open for reactions. After synthesis, the solution was dialyzed against ultrapure water (18.2Ω). Once purified, two groups were created from the solution to be freeze-dried for one week: 1) MACh without sucrose, and (2) MACh with added sucrose in a 1:1 mole ratio to chitosan. Successful methacrylation of the chitosan chains was tested for after freeze-drying with the aid of FTIR. Additionally, each group was tested for solubility. Three trials were conducted where 0.2 g of each MACh group were dissolved into 60 mL of DI water. These samples were then stirred with a magnetic stir rod at 200 rpm for 8 minutes at 37° C. After stirring and vacuum filtration, the samples were freeze-dried for 72 hours and weighed to determine the percent dissolved. To synthesize the bio-ink, 4 wt. % MACh+sucrose was used, and IRGACURE 2959 was used as the photo-initiator for cross-linking (FIG. 2). Once loaded in the printer, the following dimensions were used for the micro-patterning of a scaffold: (1) 6 mm×8 mm scaffold, (2) 0.6 mm×0.6 mm grid size, (3) 15 layers thick, and (4) a printing speed of 10 mm/sec. During printing, cross-linking was initiated by UV light (365 nm, 42 mW·cm−2) at the tip of the printer nozzle. The microstructure of the micro-patterned scaffold was then analyzed with a scanning electron microscope.

Figure 33:
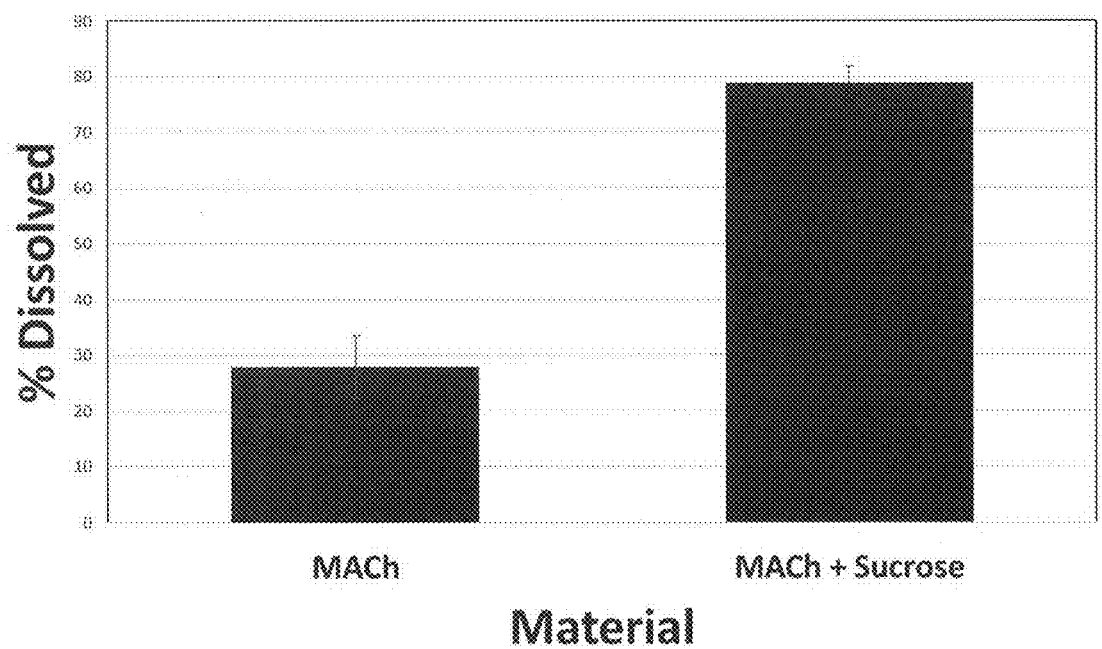
FIG. 33—After freeze-drying for 72 hours and weighing the samples, MACh with added sucrose was shown to have a greater rate of dissolution. The addition of sucrose acts as a stabilizing agent to the chitosan chains, guarding against freezing stress.

The results in FIG. 33 present FTIR confirmation of successful methacrylate grafting into the chitosan backbone. In FIGS. 3a (MACh without sucrose) and 3b (MACh with sucrose), the presence of a carbon-carbon double bond is signified with peaks between 1630-1680. This double bond is characteristic of the grafted methacrylate group. In FIG. 3c, chitosan was tested with FTIR as a control. There is no peak present in this range, which further demonstrated successful methacrylation.

Figure 34:
FIG. 34—MACh without sucrose had little to no solubility in DI (deionized) water.

The results in FIG. 34 demonstrate that after freeze-drying for 72 hours and weighing the samples, MACh with added sucrose had a greater rate of dissolution in all three trials (MACh: $\bar{x}$=27.83%, SE=5.73; MaCh+sucrose: $\bar{x}$=78.67%, SE=3.17). The addition of sucrose to the MACh serves as a stabilizing agent to the chitosan chains that would normally suffer from freezing stress, thus allowing for greater dissolution. The methodology of this stabilization is explained by the role of sucrose acting as a water replacement while the MACh undergoes the freeze-drying process (Szymanska & Winnicka, 2015). From these results, it was decided that MACh with added sucrose would be used for synthesizing the bio-ink for 3D printing.

The results in FIG. 34 demonstrate that MACh without sucrose had little to no solubility in DI water; thus, this material was not able to be fabricated into a suitable ink for 3D printing. The MACh with added sucrose dissolved much more uniformly and was able to be used in the 3D printer.

Figure 35:
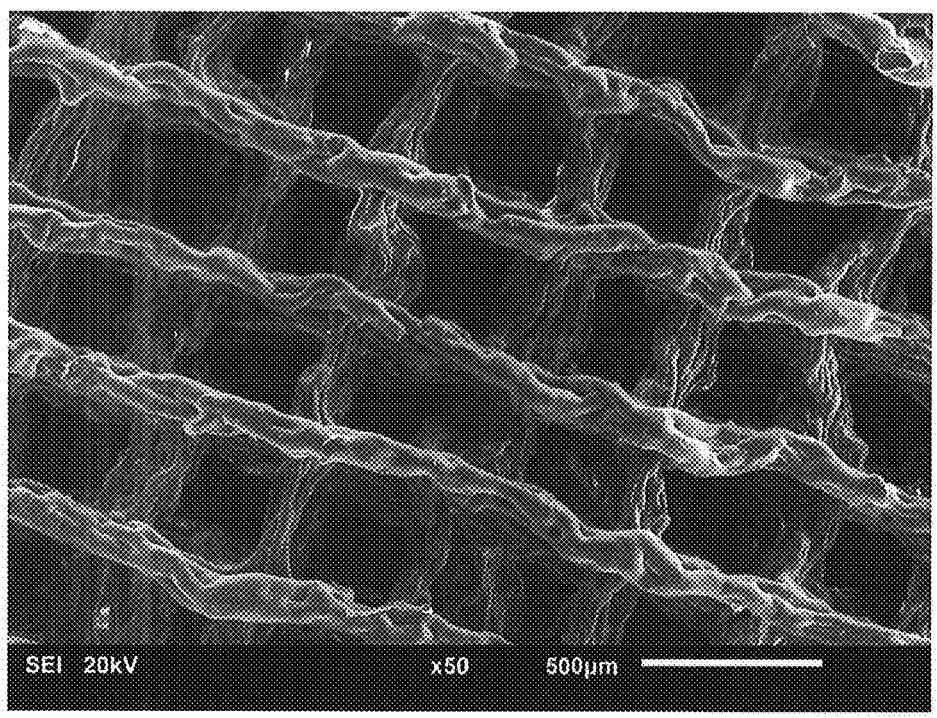
FIG. 35 Scanning electron micrograph of the micro-patterned MACh scaffold after desiccation.

FIG. 35 presents a scanning electron micrograph of the micro-patterned scaffold after desiccation. The finely printed grid of 0.6 mm×0.6 mm can be clearly seen. The rigidity and structural stability of this scaffold demonstrates successful cross-linking from the gel state.

The protocol to be used on the formulation of the bio-Inl with MACh is presented below:

Protocol:
1. Add 50 mL of DI water
2. 0.75 mL of concentrated acetic acid
3. Add 1 g of chitosan gradually to avoid agglutination
4. Add 45 mL of ethanol
5. Add 20 drops of pyridine dropwise until solution becomes less cloudy
6. Add 1.928 mL of MA Anhydride drop-wise
   a. Dropped in at a rate of 1 drop every 3 seconds
7. Allowed to react at ****50 degrees Celsius for 2 hours with a large stir magnet stirring vigorously
8. Dialyzed against ultrapure water in the semi-permeable membrane casing at ****50 degrees Celsius
   a. Use a large magnetic stir rod
   b. Take care to completely change out the ultrapure water daily to ensure adequate dialysis
9. After a few days, MACh will be thicker, purer, and ready to be freeze dried
10. Add sucrose in a 1:1 mole ratio with chitosan before freeze-drying
11. Freeze dry for a few days, then dehydrated MACh is ready for bioInk synthesis Example 7—Additive In-Situ 3D Printing of Bone Regenerating Scaffolds for Applications of Bone Defect Healing Bone substitution according to current procedures requires 2 separate steps. First creating bone defect and measure the defect shape and dimensions, and then implanting the custom prosthesis, scaffold, or autograft. However the limitations in these procedures include mismatch between the scaffold and the defect and displacement of the scaffold during implantation, and incomplete healing/tissue formation at the perimeter of the defect. Additive in-situ 3D printing overcomes these limitations by printing scaffolds directly into a defect site that conform to the dimensions of the defect site in situ.

In the present invention, several nano-biosilica-based 3D scaffolds with adequate 3D printing properties to potentially improve implantability and rapid bone healing capability.

These scaffolds are demonstrated here to be reproducible and formed the intended porosity and chemistry for bone healing. In vitro and in vivo testing will be discussed. microstructure and chemical properties of the proposed material will be presented.

While the present methods and healing results present many advantages over conventional approaches, a few of these advantages include:
1. Shelf Life is Extended—Gel preparations may be stored for emergency applications and provided when needed for use in any of a variety of forms:
   a. From powder to gel
   b. Start from powders
   c. Takes about 10-20 minutes to mix, centrifuge, de-aerate, and then load into syringe.
   d. Then 30-45 minutes for heating at around 37-40° C.
   e. For the gel
   f. Shelf life is about an hour
   g. After 1 hour at 1 bar and 25 C, the solution will become difficult to extrude
   h. Heat at 37-40° C. for 10-15 minutes to reconstitute the extrusion-ready preparation
   i. shelf-life at −20 C can be up to 6 months, and shelf life at −80 C can be up to 1 year for MACh or MAG.
2. Provides a point-of-care bone repair or tissue repair preparation, permitting remote and/or rural community care where medical facilities are not readily accessible (war-zone, emergency care, disaster site).

3. Target viscosity of about 300 mili Pascals to less than about 1 Pascal (such as between about 300 mili Pascals and 950 mili Pascals, or 99 mili Pascals) for extrusion in a temperature range between 25-40 degrees C.
4. Effective as a Clotting Agent on Contact with Tissue/Wound Materials disclosed possess the ability to clot bleeding area in about 15-30 seconds
5. Powdered preparations of Product may be created and thereafter stored for longer term storage by heating and evaporating water from saline. The powdered preparations may include any of the following compositions:
   a. Powdered LP-MAG-sucrose
   b. Powdered MAG alone
   c. Powdered LP-sucrose
   d. All of the above powders can be sold with any photo-initiator that one desires In addition, the following specific formulations of the powders may be provided as particular product embodiments of the invention, and used alone or together in the fabrication of scaffolds, as a wound or bone repair medicament, or in 3-D printing protocols, as described herein.

Powder Formulations:
   1. Powdered composition of LP-MAG-sucrose
      0.1 to 0.3 g Lp
      0.1 to 0.3 g sucrose
      1.0 to 1.5 g MAG (55.5% gelatin to 44.5% methacrylate)
      Total g is 1.2 g to 2.1 g total
   2. Powdered version of LP-MAG-surcrose-irgacure
      0.1 to 0.3 g Lp
      0.1 to 0.3 g sucrose
      1.0 to 1.5 g MAG (55.5% gelatin to 44.5% methacrylate)
      0.022 to 0.066 g Irgacure photo-initiator
      1.222 to 2.166 g total
   3. Sucrose
      Cane sugar
      Fructose corn syrup
      Fructose
      Honey
      Chocolate
      Artificial Sugar substitute (Splenda, Sweet and low)
      Brown or White sugar
   4. Photo-initiator of choice
      Irgacure 2959
      Irgacure 651
      Irgacure 184
      Ciba darocur 1173
      Irgacure TPO-L
   5 LP-MAG bonding
      Covalent bonding between LP and gelatin
      Van der Waals bonding
      Hydrogen bonding
      Electrostatic interaction with LP (negative) and amine group in gelatin (positive)
   6. 3d live printing+Proprietary bio-Ink advantages:
      Fixation—scaffolds are not easy to fixate into bone. Often, PMMA is needed to fix the scaffold in place. The present methods cross-link gelatin or chitrosan directly to connective tissue within bone layers. Polymethyl-methacrylate (PMMA) is a glue that does not allow for any healing into PMMA layers. Avoiding its use is advantageous as it allows for bone tissue to replace scaffold rather than encapsulate PMMS. PMMA also uses harsh solvents that can be toxic to bone cells and tissue.
      Fitting during implantation. Scaffold printing and implantation is often difficult due to exact fit of the scaffold to the defect dimensions, handling, and large gap (>1 cm) between scaffold and bone. Direct printing into the defect allows for 0.05-0.1 mm gap between scaffold and bone without need for handling by operator.
      Bleeding—bleeding at the site of the defect can be an issue as scar tissue can form. Our materials can absorb blood and spread throughout the scaffold. This is advantageous as the blood can be sustained for its release in the defect site.
      Cell Spreading: cell attachment, migration, and spreading can take several weeks. This is a primary limitation to scaffold stimulation of bone formation. Our method spreads incoming stem cells that come in with blood and spreads them into the scaffold along with the blood. This allows for faster bone formation.
   7. Bolus application of bio-Ink—It is envisioned that the LP-MAG and LP-MAC materials may also be used as a tissue treatment for healing, or tissue "cement" (tissue glue) in various applications where a living tissue has been comprised and/or injured. For example, where a micro-tissue (bone) crack is detected.

It is envisioned that any one of the above preparations may be formulated with the Lp-MAC as well as Lp-MAG composite materials described herein.

Example 8—Tissue Defect Coverage with 3d Printing Technique

It is estimated that the present methods will provide an up to at least 95% or even up 99.98% filling of the damaged tissue area volume. This damaged tissue will include bone or soft tissue. This calculation is established by reference to the healing margin area achieved by the 3d printing technique shown in bone.

By way of example, a bone defect having the dimensions of 6 mm×4 mm×0.6 mm as was shown in the rat model can be filled with a scaffold-bone margin of 0.1 mm×0.1 mm×0.1 mm for 99.98% tissue defect filling. While currently employed methods of tissue repair 50-80% in tissue volume efficiency, the methods given in this patent application can give as much as 95-99.98% tissue volume filling. The improvement is 20-49% healing volume as compared to other scaffold systems.

Example 9—Improvements to Formulation—MAG-Lp Preparation

It has been determined that the optimal conditions for adding methacylate to gelatin during MAG preparation is provided under the following conditions and/or settings.
1. The syringe pump speed for adding methyl acrylate is 12 ml/h. to 13.2 ml/h.
2. Laponite, sucrose and irgacure are added in 4 intervals, adding 25% each of the laponite, sucrose and Irgagure.

BIBLIOGRAPHY

The following references are specifically incorporated herein in their entirety
1. Vacanti C A. Journal of Cellular and Molecular Medicine 2006; 10:569-76.
2. Langer R, Vacanti J P. Tissue engineering. Science (New York, N.Y.) 1993; 260:920-6.
3. Sipe J D. Tissue Engineering and Reparative Medicine. Annals of the New York Academy of Sciences 2002; 961:1-9.

4. Langer R, Vacanti J. Tissue engineering. Science (New York, N.Y.) 1993; 260:920-6.
5. Saxena S, et al. Macromolecular bioscience 2011; 11:373-82.
6. Chapman M W. Chapman's orthopaedic surgery: Philadelphia: Lippincott Williams & Wilkins, [2001] Third edition.; 2001.
7. Grundnes O, Reikeras O. Acta orthopaedica Scandinavica 1993; 64:340-2.
8. Glowacki J. Angiogenesis in fracture repair. Clin Orthop Relat Res 1998:S82-9.
9. Bolander M E. Regulation of fracture repair by growth factors. Proceedings of the Society for Experimental Biology and Medicine Society for Experimental Biology and Medicine (New York, N.Y.) 1992; 200:165-70.
10. McKibbin B. The biology of fracture healing in long bones. The Journal of bone and joint surgery British volume 1978; 60-b:150-62.
11. Rockwood C A, Green D P, Bucholz R W. Rockwood & Green's fractures in adults: Philadelphia, Pa.: Lippincott, Williams & Wilkins, [2010] Seventh edition.; 2010.
12. Lieberman J R, Friedlaender G E. Bone regeneration and repair: biology and clinical applications. edited by Jay R. Lieberman and Gary E. Friedlander: Totowa, N.J.: Humana Press, [2005]; 2005.
13. Arnett T R. The Journal of nutrition 2008; 138:415s-8s.
14. Bord S, Horner A, Hembry R M, Reynolds J J, Compston J E. Production of collagenase by human osteoblasts and osteoclasts in vivo. Bone 1996; 19:35-40.
15. Raggatt L J, Partridge N C. The Journal of biological chemistry 2010; 285:25103-8.
16. Shi D. Introduction to biomaterials. Donglu Shi, editor: Beijing, China: Tsinghua University Press; Singapore: World Scientific: c2006, [date of publication not identified]; 2006.
17. Bronzino J D. The Biomedical engineering handbook. United States: CRC Press; 1995.
18. Poitout D G. Biomechanics and Biomaterials in Orthopedics. London: Springer London; 2004.
19. Williams D F. Essential biomaterials science. David Williams: Cambridge, United Kingdom; New York: Cambridge University Press, 2014; 2014.
20. Annabi N, Nichol J W, Zhong X, Ji C, Koshy S, Khademhosseini A, et al. Controlling the Porosity and Microarchitecture of Hydrogels for Tissue Engineering. Tissue Engineering Part B, Reviews 2010; 16:371-83.
21. Brock A, Chang E, Ho C C, LeDuc P, Jiang X, Whitesides G M, et al. Geometric determinants of directional cell motility revealed using microcontact printing. Langmuir: the ACS journal of surfaces and colloids 2003; 19:1611-7.
22. Toyota T, Wakamoto Y, Hayashi K, Ohnuma K. Controlling Cell Migration with Micropatterns. In: Agbo E C, editor. Innovations in Biotechnology: InTech; 2012.
23. Sunami H, Yokota I, Igarashi Y. Biomaterials Science 2014; 2:399-409.
24. Yoon S-H, Kim Y K, Han E D, Seo Y-H, Kim B H, Mofrad M R K. Lab on a Chip 2012; 12:2391-402.
25. Murphy C M, O'Brien F J. Understanding the effect of mean pore size on cell activity in collagen-glycosaminoglycan scaffolds. Cell Adhesion & Migration 2010; 4:377-81.
26. Tarafder S, Balla V K, Davies N M, Bandyopadhyay A, Bose S. Microwave-sintered 3D printed tricalcium phosphate scaffolds for bone tissue engineering. Journal of tissue engineering and regenerative medicine 2013; 7:631-41.
27. Karageorgiou V, Kaplan D. Porosity of 3D biomaterial scaffolds and osteogenesis. Biomaterials 2005; 26:5474-91.
28. Xue W, Krishna B V, Bandyopadhyay A, Bose S. Processing and biocompatibility evaluation of laser processed porous titanium. Acta biomaterialia 2007; 3:1007-18.
29. Otsuki B, Takemoto M, Fujibayashi S, Neo M, Kokubo T, Nakamura T. Pore throat size and connectivity determine bone and tissue ingrowth into porous implants: Three-dimensional micro-CT based structural analyses of porous bioactive titanium implants. Biomaterials 2006; 27:5892-900.
30. Bone Grafts and Substitutes Market (By Type: Allografts, and Bone Graft Substitutes; By Application: Spinal Fusion, Long Bone, Foot and Ankle, Craniomaxillofacial, Joint Reconstruction, and Dental)—Global Industry Analysis, Size, Share, Growth, Trends and Forecast 2015-2023. Transparency Market Research; 2016. p. 87.
31. Bucholz R W. Nonallograft osteoconductive bone graft substitutes. Clin Orthop Relat Res 2002:44-52.
32. Damien C J, Parsons J R. Bone graft and bone graft substitutes: a review of current technology and applications. Journal of Applied Biomaterials 1991; 2:187-208.
33. Younger E M, Chapman M W. Morbidity at bone graft donor sites. Journal of orthopaedic trauma 1989; 3:192-5.
34. Panetta N J, Gupta D M, Slater B J, Kwan M D, Liu K J, Longaker M T. Tissue engineering in cleft palate and other congenital malformations. Pediatric research 2008; 63:545-51.
35. Oppenheimer A J, Tong L, Buchman S R. Craniofacial Bone Grafting: Wolff's Law Revisited. Craniomaxillofacial Trauma & Reconstruction 2008; 1:49-61.
36. McCarthy J G, Stelnicki E J, Mehrara B J, Longaker M T. Distraction osteogenesis of the craniofacial skeleton. Plastic and reconstructive surgery 2001; 107:1812-27.
37. Bell R B. Computer planning and intraoperative navigation in cranio-maxillofacial surgery. Oral and maxillofacial surgery clinics of North America 2010; 22:135-56.
38. Hutmacher D W. Scaffolds in tissue engineering bone and cartilage. Biomaterials 2000; 21:2529-43.
39. Bose S, Vahabzadeh S, Bandyopadhyay A. Bone tissue engineering using 3D printing. Materials Today 2013; 16:496-504.
40. Cesarano III J, Calvert P D. Freefou ling objects with low-binder slurry. Google Patents; 2000.
41. Lewis J A, Smay J E, Stuecker J, Cesarano J. Direct Ink Writing of Three-Dimensional Ceramic Structures. Journal of the American Ceramic Society 2006; 89:3599-609.
42. Joshi A M. Process planning for the rapid machining of custom bone implants USA: Iowa State University; 2011.
43. Beger H G. From Archiv fur Klinische Chirurgie to Langenbeck's Archives of Surgery: 1860-2010. Langenbeck's archives of surgery/Deutsche Gesellschaft fur Chirurgie 2010; 395 Suppl 1:3-12.
44. Wang W, Ouyang Y, Poh C K. Orthopaedic implant technology: biomaterials from past to future. Annals of the Academy of Medicine, Singapore 2011; 40:237-44.
45. Norowski P A, Jr., Bumgardner J D. Biomaterial and antibiotic strategies for peri-implantitis: a review. Journal of biomedical materials research Part B, Applied biomaterials 2009; 88:530-43.
46. Bhumiratana S, Vunjak-Novakovic G. Concise Review: Personalized Human Bone Grafts for Reconstructing Head and Face. Stem Cells Transl Med 2012; 1:64-9.

47. Elsalanty M E, Genecov D G. Bone Grafts in Craniofacial Surgery. Craniomaxillofacial Trauma & Reconstruction 2009; 2:125-34.
48. Kokubo T, Kim H M, Kawashita M. Novel bioactive materials with different mechanical properties. Biomaterials 2003; 24:2161-75.
49. Guda T, Walker J A, Pollot B E, Appleford M R, Oh S, Ong J L, et al. In vivo performance of bilayer hydroxyapatite scaffolds for bone tissue regeneration in the rabbit radius. Journal of materials science Materials in medicine 2011; 22:647-56.
50. Shih T C, Teng N C, Wang P D, Lin C T, Yang J C, Fong S W, et al. In vivo evaluation of resorbable bone graft substitutes in beagles: histological properties. Journal of biomedical materials research Part A 2013; 101:2405-11.
51. Rent D M, Ogston N, Jugdaohsingh R, Cheung H F J, Evans B A J, Thompson R P H, et al. Orthosilicic acid stimulates collagen type 1 synthesis and osteoblastic differentiation in human osteoblast-like cells in vitro. Bone 2003; 32:127-35.
52. Varanasi V G, Saiz E, Loomer P M, Ancheta B, Uritani N, Ho S P, et al. Enhanced osteocalcin expression by osteoblast-like cells (MC3T3-E1) exposed to bioactive coating glass ($SiO_2$-CaO—$P_2O_5$-MgO—$K_2O$—$Na_2O$ system) ions. Acta biomaterialia 2009; 5:3536-47.
53. Varanasi V G, Owyoung J B, Saiz E, Marshall S J, Marshall G W, Loomer P M. The ionic products of bioactive glass particle dissolution enhance periodontal ligament fibroblast osteocalcin expression and enhance early mineralized tissue development. Journal of biomedical materials research Part A 2011; 98A:177-84.
54. Hoppe A, Guldal N S, Boccaccini A R. A review of the biological response to ionic dissolution products from bioactive glasses and glass-ceramics. Biomaterials 2011; 32:2757-74.
55. Maehira F, Iinuma Y, Eguchi Y, Miyagi I, Teruya S. Effects of soluble silicon compound and deep-sea water on biochemical and mechanical properties of bone and the related gene expression in mice. Journal of bone and mineral metabolism 2008; 26:446-55.
56. Izu A, Kumai T, Tohno Y, Tohno S, Minami T, Yamada G, et al. Silicon intake to vertebral columns of mice after dietary supply. Biological trace element research 2006; 113:297-316.
57. Rahaman M N, Day D E, Bal B S, Fu Q, Jung S B, Bonewald L F, et al. Bioactive glass in tissue engineering. Acta biomaterialia 2011; 7:2355-73.
58. Kobayashi H, Turner A S, Seim H B, 3rd, Kawamoto T, Bauer T W. Evaluation of a silica-containing bone graft substitute in a vertebral defect model. Journal of biomedical materials research Part A 2010; 92:596-603.
59. Knapp C I, Feuille F, Cochran D L, Mellonig J T. Clinical and histologic evaluation of bone-replacement grafts in the treatment of localized alveolar ridge defects. Part 2: bioactive glass particulate. The International journal of periodontics & restorative dentistry 2003; 23:129-37.
60. Zhao S, Zhang J, Zhu M, Zhang Y, Liu Z, Tao C, et al. Three-dimensional printed strontium-containing mesoporous bioactive glass scaffolds for repairing rat critical-sized calvarial defects. Acta biomaterialia 2015; 12:270-80.
61. Sui B, Zhong G, Sun J. Evolution of a Mesoporous Bioactive Glass Scaffold Implanted in Rat Femur Evaluated by 45Ca Labeling, Tracing, and Histological Analysis. ACS Applied Materials & Interfaces 2014; 6:3528-35.
62. Kretlow J D, Young S, Klouda L, Wong M, Mikos A G. Injectable Biomaterials for Regenerating Complex Craniofacial Tissues. Advanced materials (Deerfield Beach, Fla.) 2009; 21:3368-93.
63. Dunne M, Corrigan I, Ramtoola Z. Influence of particle size and dissolution conditions on the degradation properties of polylactide-co-glycolide particles. Biomaterials 2000; 21:1659-68.
64. Gentile P, Chiono V, Carmagnola I, Hatton P V. An Overview of Poly(lactic-co-glycolic) Acid (PLGA)-Based Biomaterials for Bone Tissue Engineering. International Journal of Molecular Sciences 2014; 15:3640-59.
65. Sanger C, Soto A, Mussa F, Sanzo M, Sardo L, Donati P A, et al. Maximizing results in craniofacial surgery with bioresorbable fixation devices. The Journal of craniofacial surgery 2007; 18:926-30.
66. Fedorowicz Z, Nasser M, Newton J T, Oliver R J. Resorbable versus titanium plates for orthognathic surgery. The Cochrane database of systematic reviews 2007: Cd006204.
67. Bell R B, Kindsfater C S. The use of biodegradable plates and screws to stabilize facial fractures. Journal of oral and maxillofacial surgery: official journal of the American Association of Oral and Maxillofacial Surgeons 2006; 64:31-9.
68. Laughlin R M, Block M S, Wilk R, Malloy R B, Kent J N. Resorbable plates for the fixation of mandibular fractures: a prospective study. Journal of oral and maxillofacial surgery: official journal of the American Association of Oral and Maxillofacial Surgeons 2007; 65:89-96.
69. Kawasaki K. Bone 1998; 23:223-31.
70. Meng Z X, Li H F, Sun Z Z, Zheng W, Zheng Y F. Fabrication of mineralized electrospun PLGA and PLGA/gelatin nanofibers and their potential in bone tissue engineering. Materials science & engineering C, Materials for biological applications 2013; 33:699-706.
71. Ito Y. Covalently immobilized biosignal molecule materials for tissue engineering. Soft Matter 2008; 4:46-56.
72. Yoon J J, Song S H, Lee D S, Park T G. Biomaterials 2004; 25:5613-20.
73. Pierschbacher M D, Ruoslahti E. Cell attachment activity of fibronectin can be duplicated by small synthetic fragments of the molecule. Nature 1984; 309:30-3.
74. Loth T, Hotzel R, Kascholke C, Anderegg U, Schulz-Siegmund M, Hacker M C. Gelatin-Based Biomaterial Engineering with Anhydride-Containing Oligomeric Cross-Linkers. Biomacromolecules 2014; 15:2104-18.
75. Nichol J W, Koshy S T, Bae H, Hwang C M, Yamanlar S, Khademhosseini. Biomaterials 2010; 31:5536-44.
76. Balazs A C, Emrick T, Russell T P. Nanoparticle polymer composites: where two small worlds meet. Science (New York, N.Y.) 2006; 314:1107-10.
77. Bordes P, Pollet E, Averous L. Nano-biocomposites: Biodegradable polyester/nanoclay systems. Progress in Polymer Science 2009; 34:125-55.
78. Xavier J R. ACS nano 2015.
79. Wu C-J, Gaharwar A K, Schexnailder P J, Schmidt G. Development of Biomedical Polymer-Silicate Nanocomposites: A Materials Science Perspective. Materials 2010; 3:2986-3005.
80. Gaharwar A K, Mihaila S M, Swami A, Patel A, Sant S, Reis R L, et al. Advanced materials 2013; 25:3329-36.
81. Dolatshahi-Pirouz A, et al. A combinatorial cell-laden gel microarray for inducing osteogenic differentiation of human mesenchymal stem cells. Scientific reports 2014; 4:3896.

82. Thompson D W, Butterworth J T. Journal of Colloid and Interface Science 1992; 151:236-43.
83. Boral S, Gupta A N, Bohidar H B. International Journal of Biological Macromolecules 2006; 39:240-9.
84. Al-Ruqaie I M, Kasapis S, Abeysekera R. Structural properties of pectin-gelatin gels. Part II effect of sucrose-glucose syrup. Carbohydrate polymers 1997; 34:309-21.
85. Nishinari K, Watase M, Kohyama K, Nishinari N, Oakenfull D, Koide S, et al. The Effect of Sucrose on the Thermo-Reversible Gel-Sol Transition in Agarose and Gelatin. Polym J 1992; 24:871-7.
86. Weaver C M, Daniel J R. The Food Chemistry Laboratory: A Manual for Experimental Foods, Dietetics, and Food Scientists, Second Edition. USA: CRC Press 2003.
87. Sabnis A, Rahimi M, Chapman C, Nguyen K T. Cytocompatibility studies of an in situ photopolymerized thermoresponsive hydrogel nanoparticle system using human aortic smooth muscle cells. Journal of biomedical materials research Part A 2009; 91:52-9.
88. Loessner D, Meinert C, Kaemmerer E, Martine L C, Yue K, Levett P A, et al. Functionalization, preparation and use of cell-laden gelatin methacryloyl-based hydrogels as modular tissue culture platforms. Nat Protocols 2016; 11:727-46.
89. Normand V, Muller S, Ravey J-C, Parker A. Gelation Kinetics of Gelatin: A Master Curve and Network Modeling. Macromolecules 2000; 33:1063-71.
90. Patel R G, Purwada A, Cerchietti L, Inghirami G, Melnick A, Gaharwar A K, et al. Microscale Bioadhesive Hydrogel Arrays for Cell Engineering Applications. Cellular and molecular bioengineering 2014; 7:394-408.
91. Zandi M. Studies on the Gelation of Gelatin Solutions and on the Use of Resulting Gels for Medical Scaffolds: Universitat Duisburg-Essen; 2008.
92. Ilyas A, Odatsu T, Shah A, Monte F, Kim H K W, Kramer P, et al. Amorphous Silica: A New Antioxidant Role for Rapid Critical-Sized Bone Defect Healing. Adv Healthcare Mater 2016; Under publication.
93. Bouxsein M L, Boyd S K, Christiansen B A, Guldberg R E, Jepsen K J, Muller R. Guidelines for assessment of bone microstructure in rodents using micro-computed tomography. Journal of bone and mineral research: the official journal of the American Society for Bone and Mineral Research 2010; 25:1468-86.
94. Mandair G S, Morris M D. Contributions of Raman spectroscopy to the understanding of bone strength. BoneKEy Rep 2015; 4.
95. Tarnowski C P, Ignelzi M A, Jr., Morris M D. Mineralization of developing mouse calvaria as revealed by Raman microspectroscopy. Journal of bone and mineral research: the official journal of the American Society for Bone and Mineral Research 2002; 17:1118-26.
96. McElderry D P. DYNAMICS OF MINERALIZATION DURING BONE DEVELOPMENT: The University of Michigan; 2012.
97. Shin H, Olsen B D, Khademhosseini A. The mechanical properties and cytotoxicity of cell-laden double-network hydrogels based on photocrosslinkable gelatin and gellan gum biomacromolecules. Biomaterials 2012; 33:3143-52.
98. Grill A. Porous pSiCOH Ultralow-k Dielectrics for Chip Interconnects Prepared by PECVD. Annual Review of Materials Research 2009; 39:49-69.
99. Dragusin D-M, Van Vlierberghe S, Dubruel P, Dierick M, Van Hoorebeke L, Declercq H A, et al. Novel gelatin-PHEMA porous scaffolds for tissue engineering applications. Soft Matter 2012; 8:9589-602.
100. Wang H, Zhou L, Liao J, Tan Y, Ouyang K, Ning C, et al. Cell-laden photocrosslinked GelMA-DexMA copolymer hydrogels with tunable mechanical properties for tissue engineering. Journal of Materials Science: Materials in Medicine 2014; 25:2173-83.
101. Saraiva S M, Miguel S P, Ribeiro M P, Coutinho P, Correia I J. Synthesis and characterization of a photocrosslinkable chitosan-gelatin hydrogel aimed for tissue regeneration. RSC Advances 2015; 5:63478-88.
102. Ferry J D. Viscoelastic properties of polymers: New York: Wiley, [1961]; 1961.
103. Pierre A C. Introduction to Sol-Gel Processing. USA: Springer; 1998.
104. Tan B H, Tan J P K, Tam K C. pH-Responsive Nanogels: Synthesis and Physical Properties. Hydrogel Micro and Nanoparticles: Wiley-VCH Verlag GmbH & Co. KGaA; 2012. p. 81-115.
105. Saha P K. Aluminum Extrusion Technology. Ohio, USA: ASM International®; 2000.
106. Hygienists ACoGI. Documentation of the Threshold Limit Values and Biological Exposure Indices, 7th Edition. USA: ACGIH; 2015. p. 238.
107 Anseth K S, Shastri V R, Langer R. Photopolymerizable degradable polyanhydrides with osteocompatibility. Nat Biotech 1999; 17:156-9.
108. Kini U, Nandeesh B N. Physiology of Bone Formation, Remodeling, and Metabolism. In: Fogelman I, Gnanasegaran G, van der Wall H, editors. Radionuclide and Hybrid Bone Imaging. Berlin, Heidelberg: Springer Berlin Heidelberg; 2012. p. 29-57.
109. Rinaldi M, Esposti A, Mottola A, Ganz S D. Chapter 3—Computer-Assisted Implant Surgery. Computer-Guided Applications for Dental Implants, Bone Grafting, and Reconstructive Surgery (Adapted Translation). St. Louis: Elsevier; 2016. p. 96-123.
110. Gaharwar A K, Mukundan S, Karaca E, Dolatshahi-Pirouz A, Patel A, Rangarajan K, et al. Nanoclay-enriched poly(varepsilon-caprolactone) electrospun scaffolds for osteogenic differentiation of human mesenchymal stem cells. Tissue engineering Part A 2014; 20:2088-101.
111. Mihaila S M, Gaharwar A K, Reis R L, Khademhosseini A, Marques A P, Gomes M E. The osteogenic differentiation of SSEA-4 sub-population of human adipose derived stem cells using silicate nanoplatelets. Biomaterials 2014; 35:9087-99.
112. Murphy S V, Atala A. 3D bioprinting of tissues and organs. Nature biotechnology 2014; 32:773-85.
113. Kozlov P V, Burdygina G I. The structure and properties of solid gelatin and the principles of their modification. Polymer 1983; 24:651-66.
114. Sachar A, Strom T A, Serrano M J, Benson M D, Oppeiinan L A, Svoboda K K, et al. Osteoblasts responses to three-dimensional nanofibrous gelatin scaffolds. Journal of biomedical materials research Part A 2012; 100: 3029-41.
115. Wischke C, Borchert H H. Fluorescein isothiocyanate labelled bovine serum albumin (FITC-BSA) as a model protein drug: opportunities and drawbacks. Die Pharmazie 2006; 61:770-4.
116. Wang Y, Yan L, Li B, Qi Y, Xie Z, Jing X, et al. Protein-Resistant Biodegradable Amphiphilic Graft Copolymer Vesicles as Protein Carriers. Macromolecular bioscience 2015; 15:1304-13.
117. Ma C, Jing Y, Sun H, Liu X. Hierarchical Nanofibrous Microspheres with Controlled Growth Factor Delivery for Bone Regeneration. Advanced Healthcare Materials 2015; 4:2699-708.

118. Boomer L, Liu Y, Mahler N, Johnson J, Zak K, Nelson T, et al. Scaffolding for challenging environments: materials selection for tissue engineered intestine. Journal of biomedical materials research Part A 2014; 102:3795-802.

119. Hutson C B, Nichol J W, Aubin H, Bae H, Yamanlar S, Al-Haque S, et al. Synthesis and characterization of tunable poly(ethylene glycol): gelatin methacrylate composite hydrogels. Tissue engineering Part A 2011; 17:1713-23.

120. Kim P, Yuan A, Nam K H, Jiao A, Kim D H. Fabrication of poly(ethylene glycol): gelatin methacrylate composite nanostructures with tunable stiffness and degradation for vascular tissue engineering. Biofabrication 2014; 6:024112.

121. Benton J A, DeForest C A, Vivekanandan V, Anseth K S. Photocrosslinking of gelatin macromers to synthesize porous hydrogels that promote valvular interstitial cell function. Tissue engineering Part A 2009; 15:3221-30.

122. Head D L, Yankeelov J A, Jr. The effect of calcium chloride on the activity and inhibition of bacterial collagenase. International journal of peptide and protein research 1976; 8:155-65.

123. Moore S, Stein W H. Photometric ninhydrin method for use in the chromatography of amino acids. The Journal of biological chemistry 1948; 176:367-88.

124. Thomas P C, Cipriano B H, Raghavan S R. Nanoparticle-crosslinked hydrogels as a class of efficient materials for separation and ion exchange. Soft Matter 2011; 7:8192-7.

125. Odatsu T, Azimaie T, Velten M F, Vu M, Lyles M B, Kim H K, et al. Human periosteum cell osteogenic differentiation enhanced by ionic silicon release from porous amorphous silica fibrous scaffolds. Journal of biomedical materials research Part A 2015; 103:2797-806.

126. Mladenovska K, Kumbaradzi E, Dodov G, Makraduli L, Goracinova K. Biodegradation and drug release studies of BSA loaded gelatin microspheres. International journal of pharmaceutics 2002; 242:247-9.

127. Li P, Kim N H, Siddaramaiah, Lee J H. Swelling behavior of polyacrylamide/laponite clay nanocomposite hydrogels: pH-sensitive property. Composites Part B: Engineering 2009; 40:275-83.

128. Wahl L M, Mergenhagen S E. Regulation of monocyte/macrophage collagenase. Journal of Oral Pathology & Medicine 1988; 17:452-5.

129. Benton J A, DeForest C A, Vivekanandan V, Anseth K S. Photocrosslinking of Gelatin Macromers to Synthesize Porous Hydrogels That Promote Valvular Interstitial Cell Function. TISSUE ENGINEERING: Part A 2009; 15:10.

130. Gaharwar A K, Schexnailder P J, Kline B P, Schmidt G. Assessment of using laponite cross-linked poly(ethylene oxide) for controlled cell adhesion and mineralization. Acta biomaterialia 2011; 7:568-77.

131. Zhuang H, Zheng J P, Gao H, De Yao K. In vitro biodegradation and biocompatibility of gelatin/montmorillonite-chitosan intercalated nanocomposite. Journal of materials science Materials in medicine 2007; 18:951-7.

132. Ball M D, Bonzani I C, Bovis M J, Williams A, Stevens M M. Human periosteum is a source of cells for orthopaedic tissue engineering: a pilot study. Clin Orthop Relat Res 2011; 469:3085-93.

133. Ng A M, Saim A B, Tan K K, Tan G H, Mokhtar S A, Rose I M, et al. Comparison of bioengineered human bone construct from four sources of osteogenic cells. Journal of orthopaedic science: official journal of the Japanese Orthopaedic Association 2005; 10:192-9.

134. Nakahara H, Dennis J E, Bruder S P, Haynesworth S E, Lennon D P, Caplan A I. In vitro differentiation of bone and hypertrophic cartilage from periosteal-derived cells. Experimental cell research 1991; 195:492-503.

135. Nakahara H, Watanabe K, Sugrue S P, Olsen B R, Caplan A I. Developmental biology 1990; 142:481-5.

136. Chang H, Knothe Tate M L. Concise Review: The Periosteum: Tapping into a Reservoir of Clinically Useful Progenitor Cells. Stem Cells Translational Medicine 2012; 1:480-91.

137. Justesen J, Stenderup K, Eriksen E F, Kassem M. Maintenance of osteoblastic and adipocytic differentiation potential with age and osteoporosis in human marrow stromal cell cultures. Calcified tissue international 2002; 71:36-44.

138. Shimizu T, Sasano Y, Nakajo S, Kagayama M, Shimauchi H. The Anatomical record 2001; 264:72-81.

139. Kim H K, Oxendine I, Kamiya N. Bone 2013; 54:141-50.

140. Lebaron P, Joux F. Applied and Environmental Microbiology 1994; 60:4345-50.

141. Downs T R, Wilfinger W W. Analytical biochemistry 1983; 131:538-47.

142. Huang Z J, Haugland R P, You W M, Haugland R P. Analytical biochemistry 1992; 200:199-204.

143. Sachar A, Strom T A, San Miguel S, Serrano M J, Svoboda K K, Liu X. Journal of tissue engineering and regenerative medicine 2014; 8:862-73.

144. US Pub 2015/0054195

145. US Pub 2016/0144068

We claim:

1. A method for providing tissue repair in vivo comprising;
combining a first preparation comprising a freeze-dried preparation of a MAG or MACh material with a second preparation comprising sucrose, a silicate based nanoparticle material, and a biocompatible, non-toxic cross-linking agent, to provide a pharmacologically acceptable extrudable composition;
applying the extrudable preparation to a defined tissue region having a defined in vivo target area of soft tissue or bone tissue deficiency in an animal;
exposing the pharmaceutical composition in the defined in vivo target area to a physiologically acceptable wavelength and intensity of ultra violet light for a period of time sufficient to promote polymer cross-linking and formation of filaments; and
providing tissue repair to the defined in vivo target area in the animal.

2. The method of claim 1 wherein the in vivo target area is a bone fracture.

3. The method of claim 1 wherein the biocompatible, non-toxic cross-linking agent is 2-hydroxy-1-(4-(hydroxyethoxy) phenyl) 2-methyl-1-propanone.

4. The method of claim 2 wherein the physiologically acceptable wavelength of ultraviolet light is a 365 nm UV light illumination at an intensity of up to 50 mW/sq. cm.

5. The method of claim 1 wherein the extrudable preparation is applied in a defined series of more than one layer to provide a mesh configuration over the defined in vivo target area.

6. The method of claim 4 wherein the extrudable preparation comprises about 1% to about 20% wt. of methacrylated gelatin (MAG) or methacrylated chitosan (MACh), about 2% to about 8% silicate-based nanoparticles, and about 5% to about 20% sucrose.

\* \* \* \* \*